United States Patent
Judice et al.

(10) Patent No.: US 7,723,470 B2
(45) Date of Patent: *May 25, 2010

(54) GLYCOPEPTIDE DERIVATIVES AND PHARMACEUTICAL COMPOSITIONS CONTAINING THE SAME

(75) Inventors: J. Kevin Judice, El Granada, CA (US); Paul Ross Fatheree, San Francisco, CA (US); Bernice M. T. Lam, San Francisco, CA (US); Michael R. Leadbetter, San Leandro, CA (US); Martin S. Linsell, San Mateo, CA (US); YongQi Mu, Los Altos, CA (US); Sean Gary Trapp, San Francisco, CA (US); Guang Yang, San Mateo, CA (US); Yan Zhu, Foster City, CA (US)

(73) Assignee: Theravance, Inc., South San Francisco, CA (US)

( * ) Notice: Subject to any disclaimer, the term of this patent is extended or adjusted under 35 U.S.C. 154(b) by 103 days.

This patent is subject to a terminal disclaimer.

(21) Appl. No.: 11/977,377

(22) Filed: Oct. 24, 2007

(65) Prior Publication Data

US 2008/0103292 A1    May 1, 2008

Related U.S. Application Data

(63) Continuation of application No. 11/405,234, filed on Apr. 17, 2006, now Pat. No. 7,351,791, which is a continuation of application No. 11/128,901, filed on May 13, 2005, now Pat. No. 7,101,964, which is a continuation of application No. 10/092,088, filed on Mar. 6, 2002, now Pat. No. 6,962,970, which is a continuation of application No. 09/470,209, filed on Dec. 22, 1999, now Pat. No. 6,392,012.

(60) Provisional application No. 60/113,728, filed on Dec. 23, 1998, provisional application No. 60/129,313, filed on Apr. 14, 1999, provisional application No. 60/164,024, filed on Nov. 4, 1999, provisional application No. 60/169,978, filed on Dec. 10, 1999.

(51) Int. Cl.
*C07K 7/50* (2006.01)

(52) U.S. Cl. ............................ 530/317; 530/322; 514/8; 514/11

(58) Field of Classification Search ................ 530/317, 530/322; 514/8, 11

See application file for complete search history.

(56) References Cited

U.S. PATENT DOCUMENTS

| | | |
|---|---|---|
| 4,497,802 A | 2/1985 | Debono |
| 4,639,433 A | 1/1987 | Hunt et al. |
| 4,643,987 A | 2/1987 | Nagarajan et al. |
| 4,661,470 A | 4/1987 | Malabarba et al. |
| 4,698,327 A | 10/1987 | Nagarajan et al. |

(Continued)

FOREIGN PATENT DOCUMENTS

| | | |
|---|---|---|
| EP | 0 182 157 A2 | 5/1986 |
| EP | 0 351 597 A2 | 1/1990 |
| EP | 0 376 041 A2 | 7/1990 |
| EP | 0 460 448 B1 | 12/1991 |
| EP | 0 525 499 A1 | 2/1993 |
| EP | 0 596 929 B1 | 7/1995 |
| EP | 0 667 353 A1 | 8/1995 |
| EP | 0 801 075 A1 | 10/1997 |

(Continued)

OTHER PUBLICATIONS

Allen et al., "The Role of Hydrophobic Side Chains as Determinants of Antibacterial Activity of Semisynthetic Glycopeptide Antibiotics", The Journal of Antibiotics, vol. 50, No. 8, pp. 677-684 (1997).
Axelsen et al., "A Rational Strategy for Enhancing the Affinity of Vancomycin towards Depsipeptide Ligands", Bioorganic & Medicinal Chemistry 6, pp. 887-881 (1998).
Booth et al, "The Edman Degradation of Vancomycin: Preparation of Vancomycin Hexapeptide", J. Chem. Soc., Chem. Commun., pp. 1694-1695 (1987).

(Continued)

*Primary Examiner*—David Lukton
(74) *Attorney, Agent, or Firm*—Jeffrey A. Hagenah

(57) ABSTRACT

Disclosed are compounds of the formula:

or a trifluoroacetic acid salt thereof, wherein A, B and Fmoc are as defined herein. Such compounds are useful as synthetic intermediates for preparing glycopeptides antibiotics.

9 Claims, No Drawings

U.S. PATENT DOCUMENTS

| | | | |
|---|---|---|---|
| 4,914,187 | A | 4/1990 | Malabarba et al. |
| 5,534,420 | A | 7/1996 | Debono et al. |
| 5,591,714 | A | 1/1997 | Nagarajan et al. |
| 5,750,509 | A | 5/1998 | Malabarba et al. |
| 5,840,684 | A | 11/1998 | Cooper et al. |
| 5,843,889 | A | 12/1998 | Cooper et al. |
| 5,916,873 | A | 6/1999 | Cooper et al. |
| 5,919,756 | A | 7/1999 | Cooper et al. |
| 5,952,310 | A | 9/1999 | Thompson et al. |
| 5,952,466 | A | 9/1999 | Berglund et al. |
| 5,977,062 | A | 11/1999 | Cooper et al. |
| 5,977,063 | A | 11/1999 | Thompson et al. |
| 5,998,581 | A | 12/1999 | Berglund et al. |
| 6,392,012 | B1 | 5/2002 | Judice et al. |
| 6,444,786 | B1 | 9/2002 | Judice et al. |
| 6,455,669 | B1 | 9/2002 | Judice et al. |
| 6,949,681 | B2 | 9/2005 | Linsell |
| 6,962,970 | B2 | 11/2005 | Judice et al. |
| 7,101,964 | B2 | 9/2006 | Linsell |
| 2006/0241024 | A1 | 10/2006 | Linsell |

FOREIGN PATENT DOCUMENTS

| | | |
|---|---|---|
| EP | 0 802 199 A2 | 10/1997 |
| EP | 0 816 378 A1 | 1/1998 |
| WO | WO 88/06600 A1 | 9/1988 |
| WO | WO 90/11300 A1 | 10/1990 |
| WO | WO 92/17456 A1 | 10/1992 |
| WO | WO 97/28812 A2 | 8/1997 |
| WO | WO 97/34623 A1 | 9/1997 |
| WO | WO 97/38702 A1 | 10/1997 |
| WO | WO 97/40067 A1 | 10/1997 |
| WO | WO 98/21952 A1 | 5/1998 |
| WO | WO 98/52589 A1 | 11/1998 |
| WO | WO 98/52592 A1 | 11/1998 |
| WO | WO 99/42476 A1 | 8/1999 |
| WO | WO 99/56760 A1 | 11/1999 |
| WO | WO 00/04044 A1 | 1/2000 |

OTHER PUBLICATIONS

Cooper et al., "Reductive Alkylation of Glycopeptide Antibiotics:Synthesis and Antibacterial Activity", The Journal of Antibiotics, vol. 49, No. 6, pp. 575-581 (1996).

Cooper et al., "Chapter 14. Semisynthetic Glycopeptide Antibiotics", Annual Reports in Medicinal Chemistry, vol. 31, pp. 131-140 (1996).

Fukuzawa et al., "Modification of sugar part of glycopeptide antibiotic, vancomycin", Tennen Yuki Kagobutsu Toronkai Koen Yoshishua, 40th, pp. 151-156 (1998) (in Japanese with English language translation).

Ge et al., "Vancomycin Derivatives That Inhibit Peptidoglycan Biosynthesis Without Binding D-Ala-D-Ala", Science, vol. 284, pp. 507-511 (1999).

Kerns et al., "Synthesis and Antibacterial Activity of Novel Carbohydrate Modified Derivatives of the Glycopeptide Antibiotic Vancomycin", Abstracts of Papers of the 216th ACS National Meeting, Boston, MA, Aug. 23-27, 1998.

Mackay et al., "Glycopeptide Antibiotic Activity and the Possible Role of Dimerization: A Model for Biological Signaling", J. Am. Chem. Soc., vol. 116, pp. 4581-4590 (1994).

Malabarba et al., "Amides of De-Acetylglucosaminyl-Deoxy Teicoplanin Active Against Highly Glycopeptide-Resistant Enterococci", vol. 47, No. 12, pp. 1493-1506 (1994).

Malabarba et al., "Glycopeptide resistance in multiple antibiotic-resistant Gram-positive bacteria: a current challenge for novel semisynthetic glycopeptide derivatives", Eur. J. Med. Chem., vol. 32, pp. 459-478 (1997).

Malabarba et al., "New Semisynthetic Glycopeptides MDL 63,246 and MDL 63,042, and Other Amide Derivatives of Antibiotic A-40,926 against Highly Glycopeptide-resistant VanA Enterococci", The Journal of Antibiotics, vol. 48, No. 8, pp. 869-883 (1995).

Malabarba et al., "Reductive Hydrolysis of the 59,60-Amide Bond of Teicoplanin Antibiotics: A Key Step from Natural to Synthetic Glycopeptides", J. Med. Chem., vol. 37, pp. 2988-2990 (1994).

Malabarba et al., "Structural Modifications of the Active Site in Telcoplanin and Related Glycopeptldes. 1. Reductive Hydrolysis of the 1,2- and 2,3-Peptide Bonds", J. Org. Chem., vol. 61, pp. 2137-2150 (1996).

Malabarba et al., "Substitution of Amino Acids 1 and 3 in Teicoplanin Aglycon: Synthesis and Antibacterial Activity of Three First Non-natural Dalbaheptides", The Journal of Antibiotics, vol. 50, pp. 70-81 (1997).

Malabarba et al., "Synthesis and Biological Activity of Some Esters of the $N$-Acetylglucosaminyl Aglycone and of the Aglycone of Teicoplanin", The Journal of Antibiotics, vol. XL, No. 11, pp. 1572-1587 (1987).

Malabarba et al., "Synthesis and Biological Properties of $N^{63}$-Carboxamides of Teicoplanin Antibiotics. Structure-Activity Relationships", J. Med. Chem., vol. 32, pp. 2450-2460 (1989).

Nagarajan, "Structure-Activity Relationships of Vancoymycin-Type Glycopeptide Antibiotics", The Journal of Antibiotics, vol. 46, No. 8, pp. 1181-1195 (1993).

Nagarajan et al., "Synthesis and Antibacterial Activity of $N$-Acyl Vancomycins", The Journal of Antibiotics, vol. XLI, No. 10, pp. 1430-1438 (1988).

Nagarajan et al., "Synthesis and Antibacterial Evaluation of $N$-Alkyl Vancomycins", The Journal of Antibiotics, vol. XLII, No. 1, pp. 63-72 (1989).

Nicolaou et al., "Chemistry, Biology, and Medicine of the Glycopeptides Antibiotics", Angew Chem. Int. Ed., vol. 38, pp. 2096-2152 (1999).

Olsufyeva et al., "Chemical Modification of Antibiotic Eremomycin at the Asparagine Side Chain", The Journal of Antibiotics, vol. 52, No. 3, pp. 319-324 (1999).

Pavlov et al., "A New Type of Chemical Modification of Glycopeptides Antibiotics:Aminomethylated Derivatives of Eremomycin and Their Antibacterial Activity", The Journal of Antibiotics, vol. 50, No. 6, pp. 509-513 (1997).

Pavlov et al., Chemical Modification of Glycopeptide Antibiotics [VC1], Russian Journal of Bioorganic Chemistry, vol. 24, No. 9, pp. 570-587 (1998).

Pavlov et al., "Mono and Double Modified Telcoplanin Aglycon Derivatives on the Amino Acid No. 7: Structure-activity Relationship", The Journal of Antibiotics, vol. 51, No. 1, pp. 73-78 (1997).

Malabarba et al., "Structural Modifications of the Active Site in Teicoplanin and Related Glycopeptides. 1. Reductive Hydrolysis of the 1,2- and 2,3-Peptide Bonds", J. Org. Chem., vol. 61, pp. 2137-2150 (1996).

Pavlov et al., "Mono and Double Modified Teicoplanin Aglycon Derivatives on the Amino Acid No. 7; Structure-activity Relationship", The Journal of Antibiotics, vol. 51, No. 1, pp. 73-78 (1997).

Rodriguez et al., "Novel Glycopeptide Antibiotics:$N$-Alkylated Derivatives Active Against Vancomycin-Resistant Enterococci", vol. 51, No. 6, pp. 560-569 (1998).

Sharman et al., "The Roles of Dimerization and Membrane Anchoring in Activity of Glycopeptide Antibiotics against Vancomycin-Resistant Bacteria", J. Am. Chem. Soc., vol. 119, pp. 12041-12047 (1997).

Snyder et al., "Enzymatic Deacylation of Teicoplanin Followed by Reductive Alkylation:Synthesis and Antibacterial Activity of New Glycopeptides", The Journal of Antibiotics, vol. 51, No. 10, pp. 945-951 (1998).

Staroske et al., "Synthesis of Covalent Head-to-Tail Dimers of Vancomycin", Tetrahedron Letters 39, pp. 4917-4920 (1998).

Sundram et al., "Novel Vancomycin Dimers with Activity against Vancomycin-Resistant Enterococci", J. Am. Chem. Soc., vol. 118, pp. 13107-13108 (1996).

GLYCOPEPTIDE DERIVATIVES AND PHARMACEUTICAL COMPOSITIONS CONTAINING THE SAME

CROSS-REFERENCE TO RELATED APPLICATIONS

This application is a continuation of U.S. Ser. No. 11/405,234, filed Apr. 17, 2006, now U.S. Pat. No. 7,351,791, which application is a continuation of U.S. Ser. No. 11/128,901, filed May 13, 2005 (now U.S. Pat. No. 7,101,964), which application is a continuation of U.S. Ser. No. 10/092,088, filed Mar. 6, 2002 (now U.S. Pat. No. 6,962,970), which application is a continuation of U.S. Ser. No. 09/470,209, filed Dec. 22, 1999 (now U.S. Pat. No. 6,392,012), which application claims the benefit of U.S. Ser. No. 60/113,728, filed Dec. 23, 1998; U.S. Ser. No. 60/129,313, filed Apr. 14, 1999; U.S. Ser. No. 60/164,024, filed Nov. 4, 1999; and U.S. Ser. No. 60/169,978, filed Dec. 10, 1999; the disclosures of which are incorporated herein by reference in their entirety.

BACKGROUND OF THE INVENTION

1. Field of the Invention

This invention relates to novel derivatives of glycopeptide antibiotics. This invention also relates to pharmaceutical compositions containing such glycopeptide derivatives, to methods of using such glycopeptide derivatives as antibacterial agents, and to processes for preparing such glycopeptide derivatives.

2. Background

Glycopeptides are a well-known class of antibiotics produced by various microorganisms. These complex multi-ring peptide compounds are effective antibacterial agents against a majority of Gram-positive bacteria. The use of glycopeptides as antibiotics, however, has been overshadowed by the semi-synthetic penicillins, cephalosporins and lincomycin due to the higher levels of mammalian toxicity observed with the glycopeptides. In recent years, however, bacteria resistant to the penicillins, cephalosporins and the like have emerged resulting in, for example, multiple-resistant and methicillin-resistant staphylococcal (MRS) infections. Glycopeptides, such as vancomycin, are typically effective against such microorganisms and vancomycin has become the drug of last resort for MRS and other infections. The glycopeptides are believed to be effective against such resistant microorganism because they have a different mode of action than other antibiotics. In this regard, the glycopeptides are believed to selectively inhibit a different step in bacterial cell wall synthesis than the penicillin-type antibiotics.

More specifically, the cell wall of bacteria consists of linear polysaccharide chains cross-linked by short peptides. This arrangement of cross-linked polysaccharides confers mechanical support to the cell wall, thus preventing the bacteria from bursting due to its high internal osmotic pressure. During the synthesis of the bacterial cell wall, cross-linking of the polysaccharides takes place after lipid-linked disaccharide-pentapeptide constructs are incorporated into linear polysaccharide chains by a transglycolase enzyme. The subsequent cross-linking reaction is the last step in the synthesis of the cell wall and is catalyzed by an enzyme known as peptidoglycan transpeptidase.

One method by which antibacterial agents exert their antibacterial activity is by inhibiting the transglycosylase enzyme, thus interfering with the penultimate step in the synthesis of the bacterial cell wall. Although not wishing to be bound by theory, it is believed that glycopeptide antibiotics, such as vancomycin, bind with high affinity and specificity to N-terminal sequences (i.e., L-lysyl-D-alanyl-D-alanine in vancomycin-sensitive organisms) of the peptidoglycan precursors (known as lipid intermediate II). By binding to and sequestering these precursors, vancomycin prevents their utilization in cell wall biosynthesis. Thus, vancomycin inhibits the bacterial transglycosylase that is responsible for adding lipid intermediate II subunits to growing peptidoglycan chains. This step of bacterial cell wall synthesis preceeds the cross-linking transpeptidation step which is known to be inhibited by beta-lactams antibiotics. It is also believed that vancomycin inhibits transpeptidation which involves the D-alanyl-D-alanine termini. However, since this step occurs subsequent to transglycosylation, inhibition of transpeptidation is not directly observed.

A number of derivatives of vancomycin and other glycopeptides are known in the art. For example, see U.S. Pat. Nos. 4,639,433; 4,643,987; 4,497,802; 4,698,327; 5,591,714; 5,840,684; and 5,843,889. Other derivatives are disclosed in EP 0 802 199; EP 0 801 075; EP 0 667 353; WO 97/28812; WO 97/38702; WO 98/52589; WO 98/52592; and in *J. Amer. Chem. Soc.*, 1996, 118, 13107-13108; *J. Amer. Chem. Soc.*, 1997, 119, 12041-12047; and *J. Amer. Chem. Soc.*, 1994, 116, 4573-4590. The disclosures of these and other documents referred to throughout this application are incorporated herein by reference in their entirety.

A need exists, however, for glycopeptide derivatives having improved activity, selectivity and reduced mammalian toxicity. Moreover, certain microorganisms are beginning to develop resistance to vancomycin, such as vancomycin-resistant enterococci (VRE). Accordingly, it would be highly desirable to provide novel glycopeptide derivatives which are effective against a broad spectrum of bacteria, including resistant strains such as VRE. Moreover, it would be highly advantageous to provide glycopeptide derivatives having improved antibacterial activity and selectivity, and low mammalian toxicity.

SUMMARY OF THE INVENTION

The present invention provides novel derivatives of glycopeptide antibiotics having improved properties compared to the unsubstituted glycopeptide, including enhanced activity, selectivity and reduced mammalian toxicity. For example, certain vancomycin derivatives of this invention demonstrate greatly enhanced antibacterial activity compared to vancomycin itself. Such vancomycin derivatives are also highly effective against vancomycin-resistant enterococci strains while exhibiting reduced mammalian toxicity.

Accordingly, in one of its composition aspects, this invention provides a glycopeptide compound having at least one substituent of the formula:

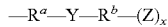

wherein
each $R^a$ is independently selected from the group consisting of alkylene, substituted alkylene, alkenylene, substituted alkenylene, alkynylene and substituted alkynylene;
each $R^b$ is independently selected from the group consisting of a covalent bond, alkylene, substituted alkylene, alkenylene, substituted alkenylene, alkynylene and substituted alkynylene, provided $R^b$ is not a covalent bond when Z is hydrogen;
each Y is independently selected from the group consisting of oxygen, sulfur, —S—S—, —NR$^c$—, —S(O)—, —SO$_2$—, —NR$^c$C(O)—, —OC(O)—, —NR$^c$SO$_2$—, —OSO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$— and —NR$^c$SO$_2$NR$^c$—;
each Z is independently selected from hydrogen, aryl, cycloalkyl, cycloalkenyl, heteroaryl and heterocyclic; P each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

x is 1 or 2;

and pharmaceutically acceptable salts thereof;

provided that:

(i) when Y is —$NR^c$—, $R^cC$ is alkyl of 1 to 4 carbon atoms, Z is hydrogen and $R^b$ is alkylene, then $R^b$ contains at least 5 carbon atoms;

(ii) when Y is —C(O)$NR^c$—, Z is hydrogen and $R^b$ is alkylene, then $R^b$ contains at least 5 carbon atoms;

(iii) when Y is sulfur, Z is hydrogen and W is alkylene, then $R^b$ contains at least 7 carbon atoms; and (iv) when Y is oxygen, Z is hydrogen and $R^b$ is alkylene, then $R^b$ contains at least 11 carbon atoms.

Preferably, the glycopeptide compound is substituted with from 1 to 3 substituents of the formula —$R^a$—Y—$R^b$—(Z)$_x$.

Each $R^a$ is preferably independently selected from alkylene having from 1 to 10 carbon atoms, more preferably, from 1 to 6 carbon atoms. In a preferred embodiment, $R^a$ is ethylene (—$CH_2CH_2$—), propylene (—$CH_2CH_2CH_2$—) or butylene (—$CH_2CH_2CH_2CH_2$—). Still more preferably, $R^a$ is ethylene or propylene.

When Z is hydrogen, $R^b$ is preferably alkylene of from 8 to 12 carbon atoms. Accordingly, in this embodiment, $R^b$ and Z preferably form an n-octyl, n-nonyl, n-decyl, n-undecyl or n-dodecyl group. When Z is other than hydrogen, $R^b$ is preferably a covalent bond or alkylene of from 1 to 10 carbon atoms. In this embodiment, $R^b$ is preferably, a covalent bond, methylene, —$(CH_2)_6$—, —$(CH_2)_7$—, —$(CH_2)_8$—, —$(CH_2)_9$— or —$(CH_2)_{10}$—.

Each Y is preferably independently selected from the group consisting of oxygen, sulfur, —S—S—, —$NR^c$—, —S(O)—, —$SO_2$—, —$NR^c(O)$—, —OC(O)—, —$NR^cSO_2$—, —C(O)$NR^c$—, —C(O)O— and —$SO_2NR^c$—. More preferably, Y is oxygen, sulfur, —$NR^c$— or —$NR^cSO_2$—.

Preferably, each Z is independently selected from hydrogen, aryl, cycloalkyl, heteroaryl and heterocyclic. More preferably, Z is hydrogen or aryl When Z is aryl, preferred Z group include phenyl, substituted phenyl, biphenyl, substituted biphenyl and terphenyl groups. Particularly preferred Z groups are phenyl, 4-isobutylphenyl, 4'-chlorobiphenyl-4-yl, 4'-trifluoromethylbiphenyl-4-yl, 4-(naphth-2-yl)phenyl, 4-(2-phenylethynyl)phenyl, 4-(3,4-dichlorobenzyloxy)-phenyl, and p-terphenyl.

Preferably, x is 1.

Particularly preferred —$R^a$—Y—$R^b$—(Z)$_x$ groups of this invention are selected from the group consisting of:

—$CH_2CH_2$—NH—$(CH_2)_9CH_3$;
—$CH_2CH_2CH_2$—NH—$(CH_2)_8CH_3$;
—$CH_2CH_2CH_2CH_2$—NH—$(CH_2)_7CH_3$;
—$CH_2CH_2$—$NHSO_2$—$(CH_2)_9CH_3$;
—$CH_2CH_2$—$NHSO_2$—$(CH_2)_{11}CH_3$;
—$CH_2CH_2$—S—$(CH_2)_8CH_3$;
—$CH_2CH_2$—S—$(CH_2)_9CH_3$;
—$CH_2CH_2$—S—$(CH_2)_{10}CH_3$;
—$CH_2CH_2CH_2$—S—$(CH_2)_8CH_3$;
—$CH_2CH_2CH_2$—S—$(CH_2)_9CH_3$;
—$CH_2CH_2CH_2$—S—$(CH_2)_3$—CH=CH—$(CH_2)_4CH_3$ (trans);
—$CH_2CH_2CH_2CH_2$—S—$(CH_2)_7CH_3$;
—$CH_2CH_2$—S(O)—$(CH_2)_9CH_3$;
—$CH_2CH_2$—S—$(CH_2)_6Ph$;
—$CH_2CH_2$—S—$(CH_2)_8Ph$;
—$CH_2CH_2CH_2$—S—$(CH_2)Ph$;
—$CH_2CH_2$—NH—$CH_2$-4-(4-Cl-Ph)-Ph;
—$CH_2CH_2$—NH—$CH_2$-4-[4-$CH_3)_2CHCH_2$-]-Ph;
—$CH_2CH_2$—NH—$CH_2$-4-(4-$CF_3$-Ph)-Ph;
—$CH_2CH_2$—S—$CH_2$-4-(4-Cl-Ph)-Ph;
—$CH_2CH_2$—S(O)—$CH_2$-4-(4-Cl-Ph)-Ph;
—$CH_2CH_2CH_2$—S—$CH_2$-4-(4-Cl-Ph)-Ph;
—$CH_2CH_2CH_2$—S(O)—$CH_2$-4-(4-Cl-Ph)-Ph;
—$CH_2CH_2CH_2$—S—$CH_2$-4-[3,4-di-Cl-Ph$CH_2$O-)-Ph;
—$CH_2CH_2$—$NHSO_2$—$CH_2$-4-[4-(4-Ph)-Ph]-Ph;
—$CH_2CH_2CH_2$—$NHSO_2$—$CH_2$-4-(4-Cl-Ph)-Ph;
—$CH_2CH_2CH_2$—$NHSO_2$—$CH_2$-4-(Ph-C≡C-)-Ph;
—$CH_2CH_2CH_2$—$NHSO_2$-4-(4-Cl-Ph)-Ph; and
—$CH_2CH_2CH_2$—$NHSO_2$-4-(naphth-2-yl)-Ph.

Other preferred —$R^a$—Y—$R^b$—(Z)$_x$ groups are shown in Tables I-VI below.

In another of its composition aspects, this invention provides a compound of formula I:

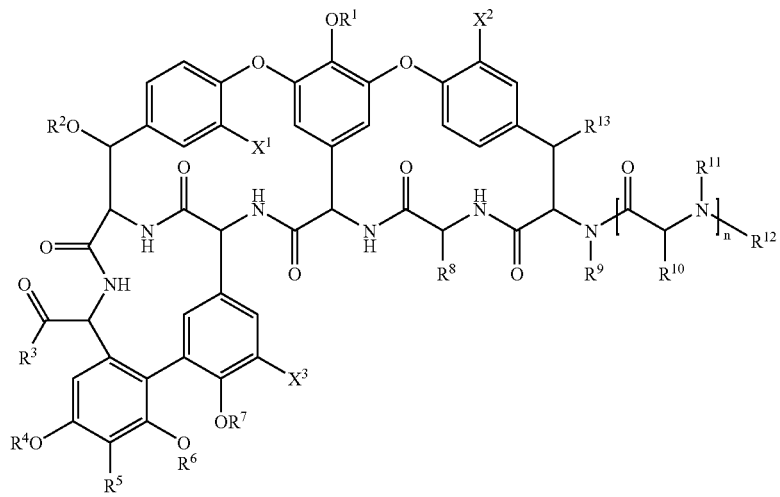

wherein $R^1$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and $-R^a-Y-R-(Z)_x$; or a saccharide group optionally substituted with $-R^a-Y-R^b-(Z)_x$;

$R^2$ is hydrogen or a saccharide group optionally substituted with $-R_a-Y-R^b-(Z)_x$;

$R^3$ is $-OR^c$, $-NR^cR^cC$, $-O-R^a-Y-R^b-(Z)_x$, $-NR^c-R^a-Y-R^b-(Z)_x$, $-NR^cCR^e$, or $-O-R^e$;

$R^4$ is selected from the group consisting of hydrogen, alkyl, substituted alkyl, alkenyl, substituted alkenyl, alkynyl, substituted alkynyl, $-R^a-Y-R^b-(Z)_x$, $-C(O)R^d$ and a saccharide group optionally substituted with $-R^a-Y-R^b-(Z)_x$;

$R^5$ is selected from the group consisting of hydrogen, halo, $-CH(R^c)-NR^cR^c$, $-CH(R^c)-NR^cR^c$ and $-CH(R^c)-NR^c-R^a-Y-R^b-(Z)_x$;

$R^6$ is selected from the group consisting of hydrogen, alkyl, substituted alkyl, alkenyl, substituted alkenyl, alkynyl, substituted alkynyl, $-R^a-Y-R^b-(Z)_x$, $-C(O)R^d$ and a saccharide group optionally substituted with $-NR-R^a-Y-R^b-(Z)_x$, or $R^5$ and $R^6$ can be joined, together with the atoms to which they are attached, form a heterocyclic ring optionally substituted with $-NR^c-R^a-Y-R^b-(Z)_x$;

$R^7$ is selected from the group consisting of hydrogen, alkyl, substituted alkyl, alkenyl, substituted alkenyl, alkynyl, substituted alkynyl, $-R^a-Y-R^b-(Z)_x$, and $-C(O)R^d$;

$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or $R^8$ and $R^{10}$ are joined to form $-Ar^1-O-Ar^2-$, where $Ar^1$ and $Ar^2$ are independently arylene or heteroarylene; $R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or $R^{10}$ and $R^{11}$ are joined, together with the carbon and nitrogen atoms to which they are attached, to form a heterocyclic ring;

$R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, $-C(O)R^d$, $-C(NH)R^d$, $-C(O)NR^cR^c$, $-C(O)OR^d$, $-C(NH)NR^cR^c$ and $-R^a-Y-R^b-(Z)_x$, or $R^{11}$ and $R^{12}$ are joined, together with the nitrogen atom to which they are attached, to form a heterocyclic ring;

$R^{13}$ is selected from the group consisting of hydrogen or $-OR^{14}$;

$R^{14}$ is selected from hydrogen, $-C(O)R^d$ and a saccharide group;

each $R^a$ is independently selected from the group consisting of alkylene, substituted alkylene, alkenylene, substituted alkenylene, alkynylene and substituted alkynylene;

each $R^b$ is independently selected from the group consisting of a covalent bond, alkylene, substituted alkylene, alkenylene, substituted alkenylene, alkynylene and substituted alkynylene, provided $R^b$ is not a covalent bond when Z is hydrogen;

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and $-C(O)R^d$;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^e$ is a saccharide group;

$X^1$, $X^2$ and $X^3$ are independently selected from hydrogen or chloro;

each Y is independently selected from the group consisting of oxygen, sulfur, $-S-S-$, $-NR^c-$, $-S(O)-$, $-SO_2-$, $-NR^cC(O)-$, $-OSO_2-$, $-OC(O)-$, $-NR^cSO_2-$, $-C(O)NR^c-$, $-C(O)O-$, $-SO_2NR^c-$, $-SO_2O-$, $-P(O)(OR^c)O-$, $-P(O)(OR^c)NR^c-$, $-OP(O)(OR^c)O-$, $-OP(O)(OR^c)NR^c-$, $-OC(O)O-$, $-NR^cC(O)O-$, $-NR^c(O)NR^c-$, $OC(O)NR^c-$ and $-NR^cSO_2NR^c-$;

each Z is independently selected from hydrogen, aryl, cycloalkyl, cycloalkenyl, heteroaryl and heterocyclic;

n is 0, 1 or 2;

x is 1 or 2;

and pharmaceutically acceptable salts, stereoisomers and prodrugs thereof;

provided that at least one of $R^1$, $R^2$, $R^3$, $R^4$, $R^5$, $R^6$, $R^7$ or $R^{12}$ has a substitutent of the formula $-R^a-Y-R^b-(Z)_x$;

and further provided that:

(i) when Y is $-NR^c-$, $R^cC$ is alkyl of 1 to 4 carbon atoms, Z is hydrogen and $R^b$ is alkylene, then $R^b$ contains at least 5 carbon atoms;

(ii) when Y is $-C(O)NR^c-$, Z is hydrogen and $R^b$ is alkylene, then $R^b$ contains at least 5 carbon atoms;

(iii) when Y is sulfur, Z is hydrogen and $R^b$ is alkylene, then $R^b$ contains at least 7 carbon atoms; and (iv) when Y is oxygen, Z is hydrogen and $R^b$ is alkylene, then $R^b$ contains at least 11 carbon atoms.

Preferably, $R^1$ is a saccharide group optionally substituted with $-R^a-Y-R-(Z)_x$. More preferably, $R^1$ is a saccharide group of the formula:

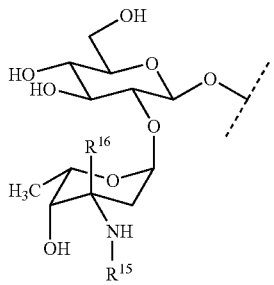

wherein
$R^{15}$ is —R—Y—$R^b$—(Z)$_x$, where $R^a$, $R^b$, Y, Z and x are as defined herein; and $R^{16}$ is hydrogen or methyl Preferably, $R^2$ is hydrogen.

$R^3$ is preferably —$OR^c$ or —$NR^cR^c$; more preferably $R^3$ is —OH. Particularly preferred $R^3$ groups are those shown in Tables I-IV as $R^{22}$.

Preferably, $R^4$, $R^6$ and $R^7$ are each independently selected from hydrogen of —C(O)$R^d$. More preferably, $R^4$, $R^6$ and $R^7$ are each hydrogen.

$R^5$ is preferably hydrogen, —$CH_2$—NHR$^c$, —$CH_2$—NR$^c$R$^e$ and —$CH_2$—NH—$R^a$—Y—$R^b$—(Z)$_x$, where $R^a$, $R^b$, $R^c$C, $R^e$, Y, Z and x are as defined herein. Particularly preferred $R^5$ groups include hydrogen, —$CH_2$—N—(N—$CH_3$-D-glucamine); —$CH_2$—NH—$CH_2CH_2$—NH—$(CH_2)_9$$CH_3$; —$CH_2$—NH—$CH_2CH_2$—NH—$(CH_2)_{11}CH_3$; —$CH_2$—NH—$(CH_2)_5$—COOH; and —$CH_2$—N-(2-amino-2-deoxygluconic acid). Other preferred $R^5$ groups are those shown in Table III as $R^{23}$.

Preferably, $R^8$ is —$CH_2C(O)NH_2$, —$CH_2COOH$, benzyl, 4-hydroxyphenyl or 3-chloro-4-hydroxyphenyl. More preferably, $R^8$ is —$CH_2C(O)NH_2$.

$R^9$ is preferably hydrogen or alkyl. More preferably, $R^9$ is hydrogen.

$R^{10}$ is preferably alkyl or substituted alkyl. More preferably, $R^{10}$ is the side-chain of a naturally occurring amino acid. Still more preferably, $R^{10}$ is isobutyl.

$R^{11}$ is preferably hydrogen or alkyl More preferably, $R^{11}$ is hydrogen or methyl $R^{12}$ is preferably hydrogen, alkyl, substituted alkyl or —C(O)$R^d$. More preferably, $R^{12}$ is hydrogen or —$CH_2COOH$. Other preferred $R^{12}$ groups are those shown in Table II as $R^{27}$.

$X^1$ and $X^2$ are preferably chloro V is preferably hydrogen.

Preferably, n is 0 or 1. More preferably, n is 1.

In still another of its composition aspects, this invention provides a compound of formula II:

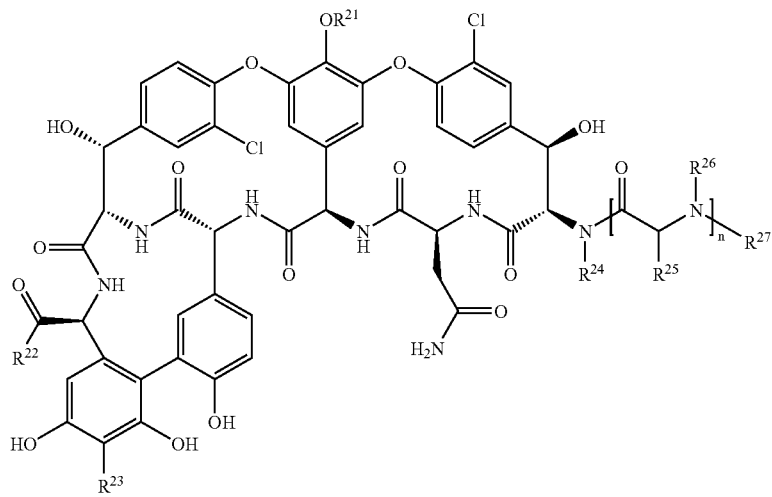

II wherein
$R^{21}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$(Z)$_x$; or a saccharide group optionally substituted with —$R^a$—Y—$R^b$—(Z)$_x$;

$R^{22}$ is —$OR^c$, —$NR^cR^c$, —O—$R^a$—Y—$R^b$—(Z)$_x$ or —$NR^c$—$R^a$—Y—$R^b$—(Z)$_x$;

$R^{23}$ is selected from the group consisting of hydrogen, halo, —CH(R)—$NR^cR^c$, —CH($R^c$)—$R^e$ and —CH($R^c$)—$NR^c$—$R^a$—Y—$R^b$—(Z)$_x$;

$R^{24}$ is selected from the group consisting of hydrogen and lower alkyl;

$R^{25}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^{26}$ is selected from the group consisting of hydrogen and lower alkyl; or $R^{25}$ and $R^{26}$ are joined, together with the carbon and nitrogen atoms to which they are attached, to form a heterocyclic ring;

$R^{27}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)R$^d$, —C(NH)R$^d$, —C(O)NR$^c$R$^c$, —C(O)OR$^d$, —C(NH)NR$^c$R$^c$ and —R$^a$—Y—R—(Z)$^x$, or R$^{26}$ and R$^{27}$ are joined, together with the nitrogen atom to which they are attached, to form a heterocyclic ring;

each R$^a$ is independently selected from the group consisting of alkylene, substituted alkylene, alkenylene, substituted alkenylene, alkynylene and substituted alkynylene;

each R$^b$ is independently selected from the group consisting of a covalent bond, alkylene, substituted alkylene, alkenylene, substituted alkenylene, alkynylene and substituted alkynylene, provided R$^b$ is not a covalent bond when Z is hydrogen;

each R$^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$;

each R$^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R$^e$ is an aminosaccharide group;

each Y is independently selected from the group consisting of oxygen, sulfur, —S—S—, —NR$^c$—S(O)—, —SO$_2$—, —NR$^c$C(O)—, —OSO$_2$—, —OC(O)—, —NR$^c$SO$_2$—, —C(O)NR$^c$—, —C(O)O—, —SO$_2$NR$^c$—, —SO$_2$O—, —P(O)(OR$^c$)O—, —P(O)(OR)NR$^c$—, —OP(O)(OR$^c$)O—, —OP(O)(OR$^c$)NR$^c$—, —OC(O)O—, —NR$^c$C(O)O—, —NR$^c$(O)NR$^c$—, —OC(O)NR$^c$— and —NR$^c$SO$_2$NR$^c$—;

each Z is independently selected from hydrogen, aryl, cycloalkyl, cycloalkenyl, heteroaryl and heterocyclic;

n is 0, 1 or 2;

x is 1 or 2;

and pharmaceutically acceptable salts, stereoisomers and prodrugs thereof;

provided that at least one of $R^{21}$, $R^{22}$, $R^{23}$ or $R^{27}$ has a substituent of the formula —R—Y—R$^b$—(Z)$_x$;

and further provided that:

(i) when Y is —NR$^c$—, R$^c$ is alkyl of 1 to 4 carbon atoms, Z is hydrogen and R$^b$ is alkylene, then R$^b$ contains at least 5 carbon atoms;

(ii) when Y is —C(O)NR$^c$—, Z is hydrogen and R$^b$ is alkylene, then R$^b$ contains at least 5 carbon atoms;

(iii) when Y is sulfur, Z is hydrogen and R$^b$ is alkylene, then R$^b$ contains at least 7 carbon atoms; and (iv) when Y is oxygen, Z is hydrogen and R$^b$ is alkylene, then R$^b$ contains at least 11 carbon atoms.

Preferably, $R^{21}$ is a saccharide group of the formula:

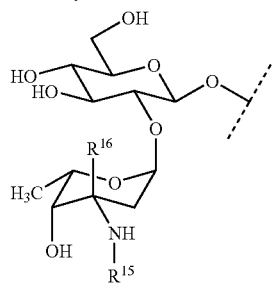

wherein $R^{15}$ is —R—Y—R$^b$—(Z)$_x$, where R$^a$, R$^b$, Y, Z and x are as defined herein; and $R^{16}$ is hydrogen or methyl.

$R^{22}$ is preferably —OR$^c$ or —NR$^c$R$^c$; more preferably $R^{22}$ is —OH. Particularly preferred $R^{22}$ groups are those shown in Tables I-IV.

$R^{23}$ is preferably hydrogen, —CH$_2$—R$^e$, —CH, —NHR$^c$ and —CH$_2$—NH—R$^a$—Y—R$^b$—(Z)$_x$, where R$^a$, R$^b$, R$^c$C, R$^e$, Y, Z and x are as defined herein. Particularly preferred $R^{23}$ groups include hydrogen, —CH$_2$—N—(N—CH$_3$-D-glucamine); —CH$_2$—NH—CH$_2$CH$_2$—NH—(CH$_2$)$_9$CH$_3$; —CH$_2$—NH—CH$_2$CH$_2$—NH—(CH$_2$)$_{11}$CH$_3$; —CH$_2$—NH—(CH$_2$)$_5$—COOH; and —CH$_2$—N-(2-amino-2-deoxygluconic acid). Other preferred $R^{23}$ groups are shown in Table III.

$R^{24}$ is preferably hydrogen or alkyl. More preferably, $R^{24}$ is hydrogen.

$R^{25}$ is preferably alkyl or substituted alkyl. More preferably, $R^{25}$ is the side-chain of a naturally occurring amino acid. Still more preferably, $R^{25}$ is isobutyl.

$R^{26}$ is preferably hydrogen or alkyl. More preferably, $R^{26}$ is hydrogen or methyl.

$R^{27}$ is preferably hydrogen, alkyl, substituted alkyl or —C(O)R$^d$. More preferably, $R^{27}$ is hydrogen or —CH$_2$COOH. Other preferred $R^{27}$ groups are those shown in Table II.

In yet another of its composition aspects, this invention provides a pharmaceutical composition comprising a pharmaceutically-acceptable carrier and a therapeutically effective amount of a glycopeptide compound having at least one substituent of the formula:

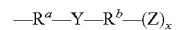

wherein R$^a$, R$^b$, Y, Z and x are as defined herein.

Additionally, this invention provides a pharmaceutical composition comprising a pharmaceutically-acceptable carrier and a therapeutically effective amount of a compound of formula I or II.

The compounds of this invention are highly effective antibacterial agents. Accordingly, in one of its method aspects, this invention provides a method of treating a mammal having a bacterial disease, the method comprising administering to the mammal a therapeutically effective amount of a glycopeptide compound having at least one substituent of the formula:

wherein R$^a$, R$^b$, Y, Z and x are as defined herein.

Additionally, this invention provides a method of treating a mammal having a bacterial disease, the method comprising administering to the mammal a therapeutically effective amount of a compound of formula I or II.

This invention also provides processes for preparing glycopeptide derivatives, which processes are described further herein below.

In another of its aspects, this invention is directed to the use of a glycopeptide derivative of formula I or formula II in the manufacture of a formulation or medicament for a medicinal treatment. Preferably, the formulation or medicament is used as an antibacterial agent.

Preferred compounds of this invention are those set forth in the following tables as formulas III, IV, V, VI, VII and VIII, and pharmaceutically-acceptable salts thereof:

TABLE I

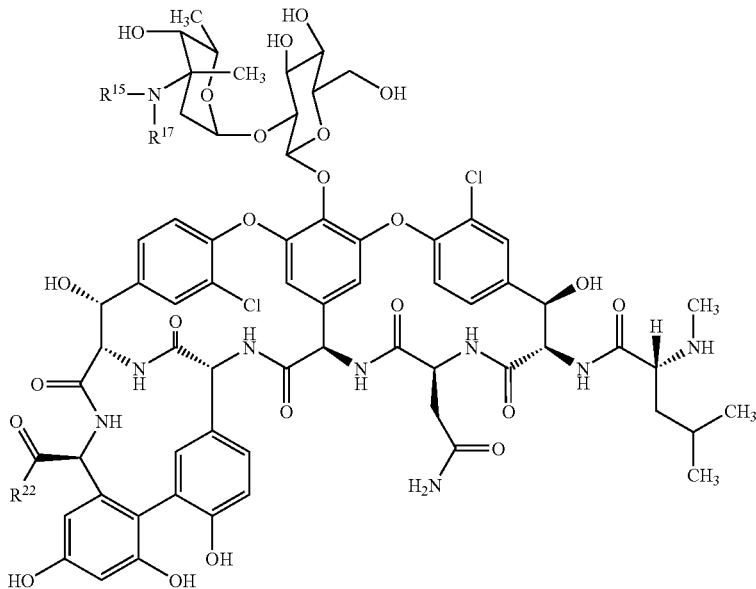

III

| No. | $R^{15}$ ($R^{17}$ = H, unless otherwise indicated) | $R^{22}$ |
|---|---|---|
| 1 | —CH$_2$CH$_2$—NH—(CH$_2$)$_9$CH$_3$ | —OH |
| 2 | —CH$_2$CH$_2$—N[(CH$_2$)$_9$CH$_3$]$_2$ | —OH |
| 3 | —CH$_2$CH$_2$—NH—(CH$_2$)$_7$CH$_3$ | —OH |
| 4 | —CH$_2$CH$_2$—NH—(CH$_2$)$_5$CH$_3$ | —OH |
| 5 | —CH$_2$CH$_2$—NH—CH$_2$Ph | —OH |
| 6 | —CH$_2$CH$_2$—NH—CH$_2$-4-Ph-Ph | —OH |
| 7 | —CH$_2$CH$_2$—NH—CH$_2$-4-(4-Cl-Ph)-Ph | —OH |
| 8 | —CH$_2$CH$_2$—NH—(CH$_2$)$_8$CH$_3$ | —OH |
| 9 | —CH$_2$CH$_2$—NH—CH$_2$-cyclohexyl | —OH |
| 10 | —CH$_2$CH$_2$CH$_2$—NH—(CH$_2$)$_8$CH$_3$ | —OH |
| 11 | —CH$_2$CH$_2$CH$_2$CH$_2$—NH—(CH$_2$)$_7$CH$_3$ | —OH |
| 12 | —CH$_2$CH$_2$CH$_2$CH$_2$CH$_2$—NH—(CH$_2$)$_6$CH$_3$ | —OH |
| 13 | —CH$_2$CH$_2$—N(CH$_3$)—(CH$_2$)$_9$CH$_3$ | —OH |
| 14 | —CH$_2$CH$_2$—NH—(CH$_2$)$_3$CH=CH(CH$_2$)$_4$CH$_3$ (trans) | —OH |
| 15 | —CH$_2$CH$_2$—NH—CH$_2$CH=C(CH$_3$)(CH$_2$)$_2$—CH=C(CH$_3$)$_2$ (trans, trans) | —OH |
| 16 | —CH$_2$CH$_2$—NH—(CH$_2$)$_8$CH(OH)CH$_3$ | —OH |
| 17 | —CH$_2$CH$_2$—NH—(CH$_2$)$_8$CH=CH$_2$ | —OH |
| 18 | —CH$_2$CH$_2$—NH—CH$_2$-cyclopropyl | —OH |
| 19 | —CH$_2$CH$_2$—NH—(CH$_2$)$_9$CH$_3$ | —NH(CH$_2$)$_3$N(CH$_3$)$_2$ |
| 20 | —CH$_2$CH$_2$—N[(CH$_2$)$_9$CH$_3$]$_2$ | —NH(CH$_2$)$_3$N(CH$_3$)$_2$ |
| 21 | —CH$_2$CH$_2$—NH—(CH$_2$)$_9$CH$_3$ | —N-(D-glucosamine) |
| 22 | —CH$_2$CH$_2$—NH—(CH$_2$)$_9$CH$_3$ | —NHCH(COOH)CH$_2$COOH |
| 23 | —CH$_2$CH$_2$—NH—CH$_2$-4-(4-Cl-Ph)-Ph | —N-(D-glucosamine) |
| 24 | —CH$_2$CH$_2$—NH—(CH$_2$)$_8$CH$_3$ | —N-(D-glucosamine) |
| 25 | —CH$_2$CH$_2$—NH—CH$_2$CH=C(CH$_3$)(CH$_2$)$_2$—CH=C(CH$_3$)$_2$ (trans, trans) | —N-(D-glucosamine) |
| 26 | —CH$_2$CH$_2$—NH—(CH$_2$)$_9$CH$_3$ | —NHCH(CO$_2$CH$_3$)CH$_2$CO$_2$CH$_3$ |
| 27 | —CH$_2$CH$_2$—NH—(CH$_2$)$_8$CH(OH)CH$_3$ | —NHCH(COOH)CH$_2$COOH |
| 28 | —CH$_2$CH$_2$—NHC(O)—(CH$_2$)$_6$CH(CH$_3$)CH$_3$ | —OH |
| 29 | —CH$_2$CH$_2$—NHC(O)—(CH$_2$)$_8$CH$_3$ | —OH |
| 30 | —CH$_2$CH$_2$—OC(O)—(CH$_2$)$_8$CH$_3$ | —OH |
| 31 | —CH$_2$—C(O)O—(CH$_2$)$_9$CH$_3$ | —OH |
| 32 | —CH$_2$—C(O)NH—(CH$_2$)$_9$CH$_3$ | —OH |
| 33 | —CH$_2$—C(O)O—(CH$_2$)$_7$CH$_3$ | —OH |
| 34 | —CH$_2$CH$_2$—NHSO$_2$—(CH$_2$)$_7$CH$_3$ | —OH |
| 35 | —CH$_2$CH$_2$—OSO$_2$—(CH$_2$)$_7$CH$_3$ | —OH |
| 36 | —CH$_2$CH$_2$—S—(CH$_2$)$_9$CH$_3$ | —OH |
| 37 | —CH$_2$CH$_2$—NHC(O)—(CH$_2$)$_6$CH$_3$ | —OH |
| 38 | —CH$_2$CH$_2$—NHC(O)—(CH$_2$)$_7$CH$_3$ | —OH |
| 39 | —CH$_2$CH$_2$—NHC(O)—(CH$_2$)$_9$CH$_3$ | —OH |
| 40 | —CH$_2$—C(O)NH—(CH$_2$)$_6$CH$_3$ | —OH |
| 41 | —CH$_2$—C(O)NH—(CH$_2$)$_7$CH$_3$ | —OH |
| 42 | —CH$_2$—C(O)NH—(CH$_2$)$_8$CH$_3$ | —OH |
| 43 | —CH$_2$CH$_2$—NH—(CH$_2$)$_9$CH$_3$ | —NH(CH$_2$)$_3$-morpholin-4-yl |
| 44 | —CH$_2$CH$_2$—NH—(CH$_2$)$_9$CH$_3$ | —NH(CH$_2$)$_3$—NH—(CH$_2$)$_2$CH$_3$ |

TABLE I-continued

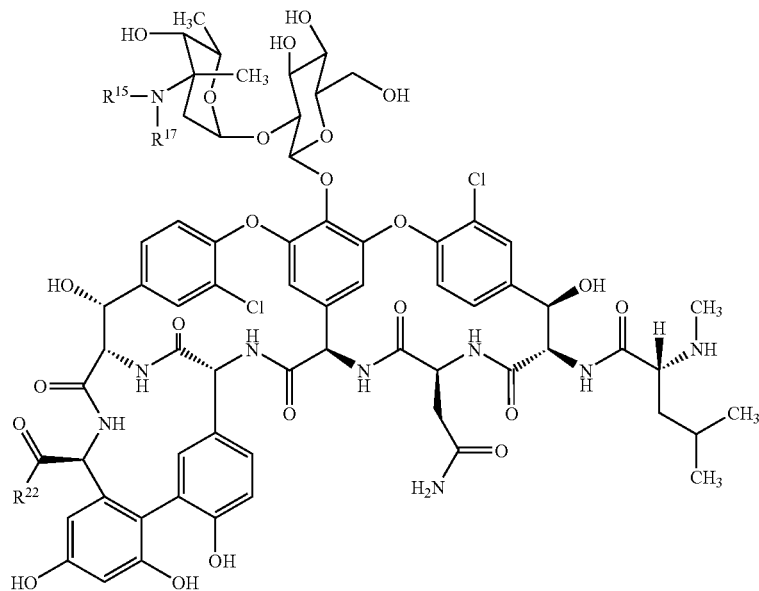

| No. | $R^{15}$ ($R^{17}$ = H, unless otherwise indicated) | $R^{22}$ |
|---|---|---|
| 45 | —CH$_2$CH$_2$—NH—(CH$_2$)$_9$CH$_3$ | —NH(CH$_2$)$_2$-piperidin-1-yl |
| 46 | —CH$_2$CH$_2$—NH—(CH$_2$)$_9$CH$_3$ | —NH(CH$_2$)$_4$NHC(N)NH$_2$ |
| 47 | —CH$_2$CH$_2$—NH—(CH$_2$)$_9$CH$_3$ | —NH(CH$_2$)$_2$—N$^+$(CH$_3$)$_3$ |
| 48 | —CH$_2$CH$_2$—NH—(CH$_2$)$_9$CH$_3$ | —NHCH(COOH)(CH$_2$)$_3$NHC(N)NH$_2$ |
| 49 | —CH$_2$CH$_2$—NH—(CH$_2$)$_9$CH$_3$ | —NH[(CH$_2$)$_3$NH—]$_3$H |
| 50 | —CH$_2$CH$_2$—NH—(CH$_2$)$_9$CH$_3$ | —N[(CH$_2$)$_3$N(CH$_3$)$_2$]$_2$ |
| 51 | —CH$_2$CH$_2$—NH—(CH$_2$)$_9$CH$_3$ | —NH(CH$_2$)$_3$-imidiazol-1-yl |
| 52 | —CH$_2$CH$_2$—NH—(CH$_2$)$_9$CH$_3$ | —NHCH$_2$-4-pyridyl |
| 53 | —CH$_2$CH$_2$—NH—(CH$_2$)$_9$CH$_3$ | —NH(CH$_2$)$_3$CH$_3$ |
| 54 | —CH$_2$CH$_2$—NH—(CH$_2$)$_9$CH$_3$ | —NH(CH$_2$)$_2$OH |
| 55 | —CH$_2$CH$_2$—NH—(CH$_2$)$_9$CH$_3$ | —NH(CH$_2$)$_5$OH |
| 56 | —CH$_2$CH$_2$—NH—(CH$_2$)$_9$CH$_3$ | —NH(CH$_2$)$_2$OCH$_3$ |
| 57 | —CH$_2$CH$_2$—NH—(CH$_2$)$_9$CH$_3$ | —NHCH$_2$-tetrahydrofuran-2-yl |
| 58 | —CH$_2$CH$_2$—NH—(CH$_2$)$_9$CH$_3$ | —N[(CH$_2$)$_2$OH]$_2$ |
| 59 | —CH$_2$CH$_2$—NH—(CH$_2$)$_9$CH$_3$ | —NH(CH$_2$)$_2$N[(CH$_2$)$_2$OH]$_2$ |
| 60 | —CH$_2$CH$_2$—NH—(CH$_2$)$_9$CH$_3$ | —N-(glucamine) |
| 61 | —CH$_2$CH$_2$—NH—(CH$_2$)$_9$CH$_3$ | —NHCH$_2$COOH |
| 62 | —CH$_2$CH$_2$—NH—(CH$_2$)$_9$CH$_3$ | —NHCH(COOH)CH$_2$OH |
| 63 | —CH$_2$CH$_2$—NH—(CH$_2$)$_9$CH$_3$ | —NH(CH$_2$)$_2$COOH |
| 64 | —CH$_2$CH$_2$—NH—(CH$_2$)$_9$CH$_3$ | —NH(CH$_2$)$_3$SO$_3$H |
| 65 | —CH$_2$CH$_2$—NH—(CH$_2$)$_9$CH$_3$ | —NHCH(COOH)(CH$_2$)$_3$COOH |
| 66 | —CH$_2$CH$_2$—NH—(CH$_2$)$_9$CH$_3$ | —NHCH(COOH)(CH$_2$)$_2$NH$_2$ |
| 67 | —CH$_2$CH$_2$—NH—(CH$_2$)$_9$CH$_3$ | —NHCH(COOH)(CH$_2$)$_3$NH$_2$ |
| 68 | —CH$_2$CH$_2$—NH—(CH$_2$)$_9$CH$_3$ | —NHCH(COOH)CH$_2$CO$_2$(CH$_2$)$_3$—N$^+$(CH$_3$)$_3$ |
| 69 | —CH$_2$CH$_2$—NH—(CH$_2$)$_9$CH$_3$ | —NHCH(COOH)CH$_2$CO$_2$—(CH$_2$)$_2$C(O)N(CH$_3$)$_2$ |
| 70 | —CH$_2$CH$_2$—NH—(CH$_2$)$_9$CH$_3$ | —NHCH(COOH)CH$_2$CO$_2$—(CH$_2$)$_3$-morpholin-4-yl |
| 71 | —CH$_2$CH$_2$—NH—(CH$_2$)$_9$CH$_3$ | —NHCH(COOH)CH$_2$CO$_2$(CH$_2$)$_2$OC(O)C(CH$_3$)$_3$ |
| 72 | —CH$_2$CH$_2$—NH—(CH$_2$)$_9$CH$_3$ | —NHCH(CH$_2$COOH)CO$_2$(CH$_2$)$_3$—N$^+$(CH$_3$)$_3$ |
| 73 | —CH$_2$CH$_2$—NH—(CH$_2$)$_9$CH$_3$ | —NHCH(CH$_2$COOH)CO$_2$(CH$_2$)$_2$C(O)N(CH$_3$)$_2$ |
| 74 | —CH$_2$CH$_2$—NH—(CH$_2$)$_9$CH$_3$ | —NHCH(CH$_2$COOH)CO$_2$(CH$_2$)$_3$-morpholin-4-yl |
| 75 | —CH$_2$CH$_2$—NH—(CH$_2$)$_9$CH$_3$ | —NHCH(CH$_2$COOH)CO$_2$(CH$_2$)$_2$OC(O)C(CH$_3$)$_3$ |
| 76 | —CH$_2$CH$_2$—NH—(CH$_2$)$_6$Ph | —OH |
| 77 | —CH$_2$CH$_2$—NH—(CH$_2$)$_8$Ph | —OH |
| 78 | —CH$_2$CH$_2$—NH—CH$_2$Ph | —OH |
| 79 | —CH$_2$CH$_2$—NH—CH$_2$-4-Cl-Ph | —OH |
| 80 | —CH$_2$CH$_2$—NH—CH$_2$-4-[CH$_3$(CH$_2$)$_2$O-]Ph | —OH |
| 81 | —CH$_2$CH$_2$—NH—CH$_2$-4-[CH$_3$(CH$_2$)$_4$O-]Ph | —OH |
| 82 | —CH$_2$CH$_2$—NH—CH$_2$-4-[CH$_3$(CH$_2$)$_6$O-]Ph | —OH |
| 83 | —CH$_2$CH$_2$—NH—CH$_2$-4-[CH$_3$(CH$_2$)$_8$O-]Ph | —OH |
| 84 | —CH$_2$CH$_2$—NH—CH$_2$-4-[CH$_3$(CH$_2$)$_2$-]Ph | —OH |
| 85 | —CH$_2$CH$_2$—NH—CH$_2$-4-[CH$_3$(CH$_2$)$_3$-]Ph | —OH |
| 86 | —CH$_2$CH$_2$—NH—CH$_2$-4-[CH$_3$(CH$_2$)$_4$-]Ph | —OH |
| 87 | —CH$_2$CH$_2$—NH—CH$_2$-4-(PhO-)Ph | —OH |
| 88 | —CH$_2$CH$_2$—NH—CH$_2$-4-(PhS-)Ph | —OH |
| 89 | —CH$_2$CH$_2$—NH—CH$_2$-3-(PhO-)Ph | —OH |
| 90 | —CH$_2$CH$_2$—NH—CH$_2$-4-(cyclohexyl-)Ph | —OH |

TABLE I-continued

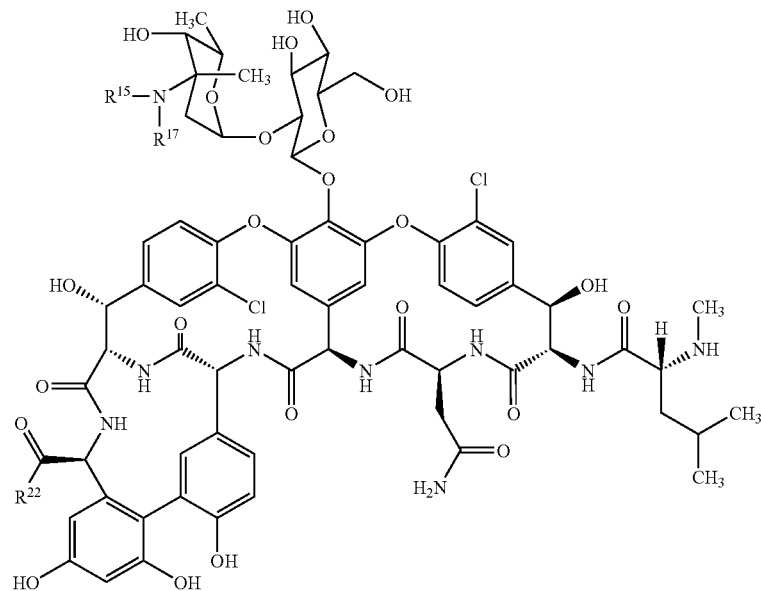

III

| No. | R[15] (R[17] = H, unless otherwise indicated) | R[22] |
|---|---|---|
| 91 | —CH$_2$CH$_2$—NH—CH$_2$-4-{4-[CH$_3$(CH$_2$)$_4$O-]-Ph}-Ph | —OH |
| 92 | —CH$_2$CH$_2$—NH—CH$_2$-4-CF$_3$-Ph | —OH |
| 93 | —CH$_2$CH$_2$—NH—CH$_2$-4-(PhCH$_2$O-)Ph | —OH |
| 94 | —CH$_2$CH$_2$—NH—CH$_2$-4-(4-CH$_3$-PhCH$_2$O-)Ph | —OH |
| 95 | —CH$_2$CH$_2$—NH—(CH$_2$)$_7$CH(CH$_3$)$_2$ | —OH |
| 96 | —(CH$_2$)$_5$—NH—(CH$_2$)$_6$CH$_3$ | —OH |
| 97 | —(CH$_2$)$_3$—NH—(CH$_2$)$_9$CH$_3$ | —OH |
| 98 | —(CH$_2$)$_4$—NH—(CH$_2$)$_9$CH$_3$ | —OH |
| 99 | —(CH$_2$)$_5$—NH—(CH$_2$)$_9$CH$_3$ | —OH |
| 100 | —CH$_2$CH$_2$—NH—(CH$_2$)$_7$CH$_3$ | —OH |
| 101 | —CH$_2$CH$_2$—NH—CH$_2$-cyclohexyl | —OH |
| 102 | —CH$_2$CH$_2$—S—(CH$_2$)$_7$CH$_3$ | —OH |
| 103 | —CH$_2$CH$_2$—OC(O)—(CH$_2$)$_6$CH$_3$ | —OH |
| 104 | —CH$_2$CH$_2$—NHSO$_2$—(CH$_2$)$_9$CH$_3$ | —OH |
| 105 | —CH$_2$CH$_2$—OSO$_2$—(CH$_2$)$_9$CH$_3$ | —OH |
| 106 | —CH$_2$CH$_2$—NH—CH$_2$CH=CH—CH=CH(CH$_2$)$_4$CH$_3$ (trans, trans) | —OH |
| 107 | —CH$_2$CH$_2$—NH—CH$_2$CH=CH—CH=CH(CH$_2$)$_3$CH$_3$ (trans, trans) | —OH |
| 108 | —CH$_2$CH$_2$—NH—CH$_2$CH=CH—CH=CHCH$_2$CH$_3$ (trans, trans) | —OH |
| 109 | —CH$_2$CH$_2$—NH—CH$_2$CH=CH—CH$_2$CH$_2$CH=CHCH$_2$CH$_3$ (trans, trans) | —OH |
| 110 | —CH$_2$CH$_2$—NH—CH$_2$-4-Cl-Ph | —OH |
| 111 | —CH$_2$CH$_2$—NH—CH$_2$-4-(PhCH$_2$O-)Ph | —OH |
| 112 | —CH$_2$CH$_2$—NH—CH$_2$-4-(4-CH$_3$-PhCH$_2$O-)Ph | —OH |
| 113 | —CH$_2$CH$_2$—NH—CH$_2$-4-(4-Cl-PhCH$_2$O-)Ph | —OH |
| 114 | —CH$_2$CH$_2$—NH—CH$_2$-4-[CH$_3$(CH$_2$)$_2$O-]Ph | —OH |
| 115 | —CH$_2$CH$_2$—NH—CH$_2$-4-[CH$_3$(CH$_2$)$_4$O-]Ph | —OH |
| 116 | —CH$_2$CH$_2$—NH—CH$_2$-4-[CH$_3$(CH$_2$)$_6$O-]Ph | —OH |
| 117 | —CH$_2$CH$_2$—NH—CH$_2$-4-[CH$_3$(CH$_2$)$_8$O-]Ph | —OH |
| 118 | —CH$_2$CH$_2$—NH—CH$_2$-4-[(CH$_3$)$_2$CHCH$_2$-]Ph | —OH |
| 119 | —CH$_2$CH$_2$—NH—CH$_2$-4-(Ph-S-)Ph | —OH |
| 120 | —CH$_2$CH$_2$—NH—CH$_2$-4-(4-CF$_3$-Ph)-Ph | —OH |
| 121 | —CH$_2$CH$_2$—NH—CH$_2$-4-{4-[CH$_3$(CH$_2$)$_4$O-]-Ph}-Ph | —OH |
| 122 | —CH$_2$CH$_2$—NH—(CH$_2$)$_6$Ph | —OH |
| 123 | —CH$_2$CH$_2$—NH—(CH$_2$)$_8$Ph | —OH |
| 124 | —CH$_2$CH$_2$—NH—(CH$_2$)$_9$CH$_3$<br>R[17] = —CH$_2$COOH | —OH |
| 125 | —CH$_2$CH$_2$—NH—(CH$_2$)$_9$CH$_3$<br>R[17] = —CH$_2$[CH(OH)]$_4$COOH | —OH |
| 126 | —CH$_2$CH$_2$—NH—(CH$_2$)$_9$CH$_3$<br>R[17] = —CH$_2$-(imidazol-4-yl) | —OH |
| 127 | —CH$_2$CH$_2$—NH—(CH$_2$)$_9$CH$_3$ | —NH(CH$_2$)$_3$CH$_3$ |
| 128 | —CH$_2$CH$_2$—NH—(CH$_2$)$_9$CH$_3$ | —NHCH(COOH)CH$_2$OH |
| 129 | —CH$_2$CH$_2$—NH—CH$_2$CH$_2$-(cyclopropyl) | —OH |

TABLE I-continued

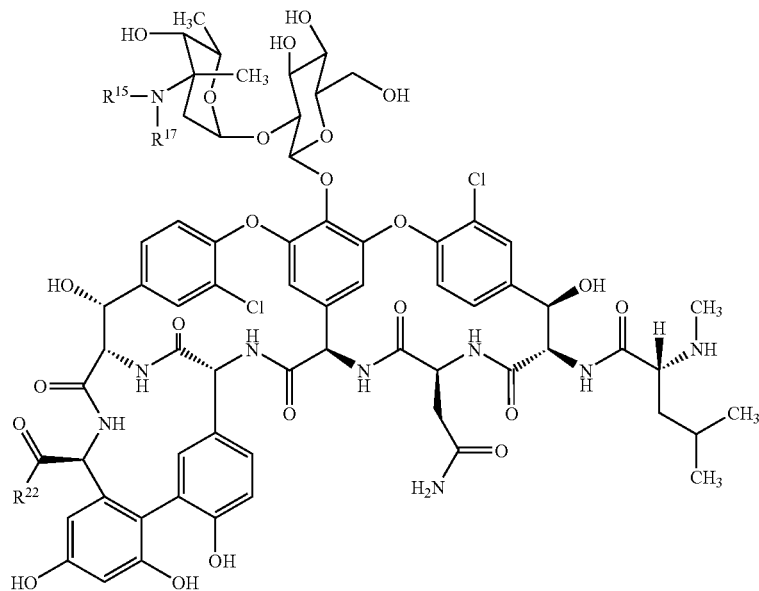

| No. | R¹⁵ (R¹⁷ = H, unless otherwise indicated) | R²² |
|---|---|---|
| 130 | —CH₂—C(O)O—(CH₂)₇CH₃ | —OH |
| 131 | —CH₂CH₂—NH—(CH₂)₉CH₃ | —NHCH(COOH)CH₂CO₂CH₃ |
| 132 | —CH₂CH₂—NH—(CH₂)₉CH₃ | —NHCH(CH₂COOH)CO₂(CH₂)₂N(CH₃)₂ |
| 133 | —CH₂CH₂—NH—CH₂CH=CH—CH=CHCH₃ (trans, trans) | —OH |
| 134 | —CH₂CH₂—NH—(CH₂)₉CH₃ | —NHCH(COOH)CH₂CO₂CH₂C(O)N(CH₃)₂ |
| 135 | —CH₂CH₂—NH—(CH₂)₉CH₃ | —NHCH(CH₂COOH)CO₂CH₂C(O)N(CH₃)₂ |
| 136 | —CH₂CH₂—NH—(CH₂)₉CH₃ | —NHCH(CH₂COOH)CO₂CH₃ |
| 137 | —CH₂CH₂—NHC(O)—CH₂CH₂—C(O)NHCH₂CH₂NH₂ | —NHCH₂CH₂CH₂N(CH₃)₂ |
| 138 | —CH₂CH₂—NHSO₂-4-Ph-Ph | —OH |
| 139 | —CH₂CH₂—NH—(CH₂)₉CH₃ | —NHCH₂CH₂CO₂CH₃ |
| 140 | —CH₂CH₂—NH—(CH₂)₉CH₃ | —NHCH[CH₂CO₂CH₂C(O)N(CH₃)₂]CO₂CH₂—C(O)—N(CH₃)₂ |
| 141 | —CH₂CH₂—NH—(CH₂)₉CH₃ | —NHCH₂CO₂CH₃ |
| 142 | —CH₂CH₂—NH—(CH₂)₉CH₃ | —N-(methyl 3-amino-3-deoxyamnnopyranoside) |
| 143 | —CH₂CH₂—NH—(CH₂)₉CH₃ | —N-(methyl 3-amino-2,3-6-trideoxyhexopyranoside) |
| 144 | —CH₂CH₂—NH—(CH₂)₉CH₃ | —N-[2-amino-2-deoxy-6-(dihydrogen phosphate)glucopyranose |
| 145 | —CH₂CH₂—NH—(CH₂)₉CH₃ | —N-(2-amino-2-deoxygluconic acid) |
| 146 | —CH₂CH₂—N(C(O)CH₂NHCH₃)—(CH₂)₉CH₃ | —OH |
| 147 | —CH₂CH₂—N(C(O)CH₃)—(CH₂)₉CH₃ | —OH |
| 148 | —CH₂CH₂—S(O)—(CH₂)₉CH₃ | —OH |
| 149 | —CH₂CH₂—NH—(CD₂)₉CD₃ | —OH |
| 150 | —CH₂CH₂—N(CH₂COOH)—(CH₂)₉CH₃ | —OH |
| 151 | —CH₂CH₂—NH—(CH₂)₉CH₃ | —NH(CH₂)₄COOH |
| 152 | —CH₂CH₂—NHSO₂-4-(4-Cl-Ph)-Ph | —OH |
| 153 | —CH₂CH₂—N(CH₂CO₂CH₃)—(CH₂)₉CH₃ | —OH |
| 154 | —CH₂CH₂—NH—(CH₂)₉CH₃ | —N—(N—CH₃-D-glucamine) |
| 155 | —CH₂CH₂—NH—(CH₂)₉CH₃ | —NH(CH₂)₆COOH |
| 156 | —CH₂—C(O)O—CH₂CH₃ | —OH |
| 157 | —CH₂CH₂—S(O)—(CH₂)₇CH₃ | —OH |
| 158 | —CH₂CH₂—NHSO₂-3-(4-Cl-Ph)-Ph | —OH |
| 159 | —CH₂CH₂—NHSO₂—(CH₂)₇CH₃ | —OH |
| 160 | —CH₂CH₂CH₂—NHSO₂-4-(4-Cl-Ph)-Ph | —OH |
| 161 | —CH₂CH₂—NH—CH₂-4-(4-Cl-PhCH₂O-)-Ph | —N-(D-glucosamine) |
| 162 | —CH₂CH₂—NH—CH₂-4-(4-Cl-PhCH₂O-)-Ph | —NHCH(COOH)CH₂COOH |
| 163 | —CH₂CH₂—NHSO₂-4-(naphth-2-yl)-Ph | —OH |
| 164 | —CH₂CH₂—NH—(CH₂)₁₁CH₃ | —OH |
| 165 | —CH₂CH₂—N[C(O)CH(NH₂)(CH₂)₄NH₂]—(CH₂)₉CH₃ (R isomer) | —OH |
| 166 | —CH₂CH₂—NHSO₂—(CH₂)₉CH₃ | —O-(D-glucose) |
| 167 | —CH₂CH₂—NHSO₂—(CH₂)₉CH₃ | —N[(CH₂)₂OH]₂ |
| 168 | —CH₂CH₂CH₂—NH—CH₂-4-(4-CF₃-Ph)-Ph | —O-(D-glucose) |
| 169 | —CH₂CH₂CH₂—NH—CH₂-4-(4-CF₃-Ph)-Ph | —N[(CH₂)₂OH]₂ |
| 170 | —CH₂CH₂CH₂—NH—CH₂-4-(4-CF₃-Ph)-Ph | —OH |
| 171 | —CH₂CH₂—NH—CH₂-4-(4-CH₃O-Ph)-Ph | —OH |
| 172 | —CH₂CH₂—NH—CH₂-4-[(CH₃)₃CO]-Ph | —OH |

TABLE I-continued

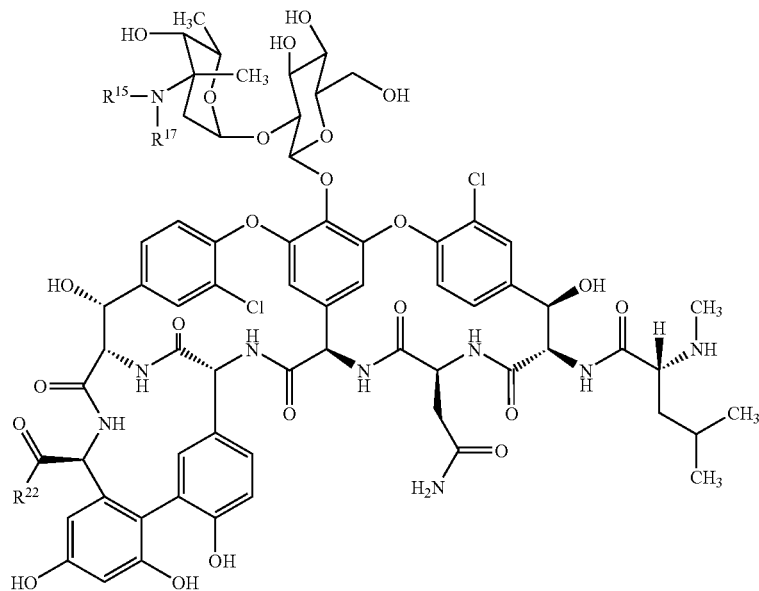

| No. | R$^{15}$ (R$^{17}$ = H, unless otherwise indicated) | R$^{22}$ |
|---|---|---|
| 173 | —CH$_2$CH$_2$—NH—CH$_2$-3,4-di-(CH$_3$CH$_2$O)-Ph | —OH |
| 174 | —CH$_2$CH$_2$—NH—CH$_2$-4-[(CH$_3$)$_2$CH]-Ph | —OH |
| 175 | —CH$_2$CH$_2$—NH—CH$_2$-4-[CH$_3$(CH$_2$)$_3$C≡C]-Ph | —OH |
| 176 | —CH$_2$CH$_2$—NH—CH$_2$-4-[(CH$_3$)$_2$CHO]-Ph | —OH |
| 177 | —CH$_2$CH$_2$—NH—CH$_2$-4-(PhC≡C)-Ph | —OH |
| 178 | —CH$_2$CH$_2$—NH—CH$_2$-4-[(CH$_3$)$_3$C]-Ph | —OH |
| 179 | —CH$_2$CH$_2$—NH—CH$_2$-5-(PhC≡C)-thiophen-2-yl | —OH |
| 180 | —CH$_2$CH$_2$—NH—CH$_2$-4-(PhCH═CH-)Ph (trans) | —OH |
| 181 | —CH$_2$CH$_2$—NH—CH$_2$—(CH═CH)$_4$—CH$_3$ (trans, trans, trans, trans) | —OH |
| 182 | —CH$_2$CH$_2$—N(C(O)Ph)—(CH$_2$)$_9$CH$_3$ | —OH |
| 183 | —CH$_2$CH$_2$—NH—CH$_2$-4-[4-(CH$_3$)$_3$C-thiazol-2-yl]-Ph | —OH |
| 184 | —CH$_2$CH$_2$—N[(CH$_2$)$_9$CH$_3$]—C(O)CH$_2$—S-4-pyridyl | —OH |
| 185 | —CH$_2$CH$_2$—N[(CH$_2$)$_9$CH$_3$]—C(O)-2-[PhCH(CH$_3$)NHC(O)-]Ph (R isomer) | —OH |
| 186 | —CH$_2$CH$_2$—N[(CH$_2$)$_9$CH$_3$]—C(O)-(1-PhCH$_2$OC(O)-2-oxoimidazolidin-5-yl) (S isomer) | —OH |
| 187 | —CH$_2$CH$_2$—N[(CH$_2$)$_9$CH$_3$]—C(O)-1-HO-cyclopropyl | —OH |
| 188 | —CH$_2$CH$_2$—N(C(O)CH$_2$-naphth-2-yl)-(CH$_2$)$_9$CH$_3$ | —OH |
| 189 | —CH$_2$CH$_2$—N[C(O)(CH$_2$)$_9$CH$_2$OH]—(CH$_2$)$_9$CH$_3$ | —OH |
| 190 | —CH$_2$CH$_2$—N[C(O)CH$_2$(OCH$_2$CH$_2$)$_2$OCH$_3$]—(CH$_2$)$_9$CH$_3$ | —OH |
| 191 | —CH$_2$CH$_2$—N[C(O)CH$_2$CH(Ph)$_2$]—(CH$_2$)$_9$CH$_3$ | —OH |
| 192 | —CH$_2$CH$_2$—N(C(O)CH$_2$-3-HO-Ph)-(CH$_2$)$_9$CH$_3$ | —OH |
| 193 | —CH$_2$CH$_2$—N(C(O)CH$_2$—NHC(O)-3-CH$_3$-Ph)-(CH$_2$)$_9$CH$_3$ | —OH |
| 194 | —CH$_2$CH$_2$—N(C(O)CH$_2$CH$_2$—O-Ph)-(CH$_2$)$_9$CH$_3$ | —OH |
| 195 | —CH$_2$CH$_2$—N(C(O)CH$_2$CH$_2$-3-pyridyl)-(CH$_2$)$_9$CH$_3$ | —OH |
| 196 | —CH$_2$CH$_2$—N(C(O)(CH$_2$)$_3$-4-CH$_3$O-Ph)-(CH$_2$)$_9$CH$_3$ | —OH |
| 197 | —CH$_2$CH$_2$—N(C(O)-indol-2-yl)-(CH$_2$)$_9$CH$_3$ | —OH |
| 198 | —CH$_2$CH$_2$—N{C(O)-1-[CH$_3$COC(O)-]-pyrrolidin-2-yl}-(CH$_2$)$_9$CH$_3$ | —OH |
| 199 | —CH$_2$CH$_2$—N(C(O)CH$_2$—NHC(O)—CH═CH-furan-2-yl)-(CH$_2$)$_9$CH$_3$ (trans) | —OH |
| 200 | —CH$_2$CH$_2$—N[C(O)-1-CH$_3$CH$_2$-7-CH$_3$-4-oxo-1,4-dihydro[1,8]naphthyridin-3-yl]-(CH$_2$)$_9$CH$_3$ | —OH |
| 201 | —CH$_2$CH$_2$—N(C(O)-1,3-benzodioxol-5-yl)-(CH$_2$)$_9$CH$_3$ | —OH |
| 202 | —CH$_2$CH$_2$—N(C(O)CH$_2$-4-oxo-2-thiooxothiazolidin-3-yl)-(CH$_2$)$_9$CH$_3$ | —OH |
| 203 | —CH$_2$CH$_2$—N(C(O)-3,4,5-tri-HO-cyclohex-1-en-1-yl)-(CH$_2$)$_9$CH$_3$ (R,S,R isomer) | —OH |
| 204 | —CH$_2$CH$_2$—N(C(O)CH$_2$CH$_2$C(O)NH$_2$)—(CH$_2$)$_9$CH$_3$ | —OH |
| 205 | —CH$_2$CH$_2$—N(C(O)CH$_2$-5-CH$_3$-2,4-dioxo-3,4-dihydropyrimidin-1-yl)-(CH$_2$)$_9$CH$_3$ | —OH |
| 206 | —CH$_2$CH$_2$—N(C(O)CH═CH-imidazol-4-yl)-(CH$_2$)$_9$CH$_3$ (trans) | —OH |
| 207 | —CH$_2$CH$_2$—N[C(O)CH(CH$_2$CH$_2$C(O)NH$_2$)—NHC(O)O—CH$_2$Ph]—(CH$_2$)$_9$CH$_3$ (S isomer) | —OH |

TABLE I-continued

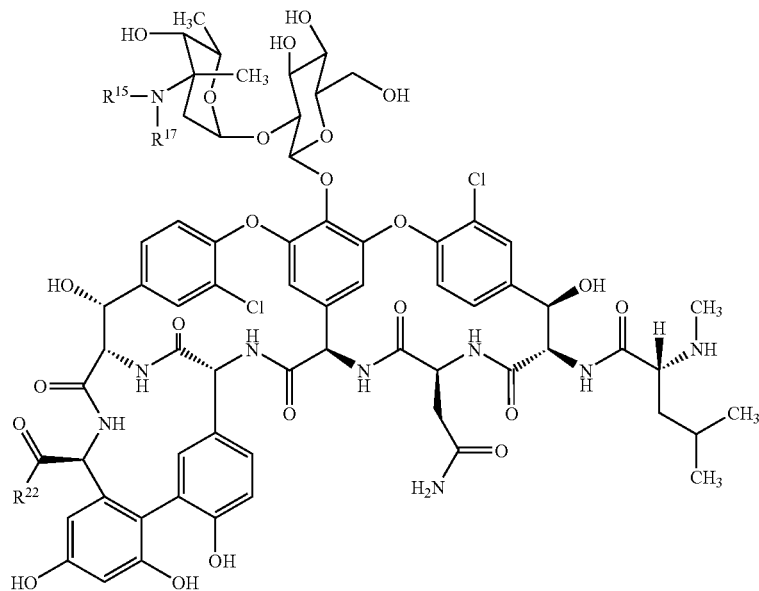

| No. | R<sup>15</sup> (R<sup>17</sup> = H, unless otherwise indicated) | R<sup>22</sup> |
|---|---|---|
| 208 | —CH$_2$CH$_2$—N[C(O)CH(CH$_2$OH)NHC(O)O—CH$_2$Ph]—(CH$_2$)$_9$CH$_3$ (S isomer) | —OH |
| 209 | —CH$_2$CH$_2$—N[C(O)CH[CH(OH)CH$_3$]NH—C(O)O—CH$_2$Ph]—(CH$_2$)$_9$CH$_3$ (S isomer) | —OH |
| 200 | —CH$_2$CH$_2$—N(C(O)CH$_2$NHSO$_2$-4-CH$_3$-Ph)-(CH$_2$)$_9$CH$_3$ | —OH |
| 211 | —CH$_2$CH$_2$—N(C(O)(CH$_2$)$_3$—NH$_2$)—(CH$_2$)$_9$CH$_3$ | —OH |
| 212 | —CH$_2$CH$_2$—N(C(O)-pyrrolidin-2-yl)-(CH$_2$)$_9$CH$_3$ (R isomer) | —OH |
| 213 | —CH$_2$CH$_2$—N(C(O)-pyrrolidin-2-yl)-(CH$_2$)$_9$CH$_3$ (S isomer) | —OH |
| 214 | —CH$_2$CH$_2$—N(C(O)CH(NH$_2$)(CH$_2$)$_4$—NH$_2$)—(CH$_2$)$_9$CH$_3$ (S isomer) | —OH |
| 215 | —CH$_2$CH$_2$—N(C(O)CH(NH$_2$)CH$_2$-3-HO-Ph)-(CH$_2$)$_9$CH$_3$ | —OH |
| 216 | —CH$_2$CH$_2$—N(C(O)CH(NH$_2$)CH$_2$)—(CH$_2$)$_9$CH$_3$ (R isomer) | —OH |
| 217 | —CH$_2$CH$_2$—N[C(O)CH(CH$_2$OH)NHC(O)—CH$_3$]—(CH$_2$)$_9$CH$_3$ (S isomer) | —OH |
| 218 | —CH$_2$CH$_2$—N[C(O)CH(NHC(O)CH$_3$)—(CH$_2$)$_3$—NHC(NH)NH$_2$]-(CH$_2$)$_9$CH$_3$ (S isomer) | —OH |
| 219 | —CH$_2$CH$_2$—N(C(O)CH$_2$NHC(O)CH$_3$)—(CH$_2$)$_9$CH$_3$ | —OH |
| 220 | —CH$_2$CH$_2$—N(C(O)CH(CH$_3$)OC(O)CH—(NH$_2$)CH$_3$)—(CH$_2$)$_9$CH$_3$ (R,R isomer) | —OH |
| 221 | —CH$_2$CH$_2$—NH—(CH$_2$)$_9$CH$_3$ | —NH(CH$_2$)$_3$OC(O)CH(NH$_2$)CH$_3$ |
| 222 | —CH$_2$CH$_2$—N(C'(O)-5-oxopyrrolidin-2-yl)-(CH$_2$)$_9$CH$_3$ (R isomer) | —OH |
| 223 | —CH$_2$CH$_2$—NHC(O)—CH$_2$CH(CH$_2$CH$_2$Ph)-{3-[4-(9H-fluroen-9-yl)CH$_2$OC(O)NH(CH$_2$)$_4$-]-1,4-dioxohexahydro-1,2-α-pyrazin-2-yl} (S,S,S isomer) | —OH |
| 224 | —CH$_2$CH$_2$—NH—(CH$_2$)$_9$CH$_3$ | —NH(CH$_2$)$_4$CH(C(O)-2-HOOC-pyrrolidin-1-yl)NHCH(COOH)—CH$_2$CH$_2$Ph (S,S isomer) |
| 225 | —CH$_2$CH$_2$—NHSO$_2$-4-(2-Cl-Ph)-Ph | —OH |
| 226 | —CH$_2$CH$_2$—NHSO$_2$-4-[4-(CH$_3$)$_3$C-Ph]-Ph | —OH |
| 227 | —CH$_2$CH$_2$—NHSO$_2$-4-[4-(Ph)-Ph-]Ph | —OH |
| 228 | —CH—CH$_2$—NH-4-(4-CF$_3$-Ph)-Ph | —OH |
| 229 | —CH$_2$CH$_2$—S—(CH$_2$)$_8$Ph | —OH |
| 230 | —CH$_2$CH$_2$—S—(CH$_2$)$_3$CH=CH(CH$_2$)$_4$CH$_3$ (trans) | —OH |
| 231 | —CH$_2$CH$_2$—S—CH$_2$CH$_2$(CF$_2$)$_5$CF$_3$ | —OH |
| 232 | —CH$_2$CH$_2$—S—CH$_2$-4-[(CH$_3$)$_2$CHCH$_2$-]Ph | —OH |
| 233 | —CH$_2$CH$_2$—S—(CH$_2$)$_{11}$CH$_3$ | —OH |
| 234 | —CH$_2$CH$_2$—S—(CH$_2$)$_8$CH$_3$ | —OH |
| 235 | —CH$_2$CH$_2$—S—CH$_2$-3,4-di-(PhCH$_2$O-)Ph | —OH |
| 236 | —CH$_2$CH$_2$CH$_2$—S—(CH$_2$)$_8$Ph | —OH |
| 237 | —CH$_2$CH$_2$CH$_2$—S—(CH$_2$)$_8$CH$_3$ | —OH |
| 238 | —CH$_2$CH$_2$CH$_2$—S—(CH$_2$)$_9$CH$_3$ | —OH |
| 239 | —CH$_2$CH$_2$CH$_2$—S—(CH$_2$)$_6$Ph | —OH |

TABLE I-continued

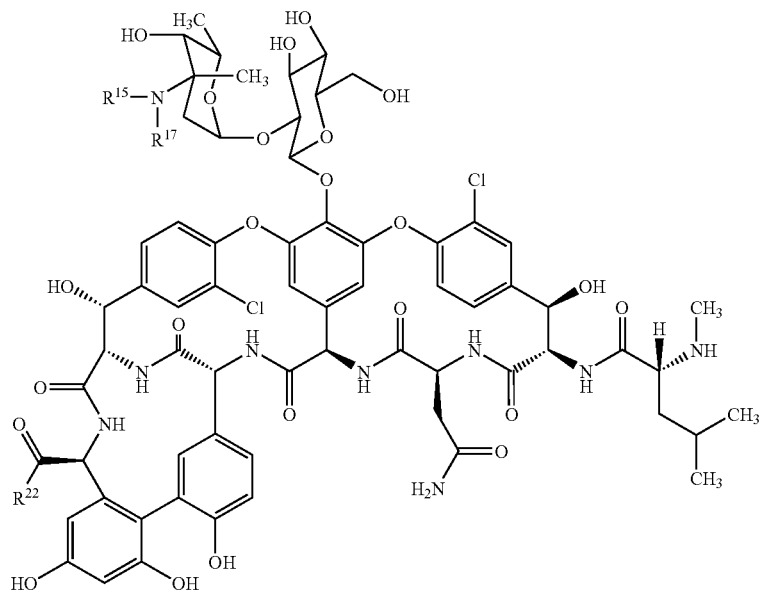

III

| No. | R¹⁵ (R¹⁷ = H, unless otherwise indicated) | R²² |
|---|---|---|
| 240 | —CH₂CH₂CH₂CH₂—S—(CH₂)₇CH₃ | —OH |
| 241 | —CH₂CH₂—S—(CH₂)₆Ph | —OH |
| 242 | —CH₂CH₂—S—(CH₂)₁₀Ph | —OH |
| 243 | —CH₂CH₂CH₂—S—CH₂-4-[(CH₃)₂CHCH₂-]Ph | —OH |
| 244 | —CH₂CH₂—S—(CH₂)₃CH═CH(CH₂)₄CH₃ (trans) | —OH |
| 245 | —CH₂CH₂—S—CH₂-4-[3,4-di-Cl-PhCH₂O-]Ph | —OH |
| 246 | —CH₂CH₂CH₂—S—CH₂-4-[3,4-di-Cl-PhCH₂O-]Ph | —OH |
| 247 | —CH₂CH₂—SO-4-(4-Cl-Ph)-Ph | —OH |
| 248 | —CH₂CH₂CH₂—SO-4-(4-Cl-Ph)-Ph | —OH |
| 249 | —CH₂CH₂—S—(CH₂)₁₀CH₃ | —OH |
| 250 | —CH₂CH₂CH₂—S—(CH₂)₁₀CH₃ | —OH |
| 251 | —CH₂CH₂CH₂—S—CH₂-4-[CH₃(CH₂)₄O-]Ph | —OH |
| 252 | —CH₂CH₂CH₂—S—CH₂CH═CH—CH═CH(CH₂)₄CH₃ (trans, trans) | —OH |
| 253 | —CH₂CH₂—S—CH₂-4-[4-Cl-PhCH₂O-]Ph | —OH |
| 254 | —CH₂CH₂CH₂—S—CH₂-4-[4-Cl-PhCH₂O-]Ph | —OH |
| 255 | —CH₂CH₂—NH—(CH₂)₉CH₃ | tetrazol-5-yl |
| 256 | —CH₂CH₂CH₂—S—CH₂-(CH₂)₉CH₃ | —N-(D-glucosamine) |
| 257 | —CH₂CH₂CH₂—S—CH₂-4-(4-CF₃-Ph-)Ph | —OH |
| 258 | —CH₂CH₂—S—(CH₂)₉CH₃ | tetrazol-5-yl |
| 259 | —CH₂CH₂CH₂—S—CH₂-4-(4-F-PhSO₂NH-)Ph | —OH |
| 260 | —CH₂CH₂CH₂—S—(CH₂)₈CH₃ | —OH |
| 261 | —CH₂CH₂CH₂—S(O)—(CH₂)₆Ph | —OH |
| 262 | —CH₂CH₂—S(O)—(CH₂)₈Ph | —OH |
| 263 | —CH₂CH₂—S—(CH₂)₃-4-Cl-Ph | —OH |
| 264 | —CH₂CH₂—S—(CH₂)₆-4-Cl-Ph | —OH |
| 265 | —CH₂CH₂—SO₂—(CH₂)₉CH₃ | —OH |
| 421 | —H | —NH—CH₂CH₂—NH—(CH₂)₉CH₃ |

Ph= phenyl

TABLE II

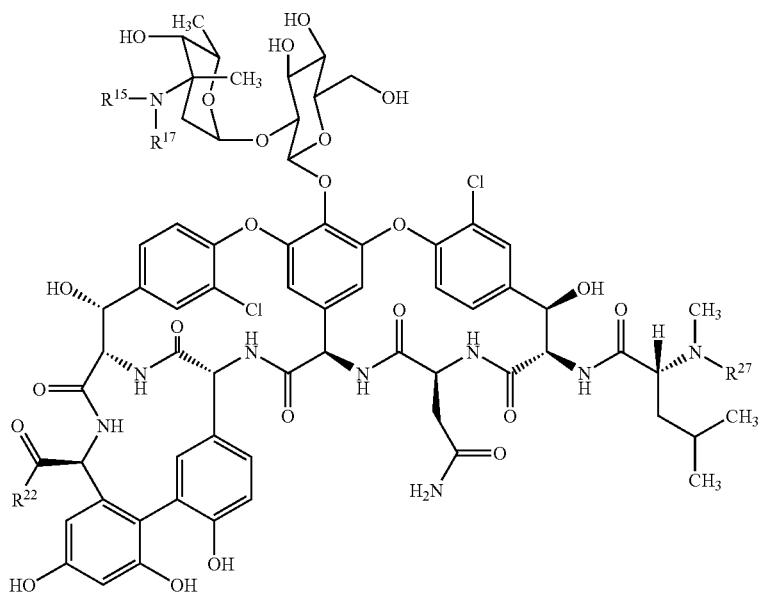

IV

| No. | R¹⁵ (R¹⁷ = H, unless otherwise indicated) | R²² | R²⁷ |
|---|---|---|---|
| 266 | —CH₂CH₂—NH—(CH₂)₉CH₃ | —OH | —CH₂—[CH(OH)]₅CH₂OH |
| 267 | —CH₂CH₂—NH—(CH₂)₉CH₃ | —OH | —CH₂CH(OH)CH₂OH |
| 268 | —CH₂CH₂—NH—(CH₂)₉CH₃ | —OH | —CH₂CH₂NH₂ |
| 269 | —CH₂CH₂—NH—(CH₂)₉CH₃ | —OH | —CH₂C(O)OCH₂CH₃ |
| 270 | —CH₂CH₂—NH—(CH₂)₉CH₂ | —OH | —CH₂COOH |
| 271 | —CH₂CH₂—NH—(CH₂)₉CH₃<br>R¹⁷ = —CH₂COOH | —OH | —CH₂COOH |
| 272 | —CH₂CH₂—NH—(CH₂)₉CH₃ | —OH | —CH₂-2-pyridyl |
| 273 | —CH₂CH₂—NH—(CH₂)₈CH₃ | —OH | —CH₂[CH(OH)]₄COOH |
| 274 | —H | —NHCH₂C(O)CH₂C(O)N(CH₃)₂ | —H |
| 275 | —CH₂CH₂—NH—(CH₂)₉CH₃ | —OH | —CH₂-3-HOOC-Ph |
| 276 | —CH₂CH₂—N(C(O)CH(NH₂)—(CH₂)₄NH₂)—(CH₂)₉CH₃ (R isomer) | —OH | —C(O)CH(NH₂)(CH₂)₄NH₂ (R isomer) |
| 277 | —CH₂CH₂—NH—(CH₂)₁₁CH₃ | —OH | —CH₂COOH |
| 278 | —CH₂CH₂—N(C(O)Ph)—(CH₂)₉CH₃ | —OH | —C(O)Ph |
| 279 | —CH₂CH₂—N(C(O)CH₂NHC(O)CH₃)—(CH₂)₉CH₃ | —OH | —C(O)CH₂NHC(O)CH₃ |
| 280 | —CH₂CH₂—S—(CH₂)₃CH=CH(CH₂)₄CH₃ (trans) | —OH | —CH₂CH₂—S—(CH₂)₃CH=CH(CH₂)₄CH₃ (trans) |
| 281 | —CH₂CH₂—NH—(CH₂)₉CH₃ | —OH | —C(O)CH₃ |

Ph=phenyl

TABLE III

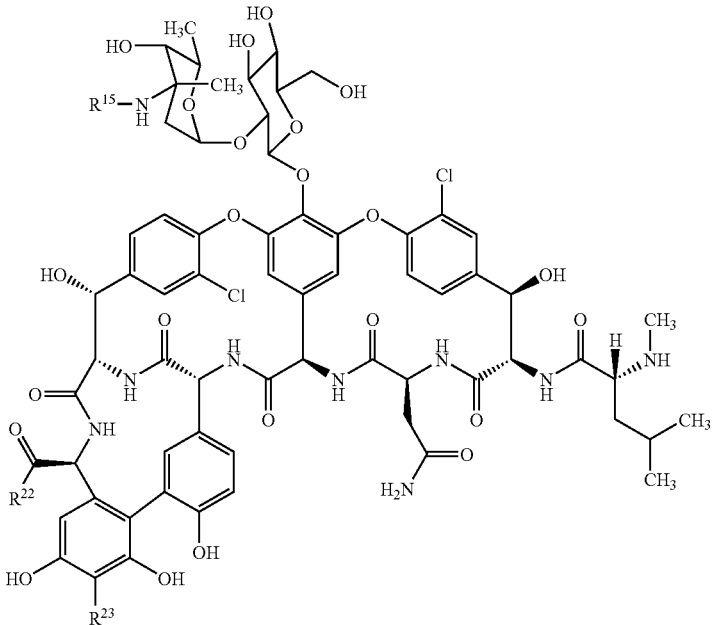

| No. | R15 | R22 | R23 |
|---|---|---|---|
| 282 | —CH₂CH₂—NH—(CH₂)₉CH₃ | —OH | —CH₂—N—(N—CH₃-D-glucamine) |
| 283 | —CH₂CH₂—NH—CH₂-4-(4-Cl-Ph)Ph | —OH | —CH₂—N—(N—CH₃-D-glucamine) |
| 284 | —CH₂CH₂—NH—(CH₂)₈CH(OH)CH₃ | —OH | —CH₂—N—(N—CH₃-D-glucamine) |
| 285 | —CH₂CH₂—NH—(CH₂)₉CH₃ | —N-(-D-glucosamine) | —CH₂—N—(N—CH₃-D-glucamine) |
| 286 | —CH₂CH₂—NH—(CH₂)₉CH₃ | —OH | —CH₂—N—(N—CH₃-D-glucamine) |
| 287 | —H | —OH | —CH₂—NH—CH₂CH₂—NH—(CH₂)₉CH₃ |
| 288 | —CH₂CH₂—NH—CH₂-4-(4-Cl-Ph)Ph | —OH | —CH₂—N—(N—CH₃-D-glucamine) |
| 289 | —H | —NH—(CH₂)₃—N(CH₃)₂ | —CH₂—NH—CH₂CH₂—NHC(O)—(CH₂)₃COOH |
| 290 | —CH₂CH₂—NH—(CH₂)₉CH₃ | —OH | —CH₂—NH—(CH₂)₉CH₃ |
| 291 | —CH₂CH₂—NH—(CH₂)₉CH₃ | —OH | —CH₂—NH—CH₂CH₂—COOH |
| 292 | —CH₂CH₂—NH—(CH₂)₉CH₃ | —OH | —CH₂—NH—(CH₂)₅—COOH |
| 293 | —CH₂CH₂—NH—(CH₂)₉CH₃ | —OH | —CH₂-(morpholin-4-yl) |
| 294 | —CH₂CH₂—NH—(CH₂)₉CH₃ | —OH | —CH₂—NH—CH₂CH—O—CH₂CH₂OH |
| 295 | —CH₂CH₂—NH—(CH₂)₉CH₃ | —OH | —CH₂—NH—CH₂CH(OH)CH₂OH |
| 296 | —CH₂CH₂—NH—(CH₂)₉CH₃ | —OH | —CH₂—N[CH₂CH₂OH]₂ |
| 297 | —CH₂CH₂—NH—(CH₂)₉CH₃ | —OH | —CH₂—NH—(CH₂)₃—N(CH₃)₂ |
| 298 | —CH₂CH₂—NH—(CH₂)₉CH₃ | —OH | —CH₂—N[(CH₂)₃—N(CH₃)₂]₂ |
| 299 | —CH₂CH₂—NH—(CH₂)₉CH₃ | —OH | —CH₂—NH—(CH₂)₃-(imidazol-1-yl) |
| 300 | —CH₂CH₂—NH—(CH₂)₉CH₃ | —OH | —CH₂—NH—(CH₂)₃-(morpholin-4-yl) |
| 301 | —CH₂CH₂—NH—(CH₂)₉CH₃ | —OH | —CH₂—NH—(CH₂)₄—NHC(NH)NH₂ |
| 302 | —CH₂CH₂—NHSO₂—(CH₂)₇CH₃ | —OH | —CH₂—N—(N—CH₃-D-glucamine) |
| 303 | —CH₂CH₂—NHSO₂—(CH₂)₉CH₃ | —OH | —CH₂—N—(N—CH₃-D-glucamine) |
| 304 | —CH₂CH₂—NH—(CH₂)₉CH₃ | —NHCH(COOH)CH₂COOH | —CH₂—N—(N—CH₃-D-glucamine) |
| 305 | —CH₂CH₂—NH—(CH₂)₇CH(OH)CH₂CH₃ | —OH | -3,5-di-HO-4-[-CH₂—N—(N—CH₃-D-glucamine)]Ph |
| 306 | —CH₂CH₂—NH—(CH₂)₁₀OH | —OH | —CH₂—N—(N—CH₃-D-glucamine) |
| 307 | —CH₂CH₂—NHSO₂-4-Ph-Ph | —OH | —CH₂—N—(N—CH₃-D-glucamine) |
| 308 | —CH₂CH₂—NH—(CH₂)₉CH₃ | —OH | —CH₂—N—(N—CH₃-D-glucamine) |
| 309 | —CH₂CH₂—NH—(CH₂)₇CH₃ | —OH | —CH₂—N—(N—CH₃-D-glucamine) |
| 310 | —CH₂CH₂—NH—(CD₂)₉CD₃ | —OH | —CH₂—N—(N—CH₃-D-glucamine) |
| 311 | —CH₂CH₂—S—(CH₂)₉CH₃ | —OH | —CH₂—N—(N—CH₃-D-glucamine) |
| 312 | —CH₂CH₂—NH—(CH₂)₉CH₃ | —OH | —CH₂—N-(2-amino-2-deoxygluconic acid) |
| 313 | —H | —OH | —CH₂—NH—CH₂CH₂—NH—(CH₂)₇CH₃ |
| 314 | —CH₂CH₂—NH—(CH₂)₉CH₃ | —OH | —CH₂—NHCH(COOH)CH₂COOH |
| 315 | —H | —OH | —CH₂—NH—CH₂CH₂—NHSO₂—(CH₂)₇CH₃ |
| 316 | —H | —OH | —CH₂—NH—CH₂CH₂—NHSO₂—(CH₂)₉CH₃ |
| 317 | —H | —OH | —CH₂—NH—CH₂CH₂—NHSO₂—(CH₂)₁₁CH₃ |
| 318 | —H | —OH | —CH₂—NH—CH₂CH₂—NH—(CH₂)₇CH₃ |
| 319 | —CH₂CH₂—SO—(CH₂)₉CH₃ | —OH | —CH₂—N—(N—CH₃-D-glucamine) |
| 320 | —CH₂CH₂—NHSO₂—CH₂-4-(4-Cl-Ph)Ph | —OH | —CH₂—N—(N—CH₃-D-glucamine) |
| 321 | —CH₂CH—NH—CH₂CH=CH—CH=CH(CH₂)₄CH₃ (trans, trans) | —OH | —CH₂—N—(N—CH₃-D-glucamine) |
| 322 | —CH₂CH₂—NHSO₂—(CH₂)₉CH₃ | —OH | —CH₂—NH—CH₂CH₂—O—CH₂CH₂OH |
| 323 | —CH₂CH₂CH₂—NHSO₂—CH₂-4-(4-Cl-Ph)Ph | —OH | —CH₂—N—(N—CH₃-D-glucamine) |
| 324 | —CH₂CH₂—NH—CH₂-4-[(CH₃)₂CHCH₂-]Ph | —OH | —CH₂—N—(N—CH₃-D-glucamine) |

TABLE III-continued

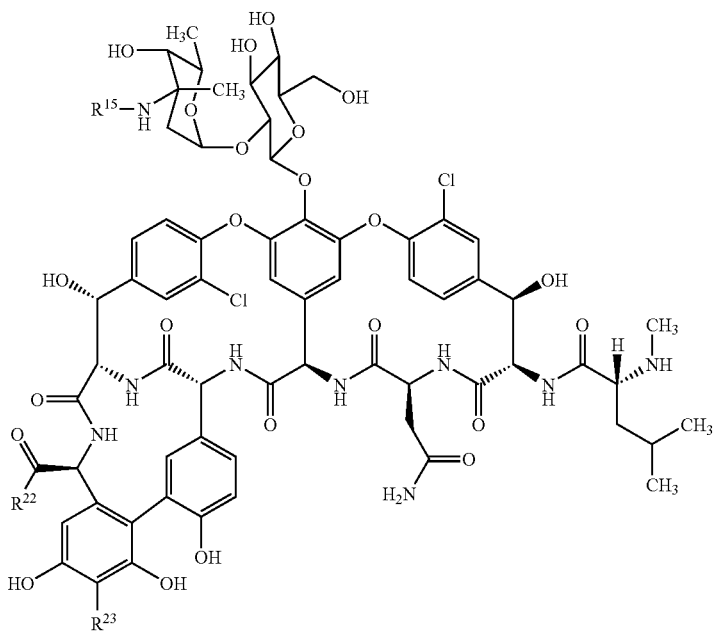

V

| No. | R15 | R22 | R23 |
|---|---|---|---|
| 325 | —CH2CH2—NH—CH2-4-[(CH3)2CHCH2-]Ph | —OH | —CH2—NH—CH2CH2—O—CH2CH2OH |
| 326 | —CH2CH2—NH—CH2-4-[4-Cl-PhCH2O-]Ph | —OH | —CH2—N—(N—CH3-D-glucamine) |
| 327 | —CH2CH2—NH—(CH2)9CH3 | —OH | —CH2—NHCH2CH2C(O)—N—(D-glucosamine) |
| 328 | —CH2CH2—NH—(CH2)9CH3 | —OH | —CH2—NH—CH2CH2—O—CH2CH2OH |
| 329 | —CH2CH2—NH—(CH2)9CH3 | —NHCH(COOH)CH2COOH | —CH2—NH—CH2CH2—O—CH2CH2OH |
| 330 | —CH2CH2—NH—(CH2)11CH3 | —OH | —CH2—N—(N—CH3-D-glucamine) |
| 331 | —CH2CH2CH2—NH—CH2-4-(4-CF3-Ph)Ph | —OH | —CH2—NH—CH2CH2—O—CH2CH2OH |
| 332 | —CH2CH2CH2—NH—CH2-4-(4-CF3-Ph)Ph | —OH | —CH2—N—(N—CH3-D-glucamine) |
| 333 | —CH2CH2CH2—NH—CH2-4-(4-CF3-Ph)Ph | —OH | —CH2—NH—(CH2)3-(imidazol-1-yl) |
| 334 | —CH2CH2—NHSO2—(CH2)9CH3 | —OH | —CH2—NH—(6-oxo-[1,3]oxazinan-3-yl) |
| 335 | —CH2CH2—NH—(CH2)8CH3 | —OH | —CH2—N—(N—CH3-D-glucamine) |
| 336 | —CH2CH2—NHSO2—(CH2)9CH3 | —OH | —CH2—NH—(CH2)3-(imidazol-1-yl) |
| 337 | —H | —N-(D-glucamine) | —CH2—NH—CH2CH2—NHSO2—(CH2)11CH3 |
| 338 | —H | —OH | —CH2—NH—CH2CH2—S—(CH2)7CH3 |
| 339 | —H | —OH | —CH2—NH—CH2CH2—S—(CH2)8CH3 |
| 340 | —H | —OH | —CH2—NH—CH2CH2—NHSO2—(CH2)8CH3 |
| 341 | —H | —OH | —CH2—NH—CH2CH2—S—(CH2)9CH3 |
| 342 | —H | —OH | —CH2—NH—CH2CH2—NHSO2—(CH2)7CH2 |
| 343 | —CH2CH2—NH—CH2-4-(4-CF3-Ph)Ph | —OH | —CH2—N—(N—CH3-D-glucamine) |
| 344 | —H | —OH | —CH2—NH—CH2CH2—S—(CH2)11CH3 |
| 345 | —H | —OH | —CH2—NH—CH2CH2—NHSO2—(CH2)11CH3 |
| 346 | —H | —OH | —CH2—NH—CH2CH2—S—(CH2)6Ph |
| 347 | —H | —OH | —CH2—NH—CH2CH2—S—(CH2)8Ph |
| 348 | —H | —OH | —CH2—NH—CH2CH2—S—(CH2)10Ph |
| 349 | —H | —OH | —CH2—NH—CH2CH2—S—CH2-4-(4-CF3-Ph)Ph |
| 350 | —CH2CH2—S—(CH2)8Ph | —OH | —CH2—N—(N—CH3-D-glucamine) |
| 351 | —H | —OH | —CH2—NH—CH2CH2—SO2—(CH2)11CH3 |
| 352 | —CH2CH2—S—(CH2)8CH3 | —OH | —CH2—N—(N—CH3-D-glucamine) |

Ph = phenyl

TABLE IV

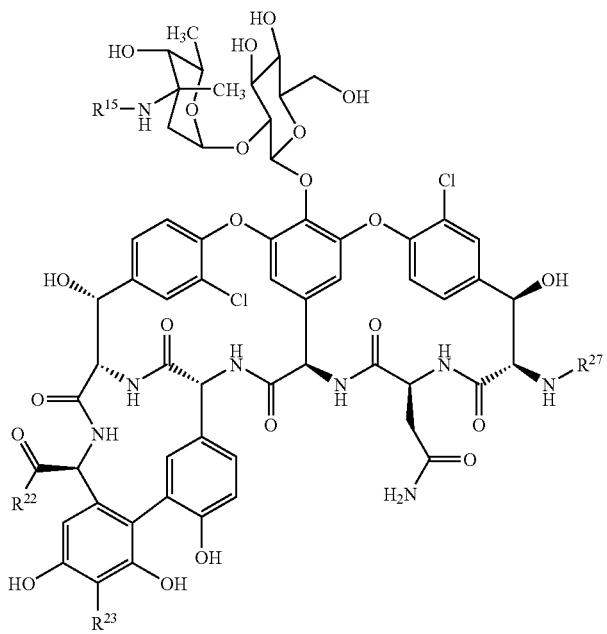

VI

| No. | R$^{15}$ (R$^{23}$ = H, unless otherwise indicated) | R$^{22}$ | R$^{27}$ |
|---|---|---|---|
| 353 | —CH$_2$CH—NH—(CH$_2$)$_9$CH$_3$ | —OH | —H |
| 354 | —H | —OH | —CH$_2$CH$_2$—NH—(CH$_2$)$_9$CH$_3$ |
| 355 | —CH$_2$CH$_2$—NH—(CH$_2$)$_9$CH$_3$ | —OH | —CH$_2$CH$_2$—NH—(CH$_2$)$_9$CH$_3$ |
| 356 | —CH$_2$CH$_2$—NH—(CH$_2$)$_9$CH$_3$ R$^{23}$ = —CH$_2$—N—(N—CH$_3$-D-glucamine) | —OH | —H |
| 357 | —CH$_2$CH$_2$—NH—(CH$_2$)$_9$CH$_3$ | —N-(D-glucosamine) | —H |
| 358 | —CH$_2$CH$_2$—NH—(CH$_2$)$_9$CH$_3$ | —OH | —(CH$_2$)$_3$CH(CH$_3$)$_2$ |
| 359 | —CH$_2$CH$_2$—NH—(CH$_2$)$_9$CH$_3$ | —OH | —C(O)CH$_2$CH$_2$CH(CH$_3$)$_2$ |
| 360 | —CH$_2$CH$_2$—NH—(CH$_2$)$_9$CH$_3$ | —OH | —C(O)CH(NH$_2$)(CH$_2$)$_4$NH$_2$ (R isomer) |
| 361 | —CH$_2$CH$_2$—NH—(CH$_2$)$_9$CH$_3$ | —OH | —C(O)CH(NH$_2$)(CH$_2$)$_4$NH$_2$ (S isomer) |
| 362 | —CH$_2$CH$_2$—NH—(CH$_2$)$_9$CH$_3$ | —OH | —C(O)CH(NH$_2$)(CH$_2$)$_2$COOH (R isomer) |
| 363 | —CH$_2$CH$_2$—NH—(CH$_2$)$_9$CH$_3$ | —OH | —C(NH)NH$_2$ |
| 364 | —CH$_2$CH$_2$—NH—(CH$_2$)$_9$CH$_3$ | —OH | —C(O)CH(NH$_2$)CH$_2$-(imidazol-4-yl) (R isomer) |
| 365 | —CH$_2$CH$_2$—NH—(CH$_2$)$_9$CH$_3$ | —OH | —C(O)CH(NH$_2$)CH$_2$—COOH (R isomer) |
| 366 | —CH$_2$CH$_2$—NH—(CH$_2$)$_9$CH$_3$ | —OH | —C(O)CH(NH$_2$)CH(CH$_3$)CH$_2$CH$_3$ (S isomer) |
| 367 | —CH$_2$CH$_2$—NH—(CH$_2$)$_9$CH$_3$ | —OH | —C(O)NHCH$_2$CH(CH$_3$)$_2$ |
| 368 | —CH$_2$CH$_2$—NH—(CH$_2$)$_9$CH$_3$ | —OH | —C(NH)CH$_2$CH(CH$_3$)$_2$ |
| 369 | —CH$_2$CH$_2$—NH—(CH$_2$)$_9$CH$_3$ | —OH | —C(O)CH(NH$_2$)CH$_2$-Ph (R isomer) |
| 370 | —CH$_2$CH$_2$—NH—(CH$_2$)$_9$CH$_3$ | —OH | —C(O)CH$_2$NHCH$_3$ |
| 371 | —CH$_2$CH$_2$—NH—(CH$_2$)$_9$CH$_3$ | —OH | —C(O)CH(NH$_2$)CH$_2$-3-HO-Ph |
| 372 | —CH$_2$CH$_2$—NH—(CH$_2$)$_9$CH$_3$ | —OH | —C(O)CH(NH$_2$)CH$_2$-3-HO-Ph |
| 373 | —CH$_2$CH$_2$—NH—(CH$_2$)$_9$CH$_3$ | —OH | —C(O)-2-[PhCH(CH$_3$)NHC(O)-]Ph (R isomer) |
| 374 | —CH$_2$CH$_2$—NH—(CH$_2$)$_9$CH$_3$ | —OH | —C(O)-[1-PhC(O)-2-oxoimidazolidin-5-yl] (S isomer) |
| 375 | —CH$_2$CH$_2$—NH—(CH$_2$)$_9$CH$_3$ | —OH | —C(O)CH$_2$-(1-HO-cycloprop-1-yl) |
| 376 | —CH$_2$CH$_2$—NH—(CH$_2$)$_9$CH$_3$ | —OH | —C(O)CH$_2$-(naphth-2-yl) |
| 377 | —CH$_2$CH$_2$—NH—(CH$_2$)$_9$CH$_3$ | —OH | —C(O)(CH$_2$)$_9$—OH |
| 378 | —CH$_2$CH$_2$—NH—(CH$_2$)$_9$CH$_3$ | —OH | —C(O)-2,4-di-HO-Ph |
| 379 | —CH$_2$CH$_2$—NH—(CH$_2$)$_9$CH$_3$ | —OH | —C(O)-2,6-di-HO-3-pyridyl |
| 380 | —CH$_2$CH$_2$—NH—(CH$_2$)$_9$CH$_3$ | —OH | —C(O)CH$_2$—O—CH$_2$CH$_2$—O—CH$_2$CH$_2$OCH$_3$ |
| 381 | —CH$_2$CH$_2$—NH—(CH$_2$)$_9$CH$_3$ | —OH | —C(O)CH$_2$CH(Ph)$_2$ |
| 382 | —CH$_2$CH$_2$—NH—(CH$_2$)$_9$CH$_3$ | —OH | —C(O)CH$_2$-3-HO-Ph |
| 383 | —CH$_2$CH$_2$—NH—(CH$_2$)$_9$CH$_3$ | —OH | —C(O)CH$_2$—NHC(O)-3-CH$_3$-Ph |
| 384 | —CH$_2$CH$_2$—NH—(CH$_2$)$_9$CH$_3$ | —OH | —C(O)CH$_2$CH$_2$—O-Ph |

TABLE IV-continued

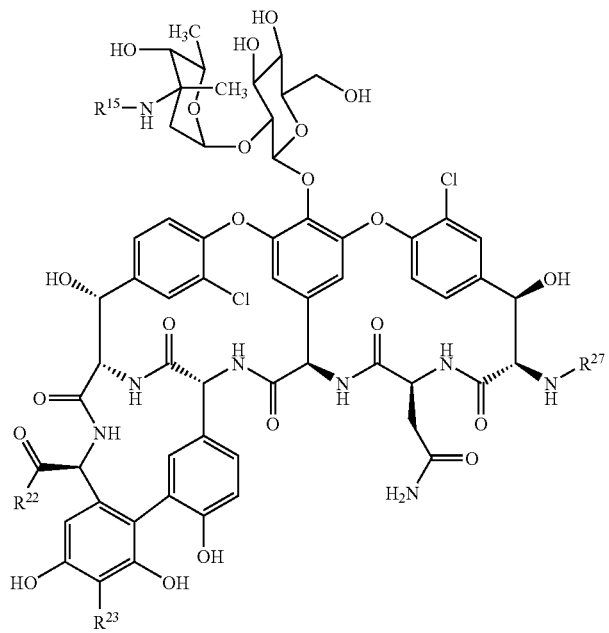

VI

| No. | R15 (R23 = H, unless otherwise indicated) | R22 | R27 |
|---|---|---|---|
| 385 | —CH₂CH₂—NH—(CH₂)₉CH₃ | —OH | —C(O)CH₂CH₂-3-pyridyl |
| 386 | —CH₂CH₂—NH—(CH₂)₉CH₃ | —OH | —C(O)CH₂CH₂CH₂—4-CH₃O-Ph |
| 387 | —CH₂CH₂—NH—(CH₂)₉CH₃ | —OH | —C(O)-(3H-beazotriazol-5-yl) |
| 388 | —CH₂CH₂—NH—(CH₂)₉CH₃ | —OH | —C(O)-[1-(CH₃)₃COC(O)-pyrrohdin-2-yl) (S isomer) |
| 389 | —CH₂CH₂—NH—(CH₂)₉CH₃ | —OH | —C(O)CH₂CH₂CH₂-cyclohexyl |
| 390 | —CH₂CH₂—NH—(CH₂)₉CH₃ | —OH | —C(O)-(1H-indol-2-yl) |
| 391 | —CH₂CH₂—NH—(CH₂)₉CH₃ | —OH | —C(O)CH₂NHC(O)-furan-2-yl |
| 392 | —CH₂CH₂—NH—(CH₂)₉CH₃ | —OH | —C(O)CH(NHC(O)CH₃)CH₂-4-HO-Ph (S isomer) |
| 393 | —CH₂CH₂—NH—(CH₂)₉CH₃ | —OH | —C(O)CH₂NHC(O)CH═CH-furan-2-yl (trans) |
| 394 | —CH₂CH₂—NH—(CH₂)₉CH₃ | —OH | —C(O)-(1-CH₃CH₂-7-CH₃-4-oxo-1,4-dihydro[1,8]naphthryridin-3-yl) |
| 395 | —CH₂CH₂—NH—(CH₂)₉CH₃ | —OH | —C(O)-2,3,4,5,6-penta-F-Ph |
| 396 | —CH₂CH₂—NH—(CH₂)₉CH₃ | —OH | —C(O)-(1,3-benzodioxol-5-yl) |
| 397 | —CH₂CH₂—NH—(CH₂)₉CH₃ | —OH | —C(O)CH₂-(4-oxo-2-thiooxothiazolidin-3-yl) |
| 398 | —CH₂CH₂—NH—(CH₂)₉CH₃ | —OH | —C(O)-(3,4,5-tri-HO-cyclohex-1-enyl) |
| 399 | —CH₂CH₂—NH—(CH₂)₉CH₃ | —OH | —C(O)CH₂CH₂C(O)NH₂ |
| 400 | —CH₂CH₂—NH—(CH₂)₉CH₃ | —OH | —C(O)CH₂-(5-CH₃-2,4-dioxo-3,4-dihydropyrimidin-1-yl) |
| 401 | —CH₂CH₂—NH—(CH₂)₉CH₃ | —OH | —C(O)CH(NH₂)CH(CH₃)₂(R isomer) |
| 402 | —CH₂CH₂—NH—(CH₂)₉CH₃ | —OH | —C(O)CH(NH₂)CH₂C(O)-(2-H₂N-Ph) |
| 403 | —CH₂CH₂—NH—(CH₂)₉CH₃ | —OH | —C(O)CH₂—NH₂ |
| 404 | —CH₂CH₂—NH—(CH₂)₉CH₃ | —OH | —C(O)CH(NHCH₃)CH₂CH(CH₃)₂(S isomer) |
| 405 | —CH₂CH₂—NH—(CH₂)₉CH₃ | —OH | —C(O)CH(NH₂)CH₂CH(CH₃)₂(S isomer) |

Ph = phenyl

TABLE V
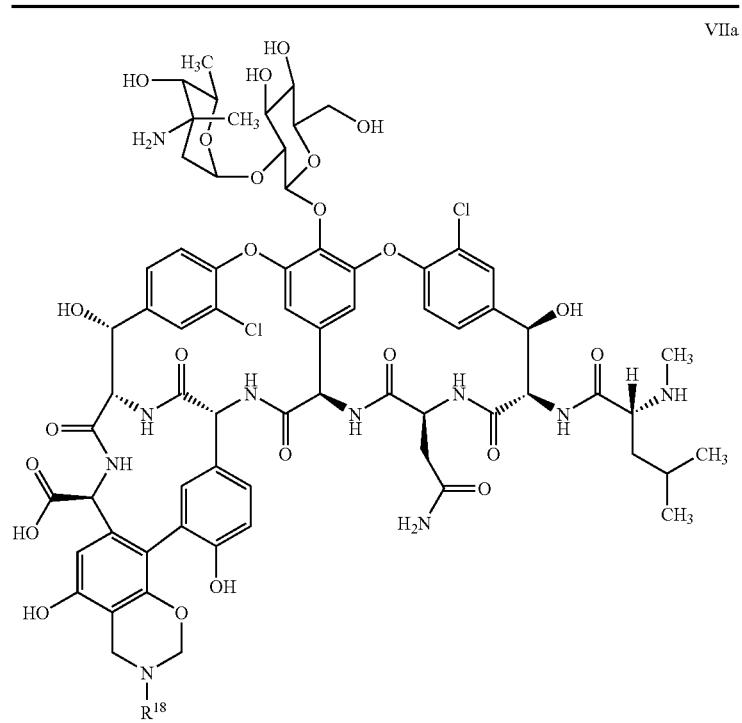
VIIa
and/or
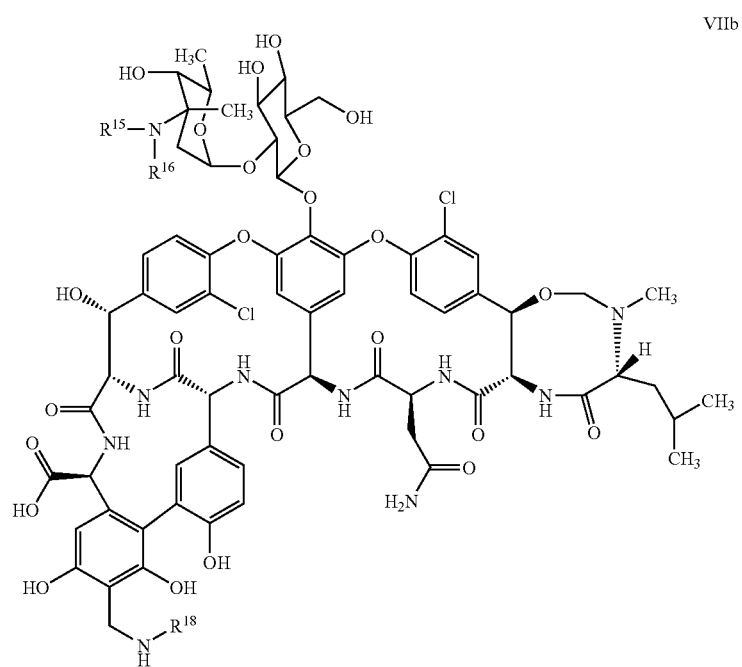
VIIb
| No. | R[18] |
|---|---|
| 406 | —CH$_2$CH$_2$—NHSO$_2$—(CH$_2$)$_7$CH$_3$ |
| 407 | —CH$_2$CH$_2$—NHSO$_2$—(CH$_2$)$_9$CH$_3$ |
| 408 | —CH$_2$CH$_2$—NHSO$_2$—(CH$_2$)$_{11}$CH$_3$ |
| 409 | —CH$_2$CH$_2$—S—(CH$_2$)$_7$CH—CH$_2$ |
| 410 | —CH$_2$CH$_2$—S—(CH$_2$)$_8$CH$_3$ |
| 411 | —CH$_2$CH$_2$CH$_2$—NHSO$_2$—(CH$_2$)$_9$CH$_3$ |
| 412 | —CH$_2$CH$_2$—S—(CH$_2$)$_9$CH$_3$ |
| 413 | —CH$_2$CH$_2$CH$_2$—NHSO$_2$—(CH$_2$)$_7$CH$_3$ |
| 414 | —CH$_2$CH$_2$—S—(CH$_2$)$_{11}$CH$_3$ |

TABLE V-continued
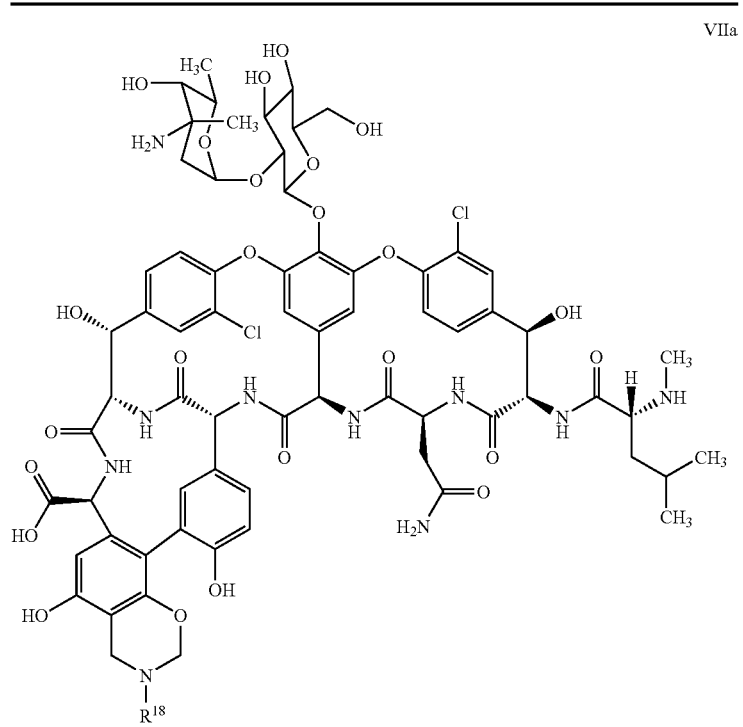
VIIa
and/or
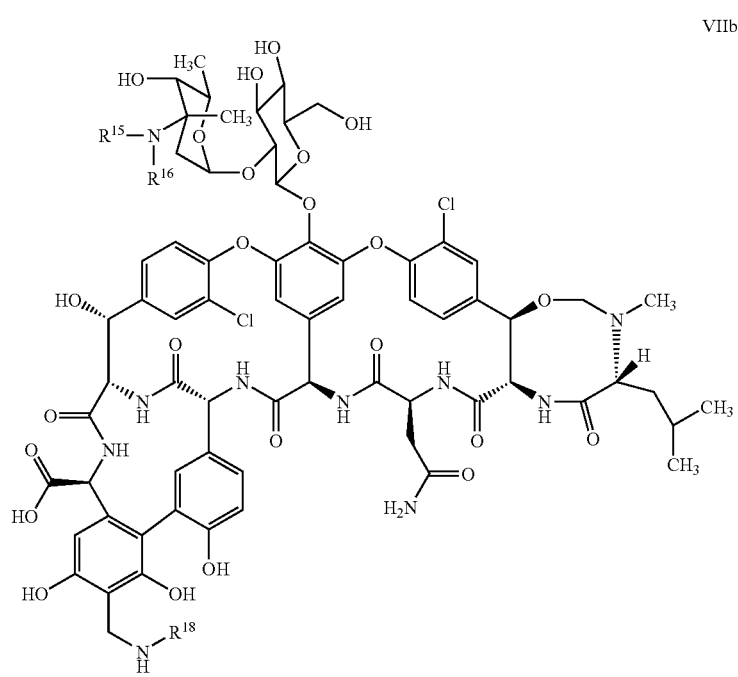
VIIb
| No. | R[18] |
|---|---|
| 415 | —CH$_2$CH$_2$—S—(CH$_2$)$_6$Ph |
| 416 | —CH$_2$CH$_2$—S—(CH$_2$)$_8$Ph |
| 417 | —CH$_2$CH$_2$—S—(CH$_2$)$_{10}$Ph |
| 418 | —CH$_2$CH$_2$—S—CH$_2$-4-(CF$_3$-Ph)-Ph |
Ph = phenyl

TABLE VI

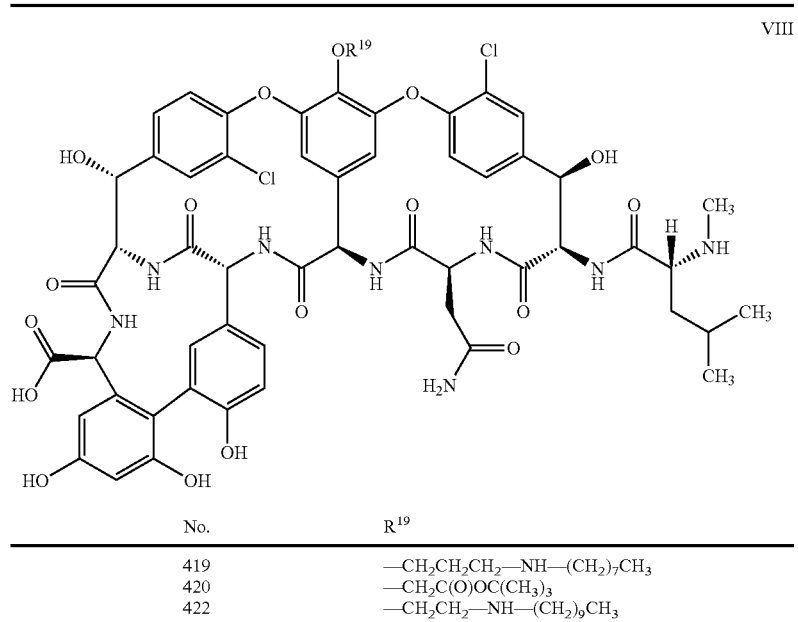

| No. | R[19] |
|---|---|
| 419 | —CH₂CH₂CH₂—NH—(CH₂)₇CH₃ |
| 420 | —CH₂C(O)OC(CH₃)₃ |
| 422 | —CH₂CH₂—NH—(CH₂)₉CH₃ |

DETAILED DESCRIPTION OF THE INVENTION

This invention relates to novel derivatives of glycopeptide antibiotics and to pharmaceutical compositions and methods employing such glycopeptide derivatives. When describing the compounds, compositions and methods of this invention, the following terms have the following meanings, unless otherwise indicated

DEFINITIONS

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like. The term "substituted alkyl" refers to an alkyl group as defined above, having from 1 to 8 substituents, preferably 1 to 5 substitutents, and more preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SOI-alkyl, —SO₂-substituted alkyl, —SO₂-aryl and —SO₂-heteroaryl.

The term "alkylene" refers to a diradical of a branched or unbranched saturated hydrocarbon chain, preferably having from 1 to 40 carbon atoms, preferably 1-10 carbon atoms, more preferably 1-6 carbon atoms. This term is exemplified by groups such as methylene (—CH₁₂—), ethylene (—CH₂CH₂—), the propylene isomers (e.g., —CH₂CH₂CH₂— and —CH(CH₃)CH₂—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO₂-aryl and —SO₂-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures. Additionally, the term substituted alkylene includes alkylene groups in which from 1 to 5 of the alkylene carbon atoms are replaced with oxygen, sulfur or —NR— where R is hydrogen or alkyl. Examples of substituted alkylenes are chloromethylene (—CH(Cl)—), aminoethylene (—CH(NH₂)CH₂—), 2-carboxypropylene isomers (—CH₂CH(CO₂H)CH₂—), ethoxyethyl (—CH₂CH₂O—CH₂CH₂—) and the like.

The term "alkaryl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-5-alkyl, alkylene-5-substituted alkyl, substituted alkylene-5-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-1-thiobutoxy (—CH$_2$SC(CH$_3$)$_3$) and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1-6 sites of vinyl unsaturation. Preferred alkenyl groups include ethenyl (—CH═CH$_2$), n-propenyl (—CH$_2$CH═CH$_2$), iso-propenyl (—C(CH$_3$)═CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1-6 sites of vinyl unsaturation. This term is exemplified by groups such as ethenylene (—CH═CH—), the propenylene isomers (e.g., —CH$_2$CH═CH— and —C(CH$_3$)═CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1-6 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynylene" refers to a diradical of an unsaturated hydrocarbon preferably having from 2 to 40 carbon atoms, more preferably 2 to 10 carbon atoms and even more preferably 2 to 6 carbon atoms and having at least 1 and preferably from 1-6 sites of acetylene (triple bond) unsaturation. Preferred alkynylene groups include ethynylene (—C≡C—), propargylene (—CH$_2$C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, sulfonamide, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

"Amino acid" refers to any of the naturally occurring amino acids, as well as synthetic analogs and derivatives thereof. α-Amino acids comprise a carbon atom to which is bonded an amino group, a carboxy group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine).

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

"Haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heteroarylalkyl" refers to (heteroaryl)alkyl- where heteroaryl and alkyl are as defined herein. Representative examples include 2-pyridylmethyl and the like.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "heterocycle" or "heterocyclic" refers to a monoradical saturated unsaturated group having a single ring or multiple condensed rings, from 1 to 40 carbon atoms and from 1 to hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocloxy, thiol, thioalkoxy, substituted thioalkoxy, aryl, aryloxy, heteroaryl, heteroaryloxy, heterocyclic, heterocloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

Another class of heterocyclics is known as 'crown compounds' which refers to a specific class of heterocyclic compounds having one or more repeating units of the formula [—(CH$_2$-)$_a$A-] where a is equal to or greater than 2, and A at each separate occurrence can be O, N, S or P. Examples of crown compounds include, by way of example only, [—(CH$_2$)$_3$—NH—]$_3$, [—((CH$_2$)$_2$—O)$_4$—((CH$_2$)$_2$—NH)$_2$] and the like. Typically such crown compounds can have from 4 to 10 heteroatoms and 8 to 40 carbon atoms.

The term "heterocyclooxy" refers to the group heterocyclic-O—.

The term "thioheterocyclooxy" refers to the group heterocyclic-S—.

The term "heterocyclene" refers to the diradical group formed from a heterocycle, as defined herein, and is exemplified by the groups 2,6-morpholino, 2,5-morpholino and the like.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "saccharide group" refers to an oxidized, reduced or substituted saccharide monoradical covalently attached to the glycopeptide or other compound via any atom of the saccharide moiety, preferably via the aglycone carbon atom. Representative saccharides include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine, D-glucuronic acid, N-acetyl-D-glucosamine, N-acetyl-D-galactosamine, sialyic acid, iduroric acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. For the purposes of this definition, these saccharides are referenced using conventional three letter nomenclature and the saccharides can be either in their open or preferably in their pyranose form.

The term "amino-containing saccharide group" refers to a saccharide group having an amino substituent. Representative amino-containing saccharides include L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like.

The term "spiro-attached cycloalkyl group" refers to a cycloalkyl group attached to another ring via one carbon atom common to both rings.

The term "sulfonamide" refers to a group of the formula —SO$_2$NRR, where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all sterochemical isomers arising from the substitution of these compounds.

"Glycopeptide" refers to heptapeptide antibiotics, characterized by a multi-ring peptide core optionally substituted with saccharide groups, such as vancomycin. Examples of glycopeptides included in this definition may be found in "Glycopeptides Classification, Occurrence, and Discovery", by Raymond C. Rao and Louise W. Crandall, ("Drugs and the Pharmaceutical Sciences" Volume 63, edited by Ramakrishnan Nagarajan, published by Marcal Dekker, Inc.), which is hereby incorporated by reference in its entirety. Representative glycopeptides include those identified as A477, A35512, A40926, A41030, A42867, A47934, A80407, A82846, A83850, A84575, AB-65, Actaplanin, Actinoidin, Ardacin, Avoparcin, Azureomycin, Balhimycin, Chloroorientiein, Chloropolysporin, Decaplanin, N-demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UK-69542, UK-72051, Vancomycin, and the like. The term "glycopeptide" as used herein is also intended to include the general class of peptides disclosed above on which the sugar moiety is absent, i.e. the aglycone series of glycopeptides. For example, removal of the disaccharide moiety appended to the phenol on vancomycin by mild hydrolysis gives vancomycin aglycone. Also within the scope of the invention are glycopeptides that have been further appended with additional saccharide residues, especially aminoglycosides, in a manner similar to vancosamine.

"Vancomycin" refers to a glycopeptide antibiotic having the formula:

synthesis of the bacterial cell wall. The action of this enzyme is inhibited by a ligand domain that binds to the enzyme substrate. A ligand such as vancomycin binds to this substrate and in effect "sequesters" the substrate to prevent its recognition by the enzyme and subsequent use in the construction of the bacterial cell wall.

"Potency" as used herein refers to the minimum concentration at which a compound or ligand is able to achieve a desirable biological or therapeutic effect. The potency of a compound or ligand is typically proportional to its affinity for its binding site. In some cases, the potency may be non-linearly correlated with its affinity As used herein, the terms "inert organic solvent" or "inert solvent" or "inert diluent" mean a solvent or diluent which is essentially inert under the conditions of the reaction in which it is employed as a solvent or diluent. Representative examples of materials which may be used as inert solvents or diluents include, by way of illustration, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$), diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable salt" means those salts which retain the biological effectiveness and properties of the parent compounds and which are not biologically or other-

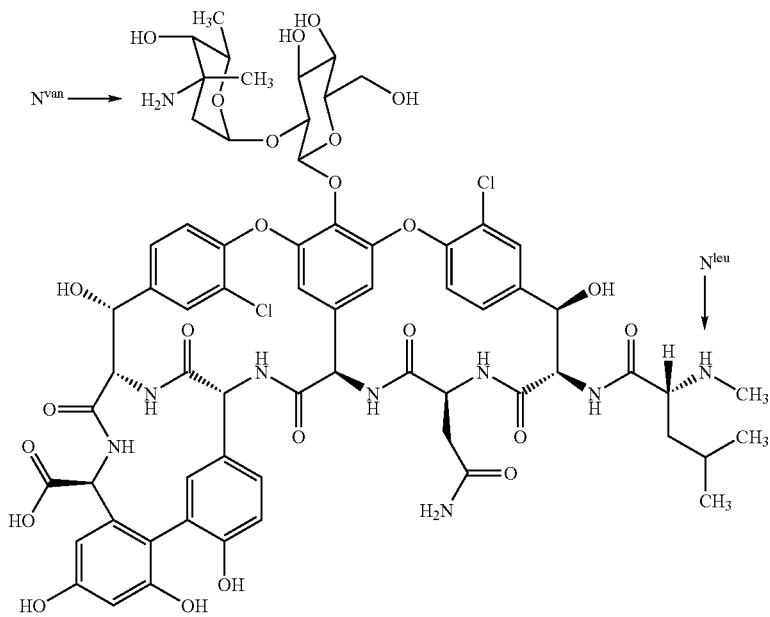

When describing vancomycin derivatives, the term "N$^{van-}$" indicates that a substituent is covalently attached to the amino group of the vacosamine moiety of vacomycin. Similarly, the term "N$^{leu-}$" indicates that a substituent is covalently attached to the amino group of the leucine moiety of vancomycin.

"Optional" or "optionally" means that the subsequently described event or circumstance may or may not occur, and that the description includes instances where said event or circumstance occurs and instances in which it does not. For example, "optionally substituted" means that a group may or may not be substituted with the described substitutent.

"Transglycosylase enzyme substrate" as used herein denotes the molecular target of the transglycosylase enzyme. The substrate binds to the enzyme and eventually results in wise harmful as the dosage administered. The compounds of this invention are capable of forming both acid and base salts by virtue of the presence of amino and carboxyl groups respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of this invention typically contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

The term "treatment" as used herein includes any treatment of a condition or disease in an animal, particularly a mammal, more particularly a human, and includes:

(i) preventing the disease or condition from occurring in a subject which may be predisposed to the disease but has not yet been diagnosed as having it;

(ii) inhibiting the disease or condition, i.e. arresting its development; relieving the disease or condition, i.e. causing regression of the condition; or relieving the conditions caused by the disease, i.e. symptoms of the disease.

The term "disease state which is alleviated by treatment with a broad spectrum antibacterial" as used herein is intended to cover all disease states which are generally acknowledged in the art to be usefully treated with a broad spectrum antibacterial in general, and those disease states which have been found to be usefully treated by the specific antibacterials of this invention. Such disease states include, but are not limited to, treatment of a mammal afflicted with pathogenic bacteria, in particular staphylococci (methicillin sensitive and resistant), streptococci (penicillin sensitive and resistant), enterococci (vancomycin sensitive and resistant), and *Clostridium difficile*

The term "therapeutically effective amount" refers to that amount which is sufficient to effect treatment, as defined herein, when administered to a mammal in need of such treatment. The therapeutically effective amount will vary depending on the subject and disease state being treated, the severity of the affliction and the manner of administration, and may be determined routinely by one of ordinary skill in the art.

The term "protecting group" or "blocking group" refers to any group which, when bound to one or more hydroxyl, thiol, amino, carboxyl or other groups of the compounds, prevents undesired reactions from occurring at these groups and which protecting group can be removed by conventional chemical or enzymatic steps to reestablish the hydroxyl, thio, amino, carboxyl or other group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Protecting groups are disclosed in more detail in T. W. Greene and P. G. M. Wuts, "Protective Groups in Organic Synthesis" 2$^{nd}$ Ed., 1991, John Wiley and Sons, N.Y.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

Preferred carboxyl protecting groups include esters such as methyl, ethyl, propyl, t-butyl etc. which can be removed by mild conditions compatible with the nature of the product.

"Biological effect" as used herein includes, but is not limited to, increased affinity, increased selectivity, increased potency, increased efficacy, increased duration of action, decreased toxicity, and the like.

General Synthetic Procedures

The glycopeptide compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Second Edition, Wiley, New York, 1991, and references cited therein.

In the following reaction schemes, the glycopeptide compounds are depicted in a simplified form as a box "G" that shows the carboxy terminus labeled [C], the vancosamine amino terminus labeled [V], the "non-saccharide" amino terminus (leucine amine moiety) labeled [N], and optionally, the resorcinol moiety labeled [R] as follows:

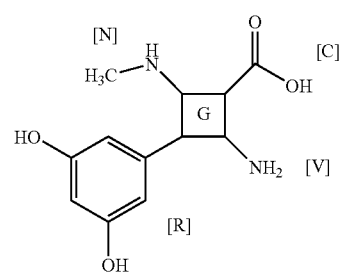

In one preferred embodiment, the glycopeptide compounds of the present invention are prepared by reductive alkylation of a glycopeptide as shown in the following reaction:

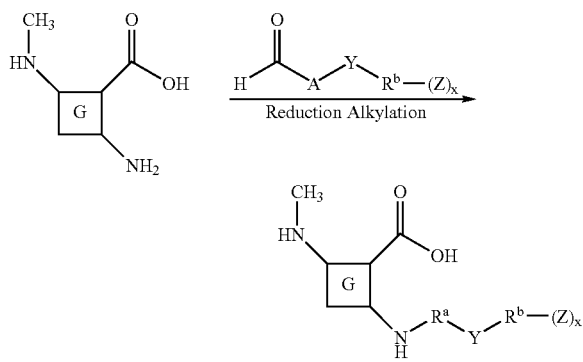

where A represents $R^a$ minus one carbon atom and $R^a$, $R^b$, Y, Z and x are as defined herein. This reaction is typically conducted by first contacting one equivalent of a glycopeptide, such as vancomycin, with an excess, preferably from 1.1 to 1.3 equivalents, of the desired aldehyde in the presence of an excess, preferably about 2.0 equivalents, of a tertiary amine, such as diisopropylethylamine (DIPEA) and the like. This reaction is typically conducted in an inert diluent, such as DMF, at ambient temperature for about 1 to 2 hours until formation of the corresponding imine and/or hemiaminal is substantially complete. The resulting imine and/or hemiaminal is typically not isolated, but is reacted in situ with a metal hydride reducing agent, such as sodium cyanoborohydride and the like, to afford the corresponding amine. This reaction is typically conducted by contacting the imine and/or hemiaminal with about 1 to 1.2 equivalents of the reducing agent at ambient temperature in methanol in the presence of an excess, preferably about 3 equivalents, of trifluoroacetic acid. The resulting alkylated product is readily purified by conventional procedures, such as reverse-phase HPLC. Surprisingly, by forming the imine and/or hemiaminal in the presence of a trialkyl amine, the selectivity for the reductive alkylation reaction is greatly improved, i.e., reductive alkylation at the amino group of the saccharide (e.g., vancosamine) is favored over reductive alkylation at the N-terminus (e.g., the leucinyl group) by at least 10:1, more preferably 20:1.

If desired, the glycopeptide compounds of this invention can also be prepared in a step-wise manner in which a precursor to the $-R^c-Y-R^b-(Z)_x$ group is first attached the glycopeptide by reductive alkylation, followed by subsequent elaboration of the attached precursor using conventional reagent and procedures to form the $-R^c-Y-R^b-(Z)_x$ group as illustrated below. Additionally, ketones may also be employed in the above-described reductive alkylation reactions to afford α-substituted amines.

Any glycopeptide having an amino group may be employed in these reductive alkylation reactions. Such glycopeptides are well-known in the art and are either commercially available or may be isolated using conventional procedures. Suitable glycopeptides are disclosed, by way of example, in U.S. Pat. Nos. 3,067,099; 3,338,786; 3,803,306; 3,928,571; 3,952,095; 4,029,769; 4,051,237; 4,064,233; 4,122,168; 4,239,751; 4,303,646; 4,322,343; 4,378,348; 4,497,802; 4,504,467; 4,542,018; 4,547,488; 4,548,925; 4,548,974; 4,552,701; 4,558,008; 4,639,433; 4,643,987; 4,661,470; 4,694,069; 4,698,327; 4,782,042; 4,914,187; 4,935,238; 4,946,941; 4,994,555; 4,996,148; 5,187,082; 5,192,742; 5,312,738; 5,451,570; 5,591,714; 5,721,208; 5,750,509; 5,840,684; and 5,843,889; the disclosures of which are incorporated herein by reference in their entirety. Preferably, the glycopeptide employed in the above reaction is vancomycin.

The aldehydes and ketones employed in the reactive alkylation reaction are also well-known in the art and are either commercially available or can be prepared by conventional procedures using commercially available starting materials and conventional reagents. Typically, such materials are prepared by conventional coupling of, for example, functionalized acetals having an amino, thiol, hydroxyl, halo or other substitutent, with an suitable intermediate having a complementary functional group to form sulfides, ethers, amines, sulfonamides and the like. Subsequent hydrolysis of the acetal affords the corresponding aldehyde. Such reactions are well-known in the art and are described, for example, in March, *Advanced Organic Chemistry*, Fourth Edition, John Wiley & Sons, New York (1992), and references cited therein. Representative synthesis of aldehyde compounds are illustrated in Schemes 1-5:

Scheme 1

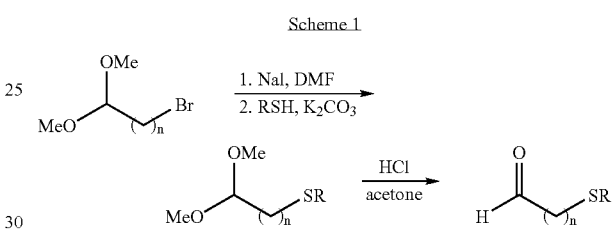

Scheme 2

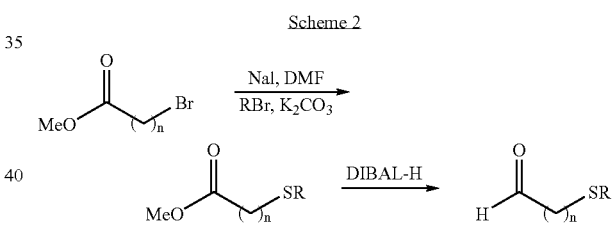

Scheme 3

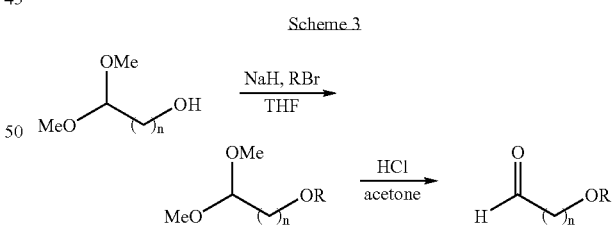

Scheme 4

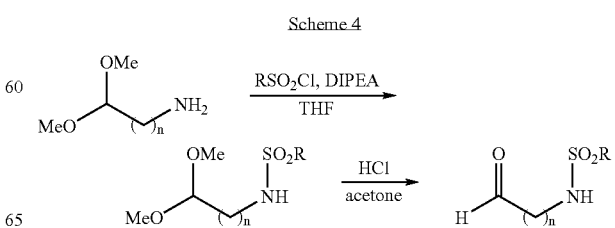

Scheme 5

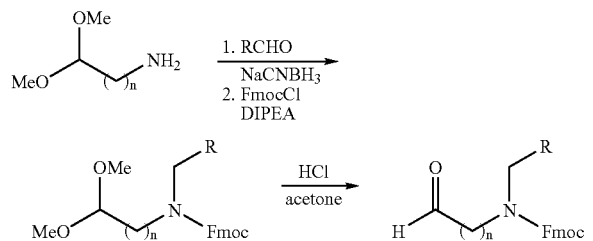

where R represents —$R^b$—$(Z)_x$ or —($R^b$ minus one carbon atom)—$(Z)_x$ (where $R^b$, Z and x are as defined herein).

By way of further illustration, the following schemes describe the synthesis of representative starting materials and compounds of this invention. For example, Scheme A illustrates a method for preparing an Fmoc-aminoaldehyde 5 from the corresponding aminoalcohol 3, where A is as defined herein. In this reaction, the aminoalcohol is protected by conventional techniques, for example, by treatment with 9-fluorenylmethyl chloroformate in the presence of base, to yield the Fmoc-protected aminoalcohol 4. Oxidation by known techniques then provides the aldehyde 5.

Scheme A

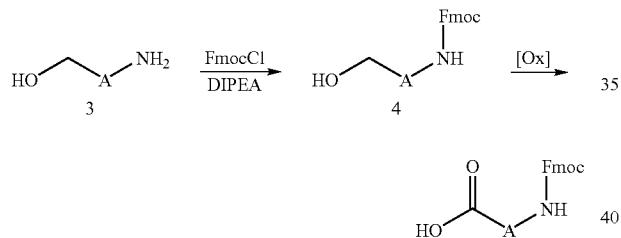

Scheme B illustrates an alternate route to F-moc-protected aminoaldehyde 5. This route is described in further detail in Sasake, Y., Abe, J. Chem. Pharm. Bull. (1997), 45(1), 13-17.

Scheme B

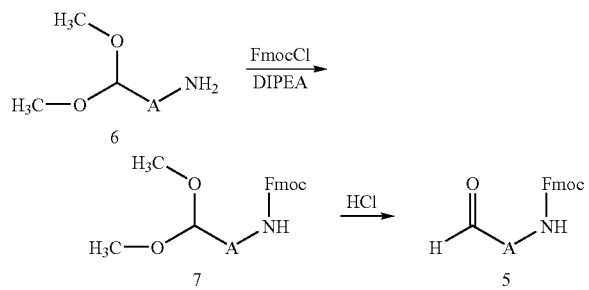

The Fmoc-protected aminoaldehyde of formula 5 can then be reacted with a glycopeptide, for example vancomycin, as shown in Scheme C.

Scheme C

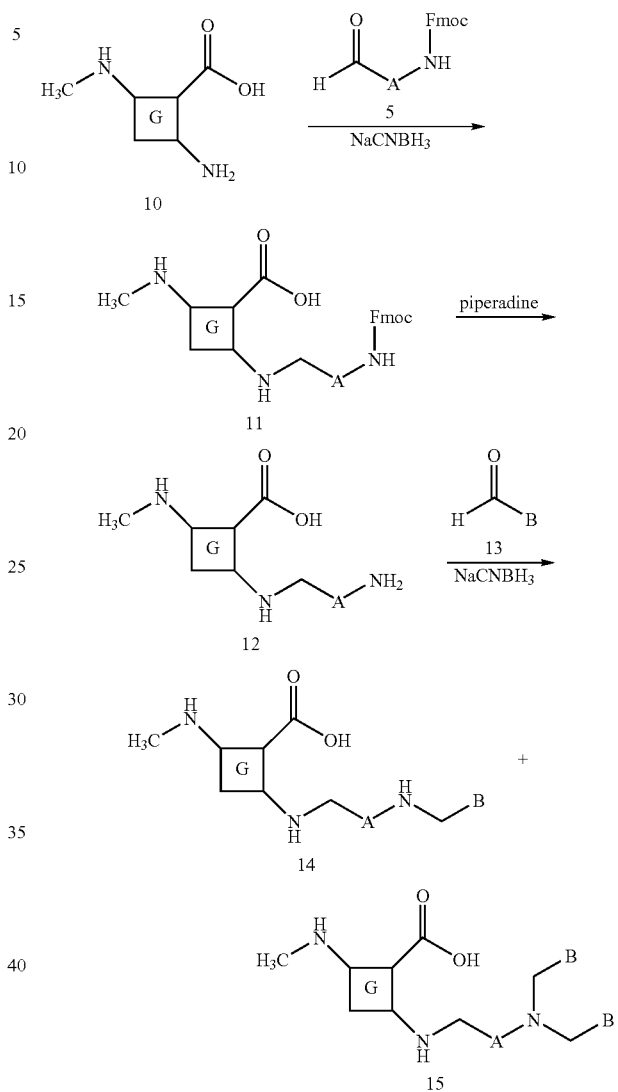

where B represents —($R^b$ minus one carbon atom)—$(Z)_x$, where $R^b$, Z and x are as defined herein.

This reaction is conducted under reductive alkylation conditions to yield a glycopeptide intermediate 11. Deprotection of 11 with piperidine yields the corresponding the glycopeptide 12 having a primary amino group. Reaction of 12 with aldehyde 13 under standard reductive alkylation conditions gives glycopeptide derivative 14 and the corresponding bis-adduct 15, which are separated by conventional techniques, such as HPLC.

Scheme D illustrates a method for preparing an Fmoc protected aminoaldehyde 24. In this scheme, reaction of acid chloride 19 with aminoester 20 under conventional amide coupling conditions gives amidoester 21. Reduction of the both the ester and amide moieties using a metal hydride reducing agent, such as lithium aluminum hydride (LAH) gives aminoalcohol 22. Protection and oxidation, as in Scheme A, yields an aldehyde of formula 24.

Alternatively, aldehyde 24 can be prepared as shown in Scheme D'. In this reaction, direct alkylation of amino alcohol 3 under conventional amine alkylation conditions gives amino alcohol 22, which can then be used as described above in Scheme D.

Scheme E illustrates an alternative method for preparing aldehyde 24. In this reaction, amino acetal 6 is reductively alkylated to provide 25. Subsequent protection of the amino group and hydrolysis of the acetal under conventional conditions then provides aldehyde 24.

Scheme F illustrates another method for reductive alkylation of a glycopeptide. In this scheme, Fmoc-protected aldehyde 24, prepared as described above, is reacted with a glycopeptide 10, such as vancomycin, under reductive alkylation conditions to afford glycopeptide derivative 27 Subsequent deprotection with piperidine provides glycopeptide derivative 14.

Scheme G illustrates the conversion of the carboxyl group of a glycopeptide derivative, such as vancomycin, into an amide. In this reaction, amine 28 is reacted with a glycopeptide derivative, such as 27, under standard peptide coupling conditions, for example, PyBOP and HOBT in DMF, to provide amide 29, after deprotection.

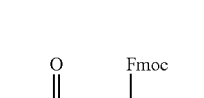

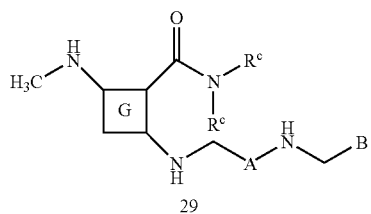

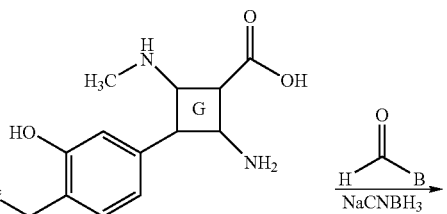

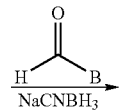

Scheme H illustrates the introduction of an aminoalkyl sidechain at the resorcinol moiety of a glycopeptide, such as vancomycin, via a Mannich reaction. In this reaction, amine 30 and an aldehyde, such as formalin (a source of formaldehyde), are reacted with the glycopeptide under basic conditions to give the glycopeptide derivative 31.

Scheme H

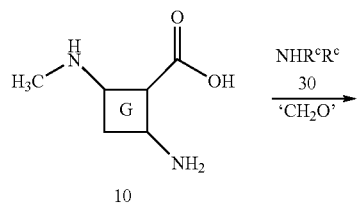

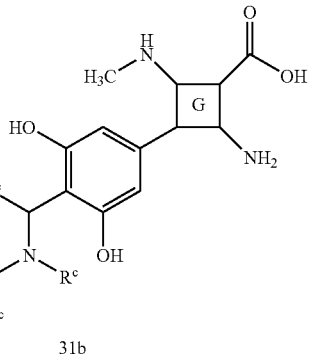

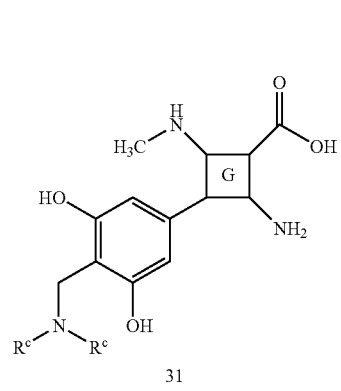

Similarly, Scheme I illustrates a introduction of a substituent of the formula —$R^a$—Y—$R^b$—$(Z)_x$ at the resorcinol moiety of a glycopeptide using the Mannich reaction. In these reactions, excess aldehyde, such as formaldehyde, can react to afford the cyclized compounds of formula VIIIa and/or VIIb.

Scheme J illustrates a synthesis of a glycopeptide derivative using several of the reactions described above. In this scheme, glycopeptide derivative 27 is derivatized at the resorcinol moiety using the Mannich reaction described in Scheme H to provide glycopeptide derivative 40. Deprotection and amide coupling at the carboxyl group, as described in Scheme G, affords glycopeptide derivative 42.

Scheme J

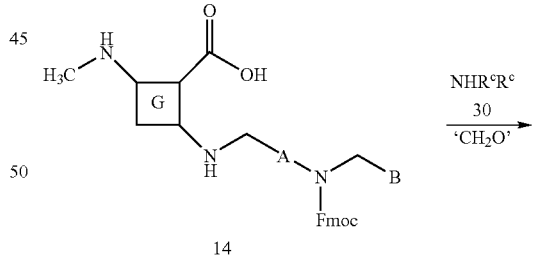

Scheme I

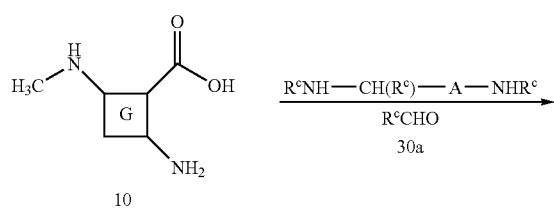

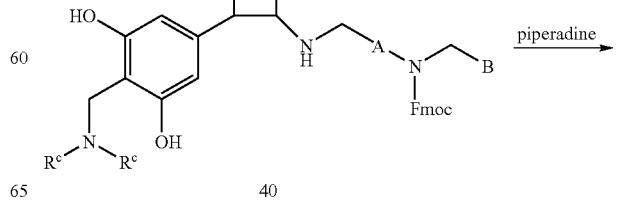

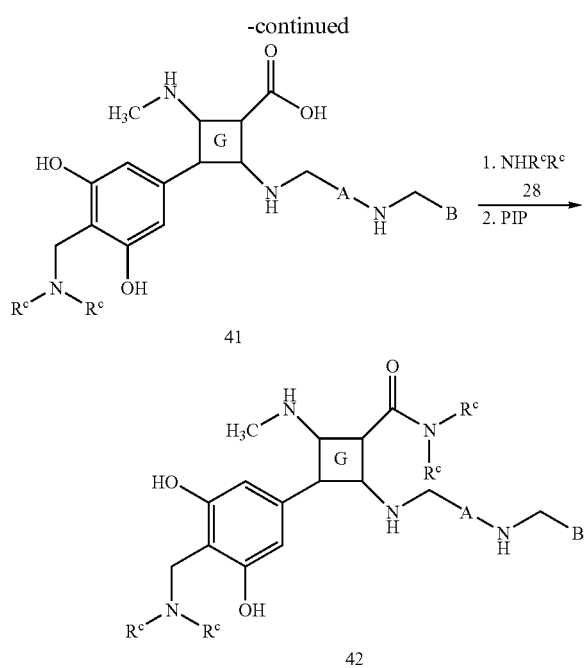

41

42

Scheme L illustrates multiple reductive alkylation reaction of a glycopeptide derivative 27 to afford glycopeptide derivative 44a.

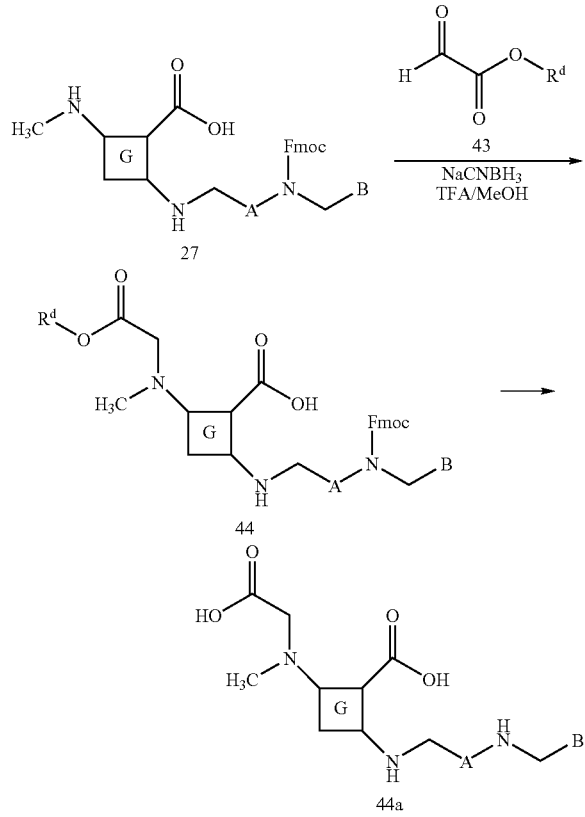

Additional details and other methods for preparing the compounds of this invention are described in the Examples below.

Pharmaceutical Compositions

This invention also includes pharmaceutical composition containing the novel glycopeptide compounds of this invention. Accordingly, the glycopeptide compound, preferably in the form of a pharmaceutically acceptable salt, can be formulated for oral or parenteral administration for the therapeutic or prophylactic treatment of bacterial infections.

By way of illustration, the glycopeptide compound can be admixed with conventional pharmaceutical carriers and excipients and used in the form of tablets, capsules, elixirs, suspensions, syrups, wafers, and the like. Such pharmaceutical compositions will contain from about 0.1 to about 90% by weight of the active compound, and more generally from about 10 to about 30%. The pharmaceutical compositions may contain common carriers and excipients, such as corn starch or gelatin, lactose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intramuscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example polyethylene glycol, a chelating agent, for example ethylenediamine tetracetic acid, and an anti-oxidant, for example, sodium metabisulphite may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses are in the general range of from 0.01-100 mg/kg/day, preferably 0.1-50 mg/kg/day. For an average 70 kg human, this would amount to 0.7 mg to 7 g per day, or preferably 7 mg to 3.5 g per day.

Other suitable formulations for use in the present invention can be found in *Remington's Pharmaceutical Sciences, Mace Publishing Company*, Philadelphia, Pa., 17th ed. (1985).

The following formulation examples illustrate representative pharmaceutical compositions of the present invention.

FORMULATION EXAMPLE A

This example illustrates the preparation of a representative pharmaceutical composition for oral administration of a compound of this invention:

| Ingredients | Quantity per tablet, (mg) |
| --- | --- |
| Active Compound | 200 |
| Lactose, spray-dried | 148 |
| Magnesium stearate | 2 |

The above ingredients are mixed and introduced into a hard-shell gelatin capsule.

FORMULATION EXAMPLE B

This example illustrates the preparation of another representative pharmaceutical composition for oral administration of a compound of this invention:

| Ingredients | Quantity per tablet, (mg) |
| --- | --- |
| Active Compound | 400 |
| Cornstarch | 50 |
| Lactose | 145 |
| Magnesium stearate | 5 |

The above ingredients are mixed intimately and pressed into single scored tablets.

FORMULATION EXAMPLE C

This example illustrates the preparation of a representative pharmaceutical composition for oral administration of a compound of this invention.

An oral suspension is prepared having the following composition.

| Ingredients | |
| --- | --- |
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 mL |

FORMULATION EXAMPLE D

This example illustrates the preparation of a representative pharmaceutical composition containing a compound of this invention.

An injectable preparation buffered to a pH of 4 is prepared having the following composition:

| Ingredients | |
| --- | --- |
| Active Compound | 0.2 g |
| Sodium Acetate Buffer Solution (0.4 M) | 2.0 mL |
| HCl (1N) | q.s. to pH 4 |
| Water (distilled, sterile) | q.s. to 20 mL |

FORMULATION EXAMPLE E

This example illustrates the preparation of a representative pharmaceutical composition for injection of a compound of this invention.

A reconstituted solution is prepared by adding 20 mL of sterile water to 1 g of the compound of this invention. Before use, the solution is then diluted with 200 mL of an intravenous fluid that is compatible. with the active compound. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection

FORMULATION EXAMPLE F

This example illustrates the preparation of a representative pharmaceutical composition for topical application of a compound of this invention.

| Ingredients | grams |
| --- | --- |
| Active compound | 0.2-10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

FORMULATION EXAMPLE G

This example illustrates the preparation of a representative pharmaceutical composition containing a compound of this invention.

A suppository totaling 2.5 grams is prepared having the following composition:

| Ingredients | |
| --- | --- |
| Active Compound | 500 mg |
| Witepsol H-15* | balance |

(*triglycerides of saturated vegetable fatty acid; a product of Riches-Nelson, Inc., New York, N.Y.)

Utility

The glycopeptide compounds of this invention, and their pharmaceutically acceptable salts, are useful in medical treatments and exhibit biological activity, including antibacterial activity, which can be demonstrated in the tests described in the Examples. Such tests are well known to those skilled in the art, and are referenced and described in Lorian "Antibiotics in Laboratory Medicine", Fourth Edition, Williams and Wilkins (1991), which is hereby incorporated by reference.

Accordingly, this invention provides methods for treating infectious diseases, especially those caused by Gram-positive microorganisms, in animals. The compounds of this invention are particularly useful in treating infections caused by methicillin-resistant staphylococci. Also, the compounds are useful in treating infection due to enterococci, including vancomycin-resistant enterococci (VRE). Examples of such diseases are severe staphylococcal infections, for example, staphylococcal endocarditis and staphylococcal septicemia. The animal may be either susceptible to, or infected with, the microorganism. The method comprises administering to the animal an amount of a compound of this invention which is effective for this purpose. In general, an effective amount of a compound of this invention is a dose between about 0.5 and about 100 mg/kg. A preferred dose is from about 1 to about 60 mg/kg of active compound. A typical daily dose for an adult human is from about 50 mg to about 5 g.

In practicing this method, the antibiotic can be administered in a single daily dose or in multiple doses per day. The treatment regimen may require administration over extended periods of time, for example, for several days or for from one to six weeks. The amount per administered dose or the total amount administered will depend on such factors as the nature and severity of the infection, the age and general health of the patient, the tolerance of the patient to the antibiotic and the microorganism or microorganisms in the infection.

Among other properties, the compounds of this invention have also been found to be more chemically stable compared to N-acyl glycopeptide derivatives. More specifically, it has been observed that acylation of the amino group of the vancosamine moiety of vancomycin increases the rate of hydrolysis of the disaccharide moiety. In contrast, when the compounds of this invention are substituted on the amino group of the vancosamine moiety of vancomycin with a —$R^a$—Y—$R^b$—$(Z)_x$ group, no increase in the rate of hydrolysis of the disaccharide moiety is observed.

The following synthetic and biological examples are offered to illustrate this invention and are not to be construed in any way as limiting the scope of this invention.

EXAMPLES

In the examples below, the following abbreviations have the following meanings. Any abbreviations not defined have their generally accepted meaning. Unless otherwise stated, all temperatures are in degrees Celsius.

| | |
| --- | --- |
| BOC, Boc = | tert-butoxycarbonyl |
| DIBAL-H = | diisobutylaluminum hydride |
| DIPEA = | diisopropylethylamine |
| DMF = | N,N-dimethylformamide |
| DMSO = | dimethyl sulfoxide |
| eq. = | equivalent |
| Et = | ethyl |
| EtOAc = | ethyl acetate |
| Fmoc = | 9-fluorenylmethoxycarbonyl |
| HOBT = | 1-hydroxybenzotriazole hydrate |
| Me = | methyl |
| PyBOP = | benzotriazol-1-yloxytris(pyrrolidino)phosphonium hexafluorophosphate |
| TEMPO = | 2,2,6,6-tetramethyl-piperidinyloxy free radical |
| TFA = | trifluoroacetic acid |
| THF = | tetrahydrofuran |
| TLC, tlc = | thin layer chromatography |

In the following example, vancomycin hydrochloride semi-hydrate was purchased from Alpharma, Inc. Fort Lee, N.J. 07024 (Alpharma AS, Oslo Norway). Other reagents and reactants are available from Aldrich Chemical Co., Milwaukee, Wis. 53201

General Procedure A

Reductive Alkylation of Vancomycin

To a mixture of vancomycin (1 eq.) and the desired aldehyde (1.3 eq.) in DMF was added DIPEA (2 eq.). The reaction was stirred at ambient temperature for 1-2 hours and monitored by reverse-phase HPLC. Methanol and NaCNBH$_3$ (1 eq.) were added to the solution, followed by TFA (3 eq.). Stirring was continued for an additional hour at ambient temperature. After the reaction was complete, the methanol was removed in vacuo. The residue was precipitated in acetonitrile. Filtration gave the crude product which was then purified by reverse-phase HPLC If desired, other glycopeptides may be used in this procedure.

General Procedure B

Aglycon Alkylation Procedure I

A white suspension of vancomycin aglycon TFA salt (1.0 eq.), Cs$_2$CO$_3$ (3.5 eq.) in DMF is stirred at room temperature for 30 min. An alkyl halide (1.1 eq.) is added. The reaction mixture is then stirred for 5-24 h before quenching with acetic acid. The resulting brownish solution is dripped into water to give a white precipitate. Filtration affords the crude monoalkylated product which can be purified by reverse-phase HPLC if desired.

General Procedure C

Aglycon Alkylation Procedure II

Under nitrogen, the trifluoroacetate salt of vancomycin aglycone (1 eq) is dissolved in DMF and stirred vigorously at room temperature with potassium carbonate (8-10 eq) for an hour. An alkyl halide (1 eq) is added and the mixture is stirred vigorously overnight. The crude product is collected by precipitation into diethyl ether, washed with acetonitrile and taken up in 10% aqueous acetic acid The mono-alkylated product is obtained upon reverse-phase HPLC purification.

General Procedure D

Preparation of Amino-Substituted Aldehydes

A solution of an aminoacetal (1 eq), such as 2-aminoacetaldehyde dimethyl acetal, an aldehyde (1.05 eq), and NaCNBH$_3$ (1 eq) in CH$_2$Cl$_2$ is stirred at room temperature for 1-4 hours. The reaction is monitored by TLC. To the reaction mixture are added FmocCl (1 eq) and DIPEA (2 eq) at 0° C. Stirring is continued for 1-2 hours at room temperature. The reaction is then washed with 0.1 N HCl, water and brine. The solvent is removed in vacuo and the residue is purified by flash chromatography gave the amino-substituted acetal.

To the solution of above amino-substituted acetal in acetone is added 6 N HCl (1.5 eq). The reaction is stirred at room temperature for 5-16 hours. Solvent is removed in vacuo and the residue is dried under high vacuum to give crude amino-substituted aldehyde which is typically used without further purification.

General Procedure E

Preparation of Thio-Substituted Aldehydes

A solution of a bromoacetal (1 eq), such as dimethyl 2-bromoacetaldehyde, and sodium iodide (1 eq) in DMF is stirred at ambient temperature for 0.5 h. To the solution is added a substituted thiol (1 eq), such as n-decyl thiol, followed by potassium carbonate (1 eq). The mixture is stirred at 25-80° C. for 4-16 hours. The reaction is then taken up with ethyl acetate, washed twice with water and once with sat. NaCl. The organic layer is dried over MgSO$_4$ and the solvent is removed in vacuo. Purification on flash chromatography (hexan:ethyl acetate=8:1) provides the corresponding thio-substituted acetal.

To a solution of the thio-substituted acetal in acetone was added 6 N HCl (1.5 eq). The reaction is stirred at room temperature for 5-16 hours. The solvent is removed in vacuo and the residue is dried under high vacuum to give crude thio-substituted aldehyde which is typically used without further purification.

General Procedure F

Preparation of Thio-Substituted Aldehydes

A mixture of a thiol ester (1 eq), such as methyl thioglycolate, sodium iodide (1 eq), an alkyl bromide (1 eq) and potassium carbonate (1 eq) in DMF is stirred at room temperature for 4-16 hours. The reaction is taken up with ethyl acetate and washed with water and brine. The organic layer is dried over magnesium sulfate and solvent is removed in vacuo. Purification on flash chromatography provides the thio-substituted ester.

The thio-substituted ester in dry ether is treated with DIBAL-H (1 M solution in cyclohexane, 1.3 eq) at −78° C. The reaction is then stirred at −78° C. for 2-4 hours. TLC is used to monitor the reaction progress. Upon completion, ethyl formate (0.5 eq) is added to quench the reaction. The reaction is then washed with 10% acetic acid, water and brine. The organic layer is dried over magnesium sulfate and the solvent removed to afford the crude thio-substituted aldehyde which is typically used without further purification.

General Procedure G

Preparation of Alkoxy-Substituted Aldehydes

A solution of a hydroxyacetal (1 eq), such as dimethyl 2-hydroxyacetaldehyde, in THF is treated with sodium hydride (1 eq) at 0° C. After hydrogen evolution ceases, an alkyl bromide is added at 0° C. The reaction is then stirred at room temperature for 1-4 hours. The reaction is taken up with ethyl acetate and washed with water and brine. The solvent is removed in vacuo and the residue typically purified by flash chromatography to afford the alkoxy-substituted acetal.

To a solution of the alkoxy-substituted acetal in acetone is added 6 N HCl (1.5 eq). The reaction is stirred at room temperature for 5-16 hours. The solvent is removed in vacuo and the residue is dried under high vacuum to give crude alkoxy-substituted aldehyde which is typically used without further purification.

General Procedure H

Preparation of Sulfonamido-Substituted Aldehydes

A solution of an aminoacetal (1 eq), such as dimethyl 2-aminoacetaldehyde, and diisopropylethylamine (2 eq) in THF is treated with a sulfonyl chloride (1 eq) at 0° C. The reaction is then stirred at room temperature for 1-4 hours. The reaction is then taken up with ethyl acetate and washed with 0.1 N HCl, water and brine. The solvent is removed in vacuo and the residue purified by flash chromatography gave the sulfonamido-substituted acetal.

To a solution of the sulfonamido-substituted acetal in acetone is added 6 N HCl (1.5 eq). The reaction is stirred at room temperature for 5-16 hours. The solvent is then removed in vacuo and the residue is dried under high vacuum to give crude sulfonamido-substituted aldehyde which is typically used without further purification.

Example A

Preparation of Fmoc-Aminoacetaldehyde

Fmoc-protected aminoethanol was prepared from aminoethanol by conventional techniques (e.g., as described in Examples B and C below).

To a mixture of Fmoc-aminoethanol (37.64 g, 133 mmol, 1.0 equiv), TEMPO (0.008 M in $CH_2Cl_2$, 332.5 mL, 2.66 mmol, 0.02 equiv), KBr (0.5 M in water, 53.2 mL, 26.6 mmol, 0.2 equiv) and ethyl acetate (1,500 mL), at 0° C., was added NaOCl (0.35 M, buffered to pH 8.6 by $NaHCO_3$, 760 mL, 266 mmol, 2.0 equiv). A mechanical stir was used to ensure efficient stirring, and the reaction was monitored by TLC. After 20 min, the two layers were separated. The aqueous layer was extracted with ethyl acetate (2×250 mL), the combined organic layers were washed with saturated $Na_2S_2O_3$, water, and brine, dried over $Na_2SO_4$, filtered and concentrated to about 400 mL. Hexane (1,600 mL) was added to give a white precipitate. After filtration, Fmoc-aminoacetaldehyde (25.2 g, 67%) was collected as a white powder.

Example B

Preparation of N-Fmoc-2-(n-Decylamino)acetaldehyde

To a solution of n-decanoyl chloride (2.7 mL, 13 mmol, 1.0 eq) in methylene chloride (20 mL) in an ice/acetone bath was added a mixture of glycine methyl ester hydrochloride (2.0 g, 16 mmol, 1.2 eq) and DIPEA (5.1 mL, 29 mmol, 2.2 eq) in methylene chloride (20 mL) dropwise. The reaction was stirred a further 60 min after complete addition, then washed with 3N hydrochloric acid (50 mL) twice, followed by saturated sodium bicarbonate (50 mL). The organics were dried over magnesium sulfate and the solvents removed under reduced pressure. Methyl 2-Decylamidoacetate (3.0 g, 12 mmol, 95%) was obtained which was used in the next step without further purification.

Under nitrogen, methyl 2-(n-decylamido)acetate (3.0 g, 12 mmol, 1.0 eq) was dissolved in anhydrous tetrahydrofuran (25 mL) and cooled in an ice bath. A solution of lithium aluminum hydride (1 N, 25 mL, 25 mmol, 2.0 eq) was added carefully. The resulting solution was refluxed under nitrogen overnight, then cooled in an ice bath. Tetrahydrofuran (50 mL) was added followed by slow addition of sodium sulfate decahydrate until effervescence ceased. The mixture was allowed to warm to room temperature, filtered, then concentrated under vacuum. 2-(n-Decylamino)ethanol (2.3 g, 11 mmol, 93%) was obtained which was used without further purification.

2-(n-Decylamino)ethanol (2.3 g, 11 mmol, 1.1 eq) and DIPEA (2.0 mL, 11 mmol, 1.1 eq) were dissolved in methylene chloride (15 mL) and cooled in an ice bath. 9-Fluorenylmethyl chloroformate (2.6 g, 10 mmol, 1.0 eq) in methylene chloride (15 mL) was added, the mixture stirred for 30 minutes then washed with 3N hydrochloric acid (50 mL) twice and saturated sodium bicarbonate (50 mL). The organics were dried over magnesium sulfate, and the solvents removed under reduced pressure. N-Fmoc-2-(decylamino)ethanol (4.6 g, 11 mmol, 108%) was used without further purification.

N-Fmoc-2-(n-Decylamino)ethanol (4.6 g, 11 mmol, 1.0 eq) and DIPEA (7.6 mL, 44 mmol, 4.0 eq) were dissolved in methylene chloride (30 mL) and cooled in an ice/acetone bath. A solution of sulfur trioxide pyridine complex (6.9 g, 43 mmol, 4.0 eq) in dimethyl sulfoxide (30 mL) was added, and the solution stirred for 20 minutes. Crushed ice was added and the mixture partitioned. The organics were washed with 3N hydrochloric acid twice, saturated sodium bicarbonate and saturated sodium chloride, dried over magnesium chloride, and concentrated under vacuum. N-Fmoc-2-(n-Decylamino)acetaldehyde (3.4 g, 8 mmol, 74%) was used without further purification (see example 5).

Example C

Preparation of 2-(Decylamino)ethanol

A solution of aminoethanol (30.5 g, 500 mmol, 30.1 mL) and 1-bromodecane (27.65 g, 125 mmol, 26 mL) in ethanol was stirred at 65° C. for 4 hr. The solvent was removed under reduced pressure. The residue was diluted with EtOAc (800 mL) and the organic solution was washed with 10 (2×200 mL); saturated aqueous $NaHCO_3$ (200 mL) and saturated brine (200 mL). The organic phase was dried over anhydrous $Na_2SO_4$, and concentrated under reduced pressure. The resulting crude product, 2-(decylamino)ethanol, was used without further purification.

Example D

Preparation of N-Fmoc-2-(trans-Dec-4-en-1-ylamino)acetaldehyde trans-4-Decenal (7.2 g, 46.6 mmol) was mixed with 40 mL (0-37 moL) of aminoacetaldehyde dimethylacetal in 400 µL of methanol and stirred at room temperature for 30 minutes. $NaCNBH_3$ (2.9 g, 46.6 mmol) was added, the reaction was cooled in an ice bath, and 27 mL (0.35 moL) of TFA was added dropwise over 5 minutes. The ice bath was then removed and the reaction was stirred for 70 minutes at room temperature, concentrated to a third of its volume, and partitioned between ethyl acetate (250 mL) and 1N NaOH (200 mL). The organic layer was washed with water (3×75 mL), dried over MgSO4, filtered and concentrated under reduced pressure to yield 11.1 g (45-6 mmol) of 2-(trans-dec-4-en-t-ylamino)acetaldehyde dimethyl acetal as a yellow oil that was used directly in the next step.

2-(trans-Dec-4-en-1-ylamino)acetaldehyde dimethyl acetal (10.5 g, 43.2 mmol) was mixed with dichloromethane (300 mL) and 7.5 mL (43.2 mmol) diisopropylethyl amine and 11.2 g (43.2 mmol) of FMOC-Cl was added portionwise. The reaction was stirred at room temperature for 3 hours and then poured into a solution of 10% $KHSO_4$ (200 mL). The organic layer was washed with water (200 µL), dried over MgSO₄, and concentrated under reduced pressure. The resulting oil was chromatographed on silica gel in 10% EtOAc/Hexanes to give 16.1 g (34.6 mmol) of N-Fmoc-2-(trans-dec-4-en-1-ylamino)acetaldehyde dimethyl acetal as a clear oil that was used directly in the next step.

N-Fmoc-2-(trans-Dec-4-en-1-ylamino)acetaldehyde dimethyl acetal (5 g, 10.7 mmol) was mixed with 30 mL of TFA and stirred at room temperature for 30 minutes. The reaction was poured into water (140 mL) and centrifuged to obtain a clear oil. The supernatant was decanted and the oil was mixed with 40 mL of water and centrifuged again. The supernatant was again decanted and the oil was dissolved in dichloromethane (100 mL), dried over MgSO4, filtered, and concentrated under reduced pressure to obtain 5.2 g (12.3 mmol) of N-Fmoc-2-(trans-Dec-4-en-1-ylamino)acetaldehyde as a clear oil.

Example E

Preparation of a Compound of Formula V

Where $R^{22}$ is OH and $R^{23}$ is —CH$_2$—N—(N—CH$_3$-D-glucamine)

Vancomycin (9.0 g, 5-16 mmol) was added to a solution of N-methyl-D-glucamine (5.03 g, 25.8 mmol) and 37% formaldehyde (0.43 mL, 5.4 mmol) in 50% aqueous acetonitrile (60 mL) under nitrogen and stirred at room temperature. After 4 hours, the acetonitrile was removed in vacuo, water (30 mL) was added, and the pH was adjusted to ~4 with 10% trifluoroacetic acid. The solution was purified by reverse-phase HPLC. Fractions containing the desired product were identified by mass spectrometry, pooled, and lyophilized to give the title compound as a white powder. This intermediate may be further derivatized using the procedures described herein.

Example F

Preparation of a Compound of Formula IV

Where $R^{15}$ and $R^{16}$ are H, $R^{22}$ is OH and $R^{27}$ is —CH$_2$CH$_2$—NH-Fmoc Vancomycin hydrochloride (4.00 g, 2.60 mmol) was suspended in 40 mL of 1,3-dimethyl-3,4,5,6-tetrahydro-2-(1H)-pyrimidinone and heated to 70° C. for 15 minutes. N-(9-fluorenylmethoxycarbonyl)aminoacetaldehyde (720 mg, 2.6 mmol) was added and the mixture was heated at 70° C. for one hour. Sodium cyanoborohydride (160 mg, 2.5 mmol) in 2 mL methanol was added and the mixture was heated at 70° C. for 2 hours, then cooled to room temperature. The reaction solution was added dropwise to 20 mL of acetonitrile, giving a precipitate that was collected by centrifugation. The precipitate was purified by reverse-phase HPLC on a Ranin C18 Dynamax column (2.5 cm×25 cm, 8 µm particle size), at 10 mL/min flow rate using 0.045% TFA in water as buffer A and 0.045% TFA in acetonitrile as buffer B (HPLC gradient of 10-70% B over 90 minutes), which yielded the title intermediate as its trifluoroacetate salt. MS calculated: MH⁺, 1715; Found, 1715.

This compound can be deprotected and further derivatized, for example, via reductive alkylation, as described herein.

Example G

Preparation of an O-Ethyl Aglycone Derivative

Vancomycin hydrochloride hydrate (10 g, 6.4 mmol) was dissolved in 100 mL of dimethyl sulfoxide (DMSO) and 3-(dimethylamino)propylamine (3.2 mL, 26 mmol) was added. PyBOP (3.3 g, 6.4 mmol) and 1-hydroxybenzotriazole (HOBT, 0.9 g, 6.4 mmol) dissolved in 100 mL N,N-dimethylformamide (DMF) was added dropwise at room temperature. The reaction was stirred for one hour and dripped into acetonitrile to give a white precipitate, which was filtered and washed with acetonitrile, ether and dried under vacuum to give a syrup of crude vancomycin 3-(dimethylamino)propyl amide.

A portion of this syrup was dissolved in 100 mL trifluoroacetic acid (TFA), heated at 323K for 2 hours, cooled to room temperature and added dropwise to ether, resulting in a green precipitate. The precipitate was collected by filtration, dried under vacuum and purified by reverse-phase HPLC (2-50% acetonitrile in water containing 0.1% TFA) to give vancomycin 3-(dimethylamino)propyl amide aglycone, as its TFA salt.

The aglycone, as its trifluoroacetate salt (500 mg, 340 umol) was dissolved in 5 mL DMF and potassium carbonate (500 mg, 3.6 mmol) was added. The mixture was stirred for 15 minutes at room temperature then tert-butyl N-(2-bromoethyl)carbamate (77 mg, 340 umol) was added. The mixture was stirred at room temperature for 24 hours, then additional tert-butyl N-(2-bromoethyl)carbamate (70 mg, 310 umol) was added. The mixture was stirred at room temperature for 7 hours then dripped into ether giving a precipitate that was collected by centrifugation, washed with acetonitrile and dissolved in 5:1:2 water/acetic acid/acetonitrile. This solution was purified by reverse-phase HPLC giving vancomycin 3-(dimethylamino)propyl amide O-2-(N-t-BOC-amino) ethoxy aglycone as the trifluoroacetate salt, which was treated with 1 mL TFA for 30 minutes at room temperature. Reverse-phase HPLC purification yielded vancomycin 3-(dimethylamino)propyl amide O-(2-aminoethyl) aglycone as the trifluoroacetate salt. This compound can be deprotected and further derivatized, for example, via reductive alkylation, as described above.

Example 1

Synthesis of a Compound of Formula III

Where $R^{15}$ is —CH$_2$CH$_2$—NH—(CH$_2$)$_9$CH$_3$, $R^{17}$ is H and $R^{22}$ is OH To an oven-dried, 1000 mL round bottomed flask, equipped with magnetic stirring bar, were added vancomycin (34.1 g, 23 mmol, 1 eq), N-Fmoc-aminoacetaldehyde (6-5 g, 23 mmol, 1 eq), DIPEA (8.5 mL, 46 mmol, 2 eq) and DMF (340 mL). The mixture was stirred at ambient temperature over 2 hours, and monitored by HPLC. The reaction became homogenous, and ~90% conversion to the imine was observed. Methanol (340 mL) and NaCNBH₃ (4.3 g, 69 mmol, 3 eq) were added to the solution, followed by TFA (5.2 mL, 69 mmol, 3 eq). Stirring was continued for an additional hour at ambient temperature. After the reaction was complete, methanol was removed in vacuo. The residue containing the crude product and DMF was slowly poured into a 5 L flask and stirred with acetonitrile (3.5 L). A white precipitate was formed. The suspension was allowed to settle at ambient temperature and the supernetant was decanted. The white solid was filtered and triturated with ether (2 L). After filtration, the crude product was dried under high vacuum overnight.

An 8×26 cm column was packed with octadecyl bonded silical gel. The column was washed with 800 mL of 90% Solvent B [acetonitrile in water, 0.1% TFA] and equilibrated with 800 mL of 10% Solvent B. Crude product (10 g) was dissolved in 30% Solvent B (150 mL, containing 2 mL of 3 N HCl) and loaded onto the column. It was then flashed with 10% B (800 mL×2), 40% B (800 mL×3) and 90% B (800 mL). The fractions were checked by analytical HPLC. After lyophilization, $N^{van}$-Fmoc-aminoethyl vancomycin was obtained as its TFA salt.

$N^{van}$-Fmoc-aminoethyl vancomycin was deprotected to give $N^{van}$-aminoethyl vancomycin tri-TFA salt using conventional procedures (e.g. as described in Examples 2 and 3)

To a solution of $N^{van}$-aminoethyl vancomycin tri-TFA salt (15.5 mg, 8.4 micromol) in methanol:DMF:THF (2:1:1, 1-6 mL) was added decanal (92 microL, 59 micromol) and sodium cyanoborohydride (0.1M in methanol, 45 microL, 4.5 micromol). After 45 minutes, the solvents were removed in vacuo, and the residue purified by preparative HPLC. The appropriate fractions were combined and lyophylized to give $N^{van}$-2-(n-decylamino)ethyl vancomycin (2.4 mg) as a white powder. Also isolated was $N^{van},N^{van}$-bis-2-(n-decylamino) ethyl vancomycin (2.9 mg).

Example 2

Synthesis of a Compound of Formula III

Where $R^{15}$ is —CH$_2$CH$_2$—NH—(CH$_2$)CH$_3$, $R^{17}$ is H and $R^{22}$ is OH Vancomycin hydrochloride (12 g, 7.7 mmol, 1.0 eq), N-Fmoc-2-(n-decylamino)acetaldehyde (3.2 g, 7.6 mmol, 1.0 eq) and DIPEA (2.6 mL, 14.9 mmol, 2.0 eq) were stirred at room temperature in DMF (120 mL) for 90 minutes. Sodium cyanoborohydride (1.4 g, 22 mmol, 3.0 eq) was added, followed by methanol (120 mL) then trifluoroacetic acid (1.8 mL, 23 mmol, 3.0 eq). The mixture was stirred for 60 minutes at room temperature, then the methanol removed under reduced pressure. The resulting solution was added to 600 mL diethyl ether giving a precipitate which was filtered, washed with ether, and dried under vacuum. The crude product was purified on a reverse-phase flash column, eluting with 10, 20, 30% acetonitrile in water (containing 0.1% trifluoroacetic acid) to remove polar impurities (such as residual vancomycin) then the product was eluted with 70% acetonitrile in water (containing 0.1% trifluoroacetic acid) to give 9 g of $N^{van}$—(N-Fmoc-2-n-decylaminoethyl) vancomycin as its trifluoroacetate salt (4.3 mmol, 56%).

$N^{van}$—(N-Fmoc-2-n-decylaminoethyl) vancomycin (100 mg) was dissolved in 1 mL DMF (1 mL) and treated with piperidine (200 uL) for 30 minutes. The mixture was precipitated into ether, centrifuged and washed with acetonitrile. Reverse-phase preparative HPLC (10-70% acetonitrile in water containing 0.1% trifluoroacetic acid over 120 minutes) gave $N^{van}$-2-(n-decylamino)ethyl vancomycin as its TFA salt.

Example 3

Synthesis of a Compound of Formula III

Where $R^{15}$ is —CH$_2$CH$_2$—NH—(CH$_2$)CH$_3$, $R^{17}$ is H and $R^{22}$ is —N-(D-glucosamine)

$N^{van}$—(N-Fmoc-2-n-decylaminoethyl) vancomycin (100 mg, 48 umol, 1-0 eq) was dissolved in 1 mL DMF and glucosamine hydrochloride was added (31 mg, 144 mmol, 3.0 eq). The mixture was stirred vigorously for 30 minutes (the glucosamine hydrochloride did not fully dissolve), DIPEA (60 uL, 344 umol, 7.2 eq) was added and the mixture stirred vigorously for a further 30 minutes. A solution of benzotriazole-t-yl-oxy-tris-pyrrolidino-phosphonium hexafluorophosphate (PyBOP, 50 mg, 96 umol, 2.0 eq) and 1-hydroxybenzotriazole (14 mg, 104 umol, 2.2 eq) in 500 uL DMF was prepared. The PyBOP solution was added in 5 batches of 60 uL at intervals of 5 minutes to the vigorously stirred suspension of the other reaction components. The reaction was stirred an additional 30 minutes then precipitated into acetonitrile. The solid was collected by centrifugation, taken up in 1 mL N,N-dimethylformamide and treated with 200 uL piperidine for 30 minutes. Precipitation into ether was followed by centrifugation and the solid washed with acetonitrile. Reverse-phase preparative HPLC (10-70% acetonitrile in water containing 0.1% trifluoroacetic acid over 120 minutes) gave a compound of formula III where $R^{15}$ is —CH$_2$CH$_2$—NH—(CH$_2$)$_9$CH$_3$ and $R^{22}$ is —N-(D-glucosamine as its trifluoroacetate salt.

Example 4

Synthesis of a Compound of Formula III

Where $R^{15}$ is —CH$_2$CH$_2$—NH—(CH$_2$)$_9$CH$_3$ and $R^{22}$ is —NH—CH(COOH)CH$_2$COOH HOBt (1.47 g, 10.9 mmol), PyBOP (7.57 g, 14.6 mmol), and the bis-fluorenylmethyl ester of L-aspartic acid (TFA, 6.26 g, 10.4 mmol) were added to a well stirred solution of N"-(N-Fmoc-2-n-decylaminoethyl) vancomycin (20 g, 10.4 mmol) and DIPEA (5.44 mL, 31-2 mmol) in DMF (440 mL). The reaction was complete after 1 hr by MS. The mixture was precipitated into CH$_3$CN (4 L) and centrifuged. The supernatant was decanted and the pellet redissolved in DMF (440 mL). Piperidine (44 mL) was added and the reaction monitored by MS.

After 1 hr reaction was complete. Precipitate via dropwise addition to Et$_2$O (4 L) with continued stirring overnight. The solid was collected via filtration and dried in vacuo. The resulting solid was then triturated with CH$_3$CN and collected via filtration and dried in vacuo giving desired product as an off-white solid which was purified by reverse phase HPLC.

Example 5

Synthesis of a Compound of Formula V

Where R$^{15}$ is H and R$^{23}$ is —CH$_2$—NH—CH$_2$CH$_2$—NH—(CH$_2$)$_9$CH$_3$ To 50% aqueous acetonitrile (1.0 mL) was added diaminoethane (30 mg, 0.5 mmol), 37% formalin (7.6 uL, 0.20 mmol) and vancomycin hydrochloride (140 mg, 0.10 mmol). After stirring for 3 h, the product was precipitated by the addition of acetonitrile (12 mL) The solid was isolated by centrifugation, then washed with ether (12 mL). The resulting solid was dried in vacuo, and purified by reverse-phase HPLC (5-15% B over 40 min at a flow rate of 50 ml/min). Fractions containing the desired product were identified by mass spectrometry, pooled, and lyophilized to give a compound of formula V where R$^{23}$ is —CH$_2$—NH—CH$_2$CH$_2$NH$_2$ (85 mg) as a white powder. MS calculated (MH+), 1520; found, 1520.

To a solution of the compound from the above step (80 mg, 0.040 mmol) in ethanol (1.0 mL) and DMF (1.0 mL) was added n-decanal (6.3 mg, 0.040 mmol), and the mixture was stirred for 45 minutes. Sodium cyanoborohydride (0.1 M in methanol, 400 uL, 0.040 mmol) was then added and the mixture stirred for 3 hours. The solvents were removed in vacuo, and the residue purified by preprative HPLC. Fractions containing the desired product were identified by mass spectrometry, pooled, and lyophilized to the title compound as a white powder. MS calculated (MH+), 1661; found, 1661.

Example 6

Synthesis of a Compound of Formula V

Where R$^{15}$ is —CH$_2$—NH—CH$_2$CH$_2$—NH—(CH$_2$)$_9$CH$_3$ R$^{22}$ is —N-(D-glucosamine) and R$^{23}$ is —CH$_2$—N—(N—CH$_3$-D-glucainine)

To 50% aqueous acetonitrile (10 mL) was added sequentially N-methyl-D-glucamine (975 mg, 5.0 mmol), 37% formalin (84 uL, 1.1 mmol), DIPEA (348 uL, 2-0 mmol) and N$^{van}$—(N-Fmoc-2-n-decylaminoethyl) vancomycin (2.15 g, 1.030 mmol). After stirring for 16 h, the product was precipitated by the addition of acetonitrile (80 mL). The solid was isolated by centrifugation, then washed with acetonitrile (80 mL). The solid was dissolved in DMF (6.0 mL) and piperidine (2.0 mL). After 30 minutes, the product was precipated by the addition of acetonitrile (80 mL). The solid was isolated by centrifugation, then washed with ether (80 mL). The resulting solid was dried in vacuo, and purified by reverse-phase HPLC (10-35% B) over 40 min at a flow rate of 50 mL/min). Fractions containing the desired product were identified by mass spectrometry, pooled, and lyophilized to give a compound of formula V where R$^{15}$ is —CH$_2$—NH—CH$_2$CH$_2$—NH—(CH$_2$)$_9$CH$_3$ and R$^{23}$ is —CH$_2$—N—(N—CH$_3$-D-glucamine (1.34 g) as a white powder. MS calculated (MH+), 1839; found, 1839.

The above compound (tetra TFA salt) (150 mg, 0.065 mmol) was dissolved in DMF. To this solution was added sequentially D-glucosamine hydrochloride (35 mg, 0.16 mmol), DIPEA (65 uL, 0.32 mmol), and a solution of PyBOP and HOBt in DMF (3.85 mL of a solution 0.02 M in each, 0.077 mmol each). After 30 minutes, the product was precipated by the addition of acetonitrile (40 mL). The solid was isolated by centrifugation, then washed with acetonitrile (40 mL). The resulting solid was dried in vacuo, and purified by reverse-phase HPLC (10-35% B over 40 min at a flow rate of 50 mL/min). Fractions containing the desired product were identified by mass spectrometry, pooled, and lyophilized to the title compound as a white powder. MS calculated (MH+), 2000; found, 2000.

Example 7

Synthesis of a Compound of Formula IV

Where R$^{15}$ is —CH$_2$—NH—CH$_2$CH$_2$—NH—(CH$_2$)$_9$CH$_3$ R$^{22}$ is —OH and R$^{27}$ is —CH$_2$C(O)OCH$_2$CH$_3$ A solution of vancomycin monohydrochloride (3.72 g, 2.5 mmol) in DMF (35 mL) was treated with diisopropylethylamine (0.87 mL, 5.0 mmol) followed by N-Fmoc-n-decylaminoacetaldehyde (1.05 g, 2.5 mmol). The resulting reaction mixture was stirred at room temperature for 12 hours Ethyl glyoxylate(2.5 mmol, 50% solution in toluene) was added and the reaction solution was stirred at 50° C. for 6 hours. The reaction mixture was cooled to room temperature and was treated with NaCNBH$_3$ (0.376 g, 6.0 mmol) followed by a solution of TFA (0.58 mL, 7.5 mmol) in MeOH (35 mL). After 20 min, MeOH was removed under reduced pressure and the crude was precipitated in acetonitrile (400 mL). The solid was collected by filtration. The crude was purified by preparative HPLC to give title compound. MS (M+H) 1939.2 (M+, calculated 1938.7)

Example 8

Synthesis of a Compound of Formula IV

Where R$^{15}$ is —CH$_2$—C(O)OCH$_3$, R$^{22}$ is —OH and R$^{27}$ is —CH$_2$C(O)OCH$_3$ A solution of vancomycin hydrochloride (7.43 g, 5.0 mmol) in DMSO (100 mL) was treated with diisopropylethylamine (1.74 mL, 10.0 mmol) followed by methyl bromoacetate (0.842 g, 5.5 mmol) at room temperature. The reaction mixture was stirred at room temperature overnight. The crude product was precipitated using acetonitrile (1000 mL). The crude product was collected and purified by preparative HPLC to provide the title product. MS (M+H) 1522.0 (M+, calculated 1519.45).

Example 9

Synthesis of a Compound of Formula VIII

Where $R^{19}$ is —CH, —C(O)OC(CH$_3$)$_3$

Under nitrogen, the trifluoroacetate salt of vancomycin aglycone (385 mg, 310 umol) was dissolved in N,N-dimethylformamide (4 mL) Potassium carbonate (400 mg, 2-9 mmol) was added and the mixture was stirred vigorously at room temperature with for 55 minutes. tert-Butyl chloroacetate (44 uL, 310 umol) was then added and the mixture stirred vigorously overnight. The crude reaction mixture was precipitated into diethyl ether (40 mL) and the solids were collected by centrifugation, washed with acetonitrile (40 mL) and taken up in 10% aqueous acetic acid. The title compound was obtained upon reverse-phase HPLC purification (calculated mass: 1256-4, observed (M+H): 1257.7).

Example 10

Synthesis of a Compound of Formula VIII

Where $R^{19}$ is —CH$_2$CH$_2$CH$_2$—NH—(CH$_2$)$_9$CH$_3$

A white suspension of vancomycin aglycon TFA salt (2.0 g, 1.59 mmol, 1.0 eq) Cs$_2$CO$_3$ (1.81 g, 5.56 mmol, 3.5 eq) and DMF (34.0 mL) was stirred at room temperature for 30 min. Then 1-butyl N-(3-iodopropyl)carbamate (0.54 g, 1.9 mmol, 1.2 eq) was added. The reaction mixture was stirred for 24 h before quenching with acetic acid. The resulting brownish solution was dripped into water to give a white precipitate. Vacuum filtration gave 1.5 g a white crystalline solid which was used for next step without further purification.

To a mixture of the above compound (1.05 g, 0.75 mmol, 1.0 eq), DIPEA (0.65 mL, 3.75 mmol, 5.0 eq) and DMF (10 mL), was added Fmoc-Cl (0.19 g, 0.75 mmol, 1.05 eq) in portions. After stirring at room temperature for 4 h, TFA (0.6 mL) was added to quench the reaction. Then the reaction mixture was dripped into 500 mL of water to give a white precipitate. Filtration gave 1.1 g of a white crystalline solid which was used for next step without further purification.

The above compound (1.17 g) was dissolved in 5 mL of TFA, stirred at room temperature for 2 h. Then the reaction mixture was dripped into 200 mL of water to give a white precipitate. Filtration gave 0.95 g of a brownish solid which was used for next step without further purification.

To a mixture of the above compound (100 mg, 0.065 mmol, 1.0 eq), and decanal (26 µL, 0.13 mmol, 2.0 eq) in DMF (1 mL) was added DIPEA (34 µL, 0.20 mmol, 3.0 eq). The reaction was stirred at ambient temperature for 1 h. Then methanol (1 mL) and NaCNBH$_3$ (9 mg, 0.13 mmol, 2.0 eq) was added to the solution, followed by TFA (20 µL, 0.26 mmol, 4.0 eq). Stirring was continued for 1 h at room temperature. After the reaction was completed, the reaction mixture was precipitateed in acetonitrile. Filtration gave a white crystalline solid which was used for next step without further purification.

The above compound was dissolved in 3 mL on DMF, addition of 0.5 mL of piperidine gave a light brownish solution. After stirring at ambient temperature for 2 h, reaction mixture was triturated in acetonitrile to give a white solid, a reverse-phase HPLC purification gave the title compound. MS (M+H) calculated: 1342.3; observed: 1342.8.

Using the above procedures and the appropriated starting materials the compounds shown in Tables I-VI were prepared. The mass spectral data for these compounds were as follows:

| Compound No. | MW (free base) | Observed MH$^+$ |
|---|---|---|
| 1 | 1632.6 | 1632.7 |
| 2 | 1772.9 | 1774.5 |
| 3 | 1604.6 | 1605.6 |
| 4 | 1576.5 | 1577.5 |
| 5 | 1582.5 | 1583.4 |
| 6 | 1658.6 | 1659.3 |
| 7 | 1693.0 | 1693.1 |
| 8 | 1618.6 | 1619.2 |
| 9 | 1588.5 | 1589.1 |
| 10 | 1632.6 | 1634.0 |
| 11 | 1632.6 | 1633.1 |
| 12 | 1632.6 | 1634.0 |
| 13 | 1646.6 | 1647.2 |
| 14 | 1630.6 | 1631.6 |
| 15 | 1628.6 | 1626.9 |
| 16 | — | — |
| 17 | 1630.6 | 1631.9 |
| 18 | — | — |
| 19 | 1716.8 | 1718.2 |
| 20 | 1857.0 | 1859.2 (M + 2H) |
| 21 | 1793.8 | 1794.9 |
| 22 | 1747.7 | 1747.4 |
| 23 | 1854.2 | 1854.0 |
| 24 | 1779.7 | 1780.5 |
| 25 | 1789.7 | 1789.0 |
| 26 | — | — |
| 27 | 1763.7 | 1764.6 |
| 28 | 1646.6 | 1646.0 |
| 29 | 1646.6 | 1646.4 |
| 30 | 1647.6 | 1646.7 |
| 31 | 1647.6 | 1646.6 |
| 32 | 1646.6 | 1645.5 |
| 33 | 1619.5 | 1618.5 |
| 34 | 1668.6 | 1667.4 |
| 35 | 1669.6 | 1669.2 |
| 36 | 1649.7 | 1648.7 |
| 37 | 1618.5 | 1619.9 |
| 38 | 1632.6 | 1631.9 |
| 39 | 1660.6 | 1661.6 |
| 40 | 1604.5 | 1605.5 |
| 41 | 1618.5 | 1619.9 |
| 42 | 1632.6 | 1633.7 |
| 43 | 1758.8 | 1760.1 |
| 44 | — | — |
| 45 | — | — |
| 46 | — | — |
| 47 | — | — |
| 48 | — | — |
| 49 | — | — |
| 50 | — | — |
| 51 | 1739.8 | 1739.4 |
| 52 | — | — |
| 53 | — | — |
| 54 | 1675.7 | 1676.6 |
| 55 | — | — |
| 56 | — | — |
| 57 | — | — |
| 58 | 1719.7 | 1720.5 |
| 59 | — | — |
| 60 | — | — |
| 61 | 1689.7 | 1690.7 |
| 62 | — | — |
| 63 | 1703.7 | 1705.2 |

-continued

| Compound No. | MW (free base) | Observed MH+ |
|---|---|---|
| 64 | — | — |
| 65 | — | — |
| 66 | — | — |
| 67 | — | — |
| 68 | — | — |
| 69 | — | — |
| 70 | — | — |
| 71 | — | — |
| 72 | — | — |
| 73 | — | — |
| 74 | — | — |
| 75 | — | — |
| 76 | — | — |
| 77 | — | — |
| 78 | 1582.5 | 1583.4 |
| 79 | — | — |
| 80 | — | — |
| 81 | — | — |
| 82 | — | — |
| 83 | — | — |
| 84 | 1624.5 | 1625.9 |
| 85 | 1638.6 | 1639.4 |
| 86 | 1652.6 | 1654.1 |
| 87 | 1674.6 | 1676.0 |
| 88 | — | — |
| 89 | 1674.6 | 1676.0 |
| 90 | — | — |
| 91 | — | — |
| 92 | — | — |
| 93 | — | — |
| 94 | — | — |
| 95 | 1632.6 | 1633.7 |
| 96 | 1632.6 | 1634.0 |
| 97 | 1646.6 | 1646.9 |
| 98 | 1660.7 | 1661.9 |
| 99 | 1674.7 | 1675.7 |
| 100 | 1604.6 | 1605.6 |
| 101 | 1588.5 | 1589.1 |
| 102 | 1621.6 | 1620.6 |
| 103 | 1619.5 | 1619.1 |
| 104 | 1696.7 | 1695.8 |
| 105 | 1697.7 | 1696.9 |
| 106 | 1628.6 | 1627.2 |
| 107 | 1614.6 | 1615.2 |
| 108 | 1586.5 | 1587.2 |
| 109 | 1614.6 | 1615.2 |
| 110 | 1616.9 | 1617.8 |
| 111 | 1688.6 | 1689.8 |
| 112 | 1702.6 | 1703.9 |
| 113 | 1723.0 | 1723.8 |
| 114 | 1640.5 | 1641.8 |
| 115 | 1668.6 | 1669.4 |
| 116 | 1696.7 | 1697.6 |
| 117 | 1724.7 | 1726.2 |
| 118 | 1638.6 | 1640.0 |
| 119 | 1690.6 | 1690.6 |
| 120 | 1726.6 | 1728.3 |
| 121 | 1744.7 | 1745.7 |
| 122 | 1652.6 | 1653.2 |
| 123 | 1680.7 | 1682.9 |
| 124 | 1690.6 | 1691.3 |
| 125 | 1810.8 | 1811.0 |
| 126 | 1712.7 | 1713.4 |
| 127 | 1687.7 | 1688.3 |
| 128 | 1719.7 | 1719.2 |
| 129 | 1546.4 | 1547.1 |
| 130 | 1619.5 | 1618.5 |
| 131 | 1761.7 | 1761.2 |
| 132 | 1818.8 | 1819.2 |
| 133 | 1572.5 | 1571.1 |
| 134 | 1832.8 | 1831.3 |
| 135 | 1832.8 | 1833.0 |
| 136 | 1761.7 | 1761.3 |
| 137 | 1718.7 | 1719.9 |
| 138 | 1708.6 | 1709.1 |
| 139 | — | — |
| 140 | 1917.9 | 1916.8 |

-continued

| Compound No. | MW (free base) | Observed MH+ |
|---|---|---|
| 141 | 1703.7 | 1704.8 |
| 142 | 1807.8 | 1809.1 |
| 143 | 1775.8 | 1776.9 |
| 144 | 1873.7 | 1875.1 |
| 145 | 1809.8 | 1810.8 |
| 146 | 1703.7 | 1703.9 |
| 147 | 1674.6 | 1675.7 |
| 148 | 1665.7 | 1665.8 |
| 149 | 1653.7 | 1654.7 |
| 150 | 1690.6 | 1691.9 |
| 151 | 1731.7 | 1732.8 |
| 152 | 1743.0 | 1743.6 |
| 153 | 1704.7 | 1703.6 |
| 154 | 1809.8 | 1810.8 |
| 155 | 1759.8 | 1761.0 |
| 156 | 1535.4 | 1536.7 |
| 157 | 1637.6 | 1637.3 |
| 158 | 1743.0 | 1743.6 |
| 159 | 1696.7 | 1696.4 |
| 160 | 1757.1 | 1757.5 |
| 161 | 1884.2 | 1885.0 |
| 162 | 1838.1 | 1838.7 |
| 163 | 1758.7 | 1759.8 |
| 164 | 1660.7 | 1661.5 |
| 165 | 1760.8 | 1761.6 |
| 166 | 1857.8 | 1858.6 |
| 167 | 1783.8 | 1785.0 |
| 168 | 1887.7 | 1888.3 |
| 169 | 1813.7 | 1814.3 |
| 170 | 1776.6 | 1777.5 |
| 171 | 1738.6 | 1739.7 |
| 172 | 1654.6 | 1655.6 |
| 173 | 1670.6 | 1671.5 |
| 174 | 1624.5 | 1625.6 |
| 175 | 1662.6 | 1664.0 |
| 176 | 1640.5 | 1641.5 |
| 177 | 1682.6 | 1683.8 |
| 178 | 1638.6 | 1639.7 |
| 179 | 1688.6 | 1689.5 |
| 180 | 1684.6 | 1685.9 |
| 181 | 1624.5 | 1625.9 |
| 182 | 1736.7 | 1737.6 |
| 183 | 1721.7 | 1721.7 |
| 184 | 1783.8 | 1783.0 |
| 185 | 1883.9 | 1885.0 |
| 186 | 1878.8 | 1879.1 |
| 187 | 1716.7 | 1717.0 |
| 188 | 1800.8 | 1801.0 |
| 189 | 1802.9 | 1804.4 |
| 190 | 1792.8 | 1794.2 |
| 191 | 1840.9 | 1841.9 |
| 192 | 1766.7 | 1768.8 |
| 193 | 1807.8 | 1808.8 |
| 194 | 1780.8 | 1781.8 |
| 195 | 1765.8 | 1766.9 |
| 196 | 1808.8 | 1809.1 |
| 197 | 1775.8 | 1776.8 |
| 198 | 1829.8 | 1830.8 |
| 199 | 1809.8 | 1810.9 |
| 200 | 1844.9 | 1847.2 |
| 201 | 1778.8 | 1781.5 |
| 202 | 1803.9 | 1806.9 |
| 203 | 1786.8 | 1789.8 |
| 204 | 1729.7 | 1732.2 |
| 205 | 1796.8 | 1799.5 |
| 206 | 1750.7 | 1754.8 |
| 207 | 1892.9 | 1896.5 |
| 208 | 1851.9 | 1855.9 |
| 209 | 1865.9 | 1869.2 |
| 210 | 1841.9 | 1846.2 (M + 2H) |
| 211 | 1717.7 | 1718.7 |
| 212 | 1729.7 | 1731.0 |
| 213 | 1729.7 | 1731.0 |
| 214 | 1760.8 | 1761.0 |
| 215 | 1795.8 | 1796.4 |
| 216 | 1703.7 | 1705.1 |
| 217 | 1761.7 | 1763.4 |

-continued

| Compound No. | MW (free base) | Observed MH+ |
|---|---|---|
| 218 | 1830.8 | 1830.9 |
| 219 | 1731.7 | 1733.1 |
| 220 | 1775.8 | 1777.5 |
| 221 | 1760.8 | 1761.9 |
| 222 | 1743.7 | 1744.8 |
| 223 | 2098.1 | 2085 (M + 2H) |
| 224 | 2020.1 | 2022.2 (M + 2H) |
| 225 | 1743.0 | 1743.7 |
| 226 | 1764.7 | 1765.6 |
| 227 | 1784.7 | 1784.8 |
| 228 | 1740.6 | 1740.8 |
| 229 | 1697.7 | 1698.5 |
| 230 | 1647.6 | 1648.7 |
| 231 | 1855.5 | 1856.8 |
| 232 | 1655.6 | 1656.5 |
| 233 | 1677.7 | 1679.0 |
| 234 | 1635.6 | 1636.7 |
| 235 | 1811.8 | 1812.6 |
| 236 | 1711.7 | 1712.7 |
| 237 | 1649.7 | 1649.5 |
| 238 | 1663.7 | 1663.5 |
| 239 | 1683.7 | 1684.4 |
| 240 | 1649.7 | 1650.7 |
| 241 | 1669.7 | 1669.9 |
| 242 | 1725.8 | 1726.6 |
| 243 | 1669.7 | 1670.6 |
| 244 | 1661.7 | 1661.7 |
| 245 | 1774.5 | 1774.6 |
| 246 | 1788.6 | 1788.7 |
| 247 | 1726.1 | 1726.6 |
| 248 | 1740.1 | 1741.0 |
| 249 | 1663.7 | 1664.5 |
| 250 | 1667.7 | 1678.9 |
| 251 | 1699.7 | 1700.5 |
| 252 | 1659.7 | 1660.3 |
| 253 | 1740.1 | 1740.7 |
| 254 | 1754.1 | 1754.5 |
| 255 | 1699.6 | 1700.5 |
| 256 | 1810.8 | 1810.9 |
| 257 | 1757.6 | 1759.6 |
| 258 | 1716.7 | 1717.6 |
| 259 | 1786.7 | 1786.4 |
| 260 | 1665.7 | 1665.8 |
| 261 | 1699.7 | 1699.7 |
| 262 | 1713.7 | 1714.6 |
| 263 | 1722.1 | 1722.9 |
| 264 | 1736.2 | 1736.8 |
| 265 | 1681.7 | 1680.8 |
| 266 | 1826.8 | 1826.1 |
| 267 | 1706.7 | 1706.0 |
| 268 | 1675.7 | 1674.2 |
| 269 | 1718.7 | 1718.6 |
| 270 | 1690.6 | 1691.3 |
| 271 | 1748.7 | 1749.2 |
| 272 | 1723.7 | 1722.2 |
| 273 | 1810.8 | 1811.0 |
| 274 | 1774.7 | — |
| 275 | 1766.7 | 1768.0 |
| 276 | 1889.0 | 1898.8 |
| 277 | 1718.7 | 1719.1 |
| 278 | 1840.8 | 1842.0 |
| 279 | 1830.8 | 1830.9 |
| 280 | 1846.0 | 1846.8 |
| 281 | 1674.6 | 1675.7 |
| 282 | 1839.8 | 1840.4 |
| 283 | 1900.2 | 1900.4 |
| 284 | 1855.8 | 1857.1 |
| 285 | 2001.0 | 2001.6 |
| 286 | 1954.9 | 1954.5 |
| 287 | 1661.7 | 1662.7 |
| 288 | 1857.2 | 1857.2 |
| 289 | 1719.6 | 1720.4 |
| 290 | 1801.9 | 1803.0 |
| 291 | 1733.7 | 1735.8 |
| 292 | 1775.8 | 1776.6 |
| 293 | 1731.7 | 1732.8 |
| 294 | 1749.8 | 1750.8 |

-continued

| Compound No. | MW (free base) | Observed MH+ |
|---|---|---|
| 295 | 1735.7 | 1736.7 |
| 296 | 1749.8 | 1750.5 |
| 297 | 1746.8 | 1747.8 |
| 298 | 1832.0 | 1832.7 |
| 299 | 1769.8 | 1771.2 |
| 300 | 1788.8 | 1790.1 |
| 301 | 1774.8 | 1776.3 |
| 302 | 1875.8 | 1874.7 |
| 303 | 1903.9 | 1901.9 |
| 304 | 1954.9 | 1954.5 |
| 305 | 1855.8 | 1857.1 |
| 306 | 1855.8 | 1857.1 |
| 307 | 1915.8 | — |
| 308 | 2047.1 | 2048.6 (M + 2H) |
| 309 | 1811.8 | 1813.2 |
| 310 | 1861.0 | 1861.9 |
| 311 | 1856.9 | 1856.6 |
| 312 | 1839.8 | 1840.8 |
| 313 | 1633.6 | 1634.8 |
| 314 | 1777.7 | 1779.0 |
| 315 | 1697.7 | 1698.7 |
| 316 | 1725.7 | 1726.6 |
| 317 | 1753.8 | 1754.8 |
| 318 | 1689.7 | 1690.9 |
| 319 | 1872.9 | 1872.8 |
| 320 | 1950.3 | 1951.1 |
| 321 | 1835.8 | 1836.9 |
| 322 | 1813.8 | 1813.6 |
| 323 | 1964.3 | 1964.9 |
| 324 | 1845.8 | 1846.8 |
| 325 | 1755.7 | 1757.1 |
| 326 | 1930.3 | 1931.5 |
| 327 | 1894.9 | 1896.1 |
| 328 | 1766.8 | 1766.3 |
| 329 | 1864.8 | 1866.1 |
| 330 | 1867.9 | 1868.6 |
| 331 | 1857.7 | 1858.9 |
| 332 | 1947.8 | 1948.9 |
| 333 | 1877.8 | 1878.7 |
| 334 | 1809.8 | 1811.1 |
| 335 | 1825.8 | 1827.1 |
| 336 | 1833.9 | 1834.8 |
| 337 | 1914.9 | 1915.3 |
| 338 | 1650.6 | 1651.6 |
| 339 | 1664.7 | 1665.7 |
| 340 | 1739.7 | 1740.7 |
| 341 | 1678.7 | 1679.2 |
| 342 | 1711.7 | 1712.2 |
| 343 | 1933.8 | 1935.2 |
| 344 | 1706.8 | 1707.7 |
| 345 | 1767.8 | 1768.6 |
| 346 | 1698.7 | 1699.0 |
| 347 | 1726.7 | 1727.8 |
| 348 | 1754.8 | 1755.4 |
| 349 | 1772.7 | 1773.4 |
| 350 | 1904.9 | 1905.8 |
| 351 | 1738.8 | 1739.8 |
| 352 | 1856.9 | 1856.6 |
| 353 | 1505.4 | 1506.1 |
| 354 | 1505.4 | 1506.7 |
| 355 | 1688.8 | 1689.8 |
| 356 | 1712.7 | 1713.9 |
| 357 | 1666.6 | 1668.7 |
| 358 | 1589.6 | 1590.8 |
| 359 | 1603.6 | 1604.6 |
| 360 | 1633.6 | 1635.1 |
| 361 | 1633.6 | 1634.3 |
| 362 | 1634.5 | 1635.5 |
| 363 | 1547.5 | 1548.1 |
| 364 | 1642.6 | 1643.6 |
| 365 | 1620.5 | 1621.7 |
| 366 | 1618.6 | 1620.0 |
| 367 | 1604.6 | 1605.5 |
| 368 | 1588.6 | 1590.8 |
| 369 | 1652.6 | 1653.5 |
| 370 | 1576.5 | 1576.7 |
| 371 | 1668.6 | 1669.7 |

-continued

| Compound No. | MW (free base) | Observed MH+ |
|---|---|---|
| 372 | 1668.6 | 1669.7 |
| 373 | 1756.7 | 1758.2 |
| 374 | 1751.6 | 1753.0 |
| 375 | 1589.5 | 1590.5 |
| 376 | 1673.6 | 1674.8 |
| 377 | 1675.7 | 1676.1 |
| 378 | 1641.5 | 1642.0 |
| 379 | 1640.5 | 1640.7 |
| 380 | 1665.6 | 1666.8 |
| 381 | 1713.7 | 1714.2 |
| 382 | 1639.6 | 1641.0 |
| 383 | 1680.6 | 1682.0 |
| 384 | 1653.6 | 1654.7 |
| 385 | 1638.6 | 1638.9 |
| 386 | 1681.6 | 1683.5 |
| 387 | 1650.5 | 1651.9 |
| 388 | 1688.6 | 1704.0 |
| 389 | 1657.7 | 1659.0 |
| 390 | 1648.6 | 1650.0 |
| 391 | 1656.5 | 1657.8 |
| 392 | 1710.6 | 1711.4 |
| 393 | 1682.6 | 1683.5 |
| 394 | 1719.6 | 1720.7 |
| 395 | 1699.5 | 1698.7 |
| 396 | 1653.5 | 1654.7 |
| 397 | 1678.6 | 1679.8 |
| 398 | 1661.6 | 1661.8 |
| 399 | 1604.5 | 1605.4 |
| 400 | 1671.6 | 1672.0 |
| 401 | 1604.6 | 1605.7 |
| 402 | 1695.7 | 1696.7 |
| 403 | 1562.5 | 1562.9 |
| 404 | 1632.6 | 1634.0 |
| 405 | 1618.6 | 1619.9 |
| 406 | 1709.7 | 1710.7 |
| 407 | 1737.7 | 1738.9 |
| 408 | 1765.8 | 1766.8 |
| 409 | 1662.7 | 1663.5 |
| 410 | 1676.7 | 1676.8 |
| 411 | 1751.8 | 1753.0 |
| 412 | 1690.7 | 1691.2 |
| 413 | 1723.7 | 1723.9 |
| 414 | 1718.8 | 1719.7 |
| 415 | 1710.7 | 1711.6 |
| 416 | 1738.8 | 1738.9 |
| 417 | 1766.8 | 1767.4 |
| 418 | 1784.7 | 1784.4 |
| 419 | 1313.3 | 1314.6 |
| 420 | 1256.4 | 1257.7 |
| 421 | 1631.6 | 1632.2 |
| 422 | 1342.3 | 1342.8 |

Example 11

Determination of Antibacterial Activity

A. In Vitro Determination of Antibacterial Activity

1. Determination of Minimal Inhibitory Concentrations (MICs)

Bacterial strains were obtained from either American Type Tissue Culture Collection (ATCC), Stanford University Hospital (SU), Kaiser Permanente Regional Laboratory in Berkeley (KPB), Massachusetts General Hospital (MGH), the Centers for Disease Control (CDC), the San Francisco Veterans' Administration Hospital (SFVA) or the University of California San Francisco Hospital (UCSF). Vancomycin resistant enterococci were phenotyped as Van A or Van B based on their sensitivity to teicoplanin. Some vancomycin resistant enterococci that had been genotyped as Van A, Van B, Van C1 or Van C2 were obtained from the Mayo Clinic.

Minimal inhibitory concentrations (MICs) were measured in a microdilution broth procedure under NCCLS guidelines. Routinely, the compounds were serially diluted into Mueller-Hinton broth in 96-well microtiter plates. Overnight cultures of bacterial strains were diluted based on absorbance at 600 nm so that the final concentration in each well was $5 \times 10^6$ cfu/mL. Plates were returned to a 35° C. incubator The following day (or 24 hours in the case of Enterococci strains), MICs were determined by visual inspection of the plates Strains routinely tested in the initial screen included methicillin-sensitive *Staphylococcus aureus* (MSSA), methicillin-resistant *Staphylococcus aureus*, methicillin-sensistive *Staphylococcus epidermidis* (MSSE), methicillin-resistant *Staphylococcus epidermidis* (MRSE), vancomycin sensitive *Enterococcus faecium* (VSE Fm), vancomycin sensitive *Enterococcus faecalis* (VSE Fs), vancomycin resistant *Enterococcus faecium* also resistant to teicoplanin (VRE Fm Van A), vancomycin resistant *Enterococcus faecium* sensistive to teicoplanin (VRE Fm Van B), vancomycin resistant *Enterococcus faecalis* also resistant to teicoplanin (VRE Fs Van A), vancomycin resistant *Enterococcus faecalis* sensitive to teicoplanin (VRE Fs Van B), *enterococcus gallinarium* of the Van A genotype (VRE Gm Van A), *enterococcus gallinarium* of the Van C-1 genotype (VRE Gm Van C-1), *enterococcus casseliflavus* of the Van C-2 genotype (VRE Cs Van C-2), *enterococcus flavescens* of the Van C-2 genotype (VRE Fv Van C-2), and penicillin-sensitive *Streptococcus pneumoniae* (PSSP) and penicillin-resistant *Streptococcus pneumoniae* (PSRP) Because of the inability of PSSP and PSRP to grow well in Mueller-Hinton broth, MICs with those strains were determined using either TSA broth supplemented with defibrinated blood or blood agar plates Compounds which had significant activity against the strains mentioned above were then tested for MIC values in a larger panel of clinical isolates including the species listed above as well as non-speciated coagulase negative *Staphylococcus* both sensitive and resistant to methicillin (MS-CNS and MR-CNS) In addition, they were tested for MICs against gram negative organisms, such as *Escherichia coli* and *Pseudomonas aeruginosa*.

2. Determination of Kill Time

Experiments to determine the time required to kill the bacteria were conducted as described in Lorian, "Antibiotics in Laboratory Medicine", Fourth Edition, Williams and Wilkins (1991), the disclosure of which is incorporated herein by reference in its entirety. These experiments were conducted normally with both *staphylococcus* and *enterococcus* strains.

Briefly, several colonies were selected from an agar plate and grown at 35° C. under constant agitation until it achieved a turbidity of approximately 1.5 and 10 CFU/mL. The sample was then diluted to about $6 \times 10^6$ CFU/mL and incubated at 35° C. under constant agitation was continued. At various times aliquots were removed and five ten-fold serial dilutions were performed. The pour plate method was used to determine the number of colony forming units (CFUs).

The compounds of this invention were active in the above tests in vitro tests and demonstrated a broad spectrum of activity.

B. In Vivo Determination of Antibacterial Activity

1. Acute Tolerability Studies in Mice

In these studies, a compound of this invention was administered either intravenously or subcutaneously and observed for 5-15 minutes. If there were no adverse effects, the dose was increased in a second group of mice. This dose incrementation continued until mortality occurred, or the dose was maximized. Generally, dosing began at 20 mg/kg and increased by 20 mg/kg each time until the maximum tolerated dose (MTD) is achieved.

2. Bioavailability Studies in Mice

Mice were administered a compound of this invention either intravenously or subcutaneously at a therapeutic dose (in general, approximately 50 mg/kg). Groups of animals were placed in metabolic cages so that urine and feces could be collected for analysis. Groups of animals (n=3) were sacrificed at various times (10 min, 1 hour and 4 hours). Blood was collected by cardiac puncture and the following organs were harvested—lung, liver, heart, brain, kidney, and spleen. Tissues were weighed and prepared for HPLC analysis. HPLC analysis on the tissue homogenates and fluids was used to determine the concentration of the test compound or IiI present. Metabolic products resulting from changes to the test compound were also determined at this juncture.

3. Mouse Septecemia Model

In this model, an appropriately virulent strain of bacteria (most commonly *S. aureus*, or *E. Faecalis* or *E. Faecium*) was administered to mice (N=5 to 10 mice per group) intraperitoneally. The bacteria was combined with hog gastric mucin to enhance virulence. The dose of bacteria (normally $10^6$-$10^7$) was that sufficient to induce mortality in all of the mice over a three day period. One hour after the bacteria was administered, a compound of this invention was administered in a single dose either IV or subcutaneously. Each dose was administered to groups of 5 to 10 mice, at doses that typically ranged from a maximum of about 20 mg/kg to a minimum of less than 1 mg/kg. A positive control (normally vancomycin with vancomycin sensitive strains) was administered in each experiment. The dose at which approximately 50% of the animals are saved was calculated from the results.

4. Neutropenic Thigh Model

In this model, antibacterial activity of a compound of this invention was evaluated against an appropriately virulent strain of bacteria (most commonly *S. aureus*, or *E. Faecalis* or *E. Faecium*, sensitive or resistant to vancomycin). Mice were initially rendered neutropenic by administration of cyclophosphamide at 200 mg/kg on day 0 and day 2. On day 4 they were infected in the left anterior thigh by an IM injection of a single dose of bacteria. The mice were then administered the test compound one hour after the bacteria and at various later times (normally 1, 2.5, 4 and 24 hours) the mice were sacrificed (3 per time point) and the thigh excised, homogenized and the number of CFUs (colony forming units) were determined by plating. Blood was also plated to determine the CFUs in the blood.

5. Pharmacokinetic Studies

The rate at which a compound of this invention is removed from the blood can be determined in either rats or mice. In rats, the test animals were cannulated in the jugular vein. The test compound was administered via tail vein injection, and at various time points (normally 5, 15, 30, 60 minutes and 2, 4, 6 and 24 hours) blood was withdrawn from the cannula In mice, the test compound was also administered via tail vein injection, and at various time points. Blood was normally obtained by cardiac puncture. The concentration of the remaining test compound was determined by HPLC.

The compounds of this invention were active in the above tests in vivo tests and demonstrated a broad spectrum of activity.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula:

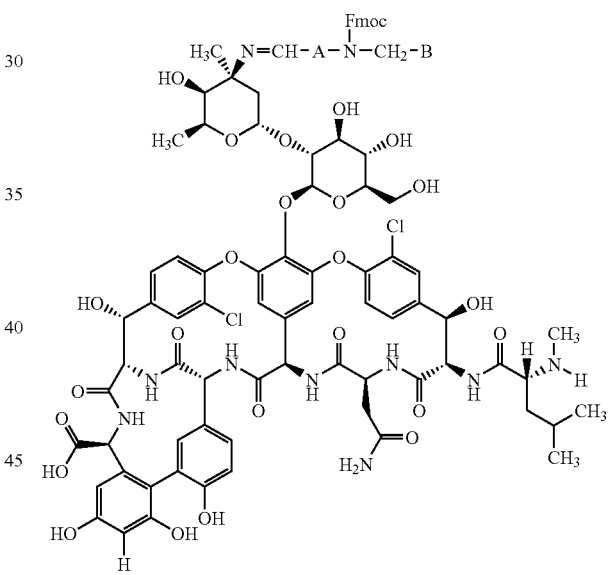

wherein

A is —CH$_2$— or —CH$_2$CH$_2$—;

B is n-heptyl, n-octyl, n-nonyl, n-decyl or n-undecyl; and

Fmoc is 9-fluorenylmethoxycarbonyl;

or a trifluoroacetic acid salt thereof.

2. The compound of claim 1, wherein A is —CH$_2$—.

3. The compound of claim 1, wherein A is —CH$_2$CH$_2$—.

4. The compound of claim 1, wherein B is n-heptyl.

5. The compound of claim 1, wherein B is n-octyl.

6. The compound of claim 1, wherein B is n-decyl.

7. The compound of claim 1, wherein B is n-undecyl.

8. A compound of the formula:

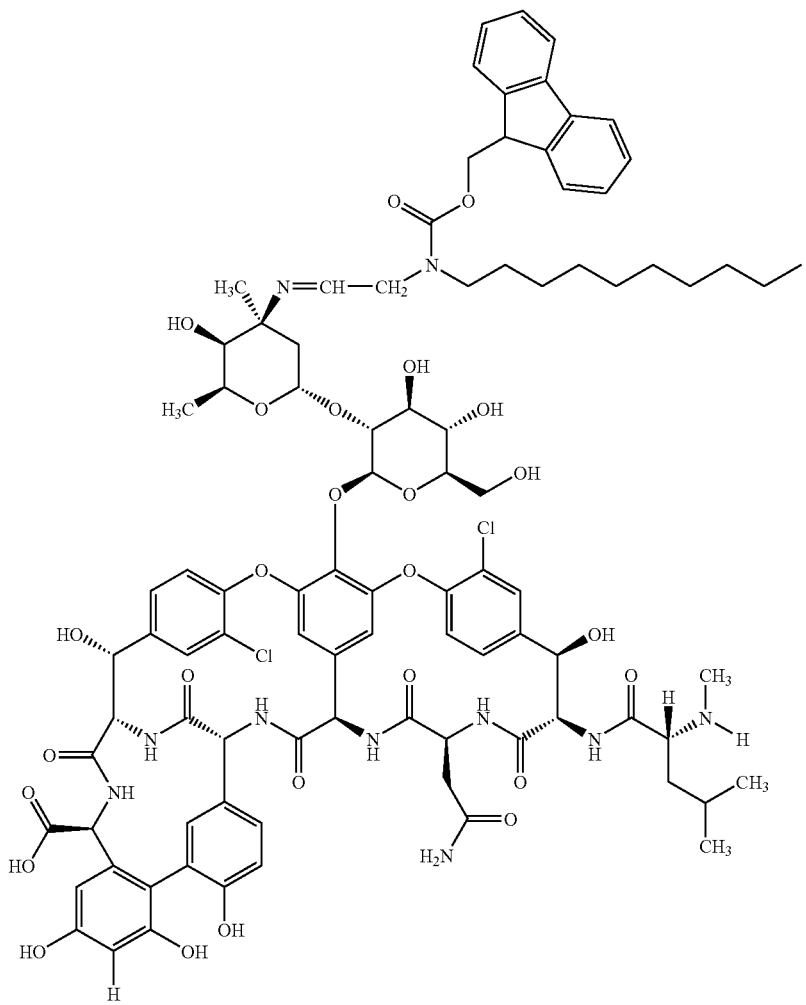
or a trifluoroacetic acid salt thereof.
9. The compound of claim 1, wherein B is n-nonyl.
* * * * *

UNITED STATES PATENT AND TRADEMARK OFFICE
CERTIFICATE OF CORRECTION

PATENT NO. : 7,723,470 B2
APPLICATION NO. : 11/977377
DATED : May 25, 2010
INVENTOR(S) : Martin S. Linsell It is certified that error appears in the above-identified patent and that said Letters Patent is hereby corrected as shown below:

Title Page, under Item (12), delete "Judice et al." and insert --Linsell--.

On the front page, under section (75) Inventors, delete the following inventors:
"J. Kevin Judice, El Granada, CA (US);
Paul Ross Fatheree, San Francisco, CA (US);
Bernice M. T. Lam, San Francisco, CA (US);
Michael R. Leadbetter, San Leandro, CA (US);
YongQi Mu, Los Altos, CA (US);
Sean Gary Trapp, San Francisco, CA (US);
Guang Yang, San Mateo, CA (US);
Yan Zhu, Foster City, CA (US);" and insert
--Martin S. Linsell, San Mateo, CA (US)--.

Signed and Sealed this

Twenty-sixth Day of October, 2010

David J. Kappos
*Director of the United States Patent and Trademark Office*